(12) United States Patent
Druke et al.

(10) Patent No.: US 11,730,958 B2
(45) Date of Patent: Aug. 22, 2023

(54) NON-INVASIVE NERVE ACTIVATOR WITH BOOSTED CHARGE DELIVERY

(71) Applicant: Neurostim Solutions, LLC, Waltham, MA (US)

(72) Inventors: Michael Bernard Druke, Half Moon Bay, CA (US); Alan E. Loh, Los Altos, CA (US); Brian Gagne, Williston, VT (US)

(73) Assignee: Neurostim Solutions, LLC, Waltham, MA (US)

( * ) Notice: Subject to any disclaimer, the term of this patent is extended or adjusted under 35 U.S.C. 154(b) by 224 days.

(21) Appl. No.: 17/123,441

(22) Filed: Dec. 16, 2020

(65) Prior Publication Data

US 2021/0178157 A1    Jun. 17, 2021

Related U.S. Application Data

(60) Provisional application No. 62/948,780, filed on Dec. 16, 2019.

(51) Int. Cl.
*A61N 1/36*       (2006.01)
*A61N 1/04*       (2006.01)

(52) U.S. Cl.
CPC ....... *A61N 1/36021* (2013.01); *A61N 1/0456* (2013.01); *A61N 1/0496* (2013.01); *A61N 1/36034* (2017.08)

(58) Field of Classification Search
CPC ............ A61N 1/36021; A61N 1/36034; A61N 1/0456; A61N 1/0496
See application file for complete search history.

(56) References Cited

U.S. PATENT DOCUMENTS 4,277,980 A    7/1981  Coats et al.
4,532,930 A    8/1985  Crosby et al.
(Continued)

FOREIGN PATENT DOCUMENTS

CN    101868279 A    10/2010
CN    107362447 A    11/2017
(Continued)

OTHER PUBLICATIONS

US 8,398,630 B2, 03/2013, Demarais et al. (withdrawn)
(Continued)

*Primary Examiner* — Allen Porter
*Assistant Examiner* — Adreanne A. Arnold
(74) *Attorney, Agent, or Firm* — Potomac Law Group, PLLC

(57) ABSTRACT

A topical nerve activation patch includes electronic circuitry embedded in the patch and electronic circuitry configured to generate an output voltage applied to electrodes. The patch further includes a controller configured to generate a treatment comprising a plurality of activation pulses that form the output voltage, the controller comprising a first real time clock and an oscillator, the treatment comprising electrical stimuli applied to the user via the electrodes. The patch further includes a charge measurement circuit configured to measure an amount of charge applied to the user from the electrical stimuli and a communication link configured to communicate with a remote activation device, the remote activation device comprising a second real time clock. The controller is configured to generate the activation pulses by measuring time intervals using the oscillator and using the second real time clock and the measured time intervals to determine activation times for the activation pulses.

20 Claims, 14 Drawing Sheets

(56) References Cited

U.S. PATENT DOCUMENTS

| | | |
|---|---|---|
| 4,542,753 A | 9/1985 | Brenman et al. |
| 4,549,556 A | 10/1985 | Tarjan et al. |
| 4,553,549 A | 11/1985 | Pope et al. |
| 4,590,949 A | 5/1986 | Pohndorf |
| 4,614,395 A | 9/1986 | Peers-Trevarton |
| 4,658,835 A | 4/1987 | Pohndorf |
| 4,677,989 A | 7/1987 | Robblee |
| 4,690,144 A | 9/1987 | Rise et al. |
| 4,702,254 A | 10/1987 | Zabara |
| 4,706,682 A | 11/1987 | Stypulkowski et al. |
| 4,717,581 A | 1/1988 | Robblee |
| 4,759,228 A | 7/1988 | Butler et al. |
| 4,800,898 A | 1/1989 | Hess et al. |
| 4,817,628 A | 4/1989 | Zealear et al. |
| 4,881,526 A | 11/1989 | Johnson et al. |
| 4,883,666 A | 11/1989 | Sabel et al. |
| 4,919,148 A | 4/1990 | Muccio |
| 4,940,453 A | 7/1990 | Cadwell |
| 4,959,532 A | 9/1990 | Owechko |
| 5,031,621 A | 7/1991 | Grandjean et al. |
| 5,035,242 A | 7/1991 | Franklin et al. |
| 5,047,005 A | 9/1991 | Cadwell |
| 5,092,332 A | 3/1992 | Lee et al. |
| 5,092,835 A | 3/1992 | Schurig et al. |
| 5,095,905 A | 3/1992 | Klepinski |
| 5,211,657 A | 5/1993 | Yamada et al. |
| 5,265,608 A | 11/1993 | Lee et al. |
| 5,381,801 A | 1/1995 | McShane et al. |
| 5,476,494 A | 12/1995 | Edell et al. |
| 5,501,703 A | 3/1996 | Holsheimer et al. |
| 5,569,307 A | 10/1996 | Schulman et al. |
| 5,575,813 A | 11/1996 | Edell et al. |
| 5,584,869 A | 12/1996 | Heck et al. |
| 5,597,381 A | 1/1997 | Rizzo, III |
| 5,603,726 A | 2/1997 | Schulman et al. |
| 5,609,616 A | 3/1997 | Schulman et al. |
| 5,628,769 A | 5/1997 | Saringer |
| 5,643,330 A | 7/1997 | Holsheimer et al. |
| 5,679,340 A | 10/1997 | Chappel |
| 5,713,922 A | 2/1998 | King |
| 5,738,625 A | 4/1998 | Gluck |
| 5,741,314 A | 4/1998 | Daly et al. |
| 5,792,209 A | 8/1998 | Varner |
| 5,795,790 A | 8/1998 | Schinstine et al. |
| 5,824,022 A | 10/1998 | Zilberman et al. |
| 5,830,651 A | 11/1998 | Cauley et al. |
| 5,837,236 A | 11/1998 | Dinsmore |
| 5,853,370 A | 12/1998 | Chance et al. |
| 5,871,534 A | 2/1999 | Messick et al. |
| 5,876,425 A | 3/1999 | Gord et al. |
| 5,891,437 A | 4/1999 | Pietropaolo et al. |
| 5,916,870 A | 6/1999 | Lee et al. |
| 5,921,245 A | 7/1999 | O'Donnell, Jr. |
| 5,922,012 A | 7/1999 | Sakano |
| 5,937,318 A | 8/1999 | Warner, Jr. et al. |
| 5,938,691 A | 8/1999 | Schulman et al. |
| 5,948,428 A | 9/1999 | Lee et al. |
| 5,987,361 A | 11/1999 | Mortimer |
| 5,989,445 A | 11/1999 | Wise et al. |
| 5,992,769 A | 11/1999 | Wise et al. |
| 6,002,960 A | 12/1999 | Sternberger et al. |
| 6,011,018 A | 1/2000 | Crabtree et al. |
| 6,016,449 A | 1/2000 | Fischell et al. |
| 6,058,331 A | 5/2000 | King |
| 6,060,048 A | 5/2000 | Cherksey |
| 6,060,054 A | 5/2000 | Staerz |
| 6,066,084 A | 5/2000 | Edrich et al. |
| 6,067,474 A | 5/2000 | Schulman et al. |
| 6,085,115 A | 7/2000 | Weaver et al. |
| 6,096,537 A | 8/2000 | Chappel |
| 6,119,071 A | 9/2000 | Gorenflo et al. |
| 6,120,538 A | 9/2000 | Rizzo, III et al. |
| 6,140,116 A | 10/2000 | Dinsmore |
| 6,178,349 B1 | 1/2001 | Kieval |
| 6,203,792 B1 | 3/2001 | Filbin |
| 6,204,053 B1 | 3/2001 | Dinsmore |
| 6,258,353 B1 | 7/2001 | Isacson et al. |
| 6,264,950 B1 | 7/2001 | Staerz |
| 6,265,175 B1 | 7/2001 | Gage et al. |
| 6,270,831 B2 | 8/2001 | Kumar et al. |
| 6,277,372 B1 | 8/2001 | Fraser et al. |
| 6,284,245 B1 | 9/2001 | Edge |
| 6,288,527 B1 | 9/2001 | Sugihara et al. |
| 6,294,383 B1 | 9/2001 | Isacson et al. |
| 6,304,784 B1 | 10/2001 | Allee et al. |
| 6,304,787 B1 | 10/2001 | Kuzma et al. |
| 6,359,550 B1 | 3/2002 | Brisebois et al. |
| 6,374,140 B1 | 4/2002 | Rise |
| 6,379,393 B1 | 4/2002 | Mavroidis et al. |
| 6,392,118 B1 | 5/2002 | Hammang et al. |
| 6,392,550 B1 | 5/2002 | Najor |
| 6,393,327 B1 | 5/2002 | Scribner |
| 6,415,186 B1 | 7/2002 | Chim et al. |
| 6,421,232 B2 | 7/2002 | Sallam |
| 6,427,083 B1 | 7/2002 | Owen et al. |
| 6,444,205 B2 | 9/2002 | Dinsmore et al. |
| 6,472,181 B1 | 10/2002 | Mineau-Hanschke |
| 6,510,347 B2 | 1/2003 | Borkan |
| 6,517,833 B2 | 2/2003 | Edge |
| 6,533,732 B1 | 3/2003 | Urmey |
| 6,537,200 B2 | 3/2003 | Leysieffer et al. |
| 6,546,291 B2 | 4/2003 | Merfeld et al. |
| 6,561,975 B1 | 5/2003 | Pool et al. |
| 6,565,503 B2 | 5/2003 | Leysieffer et al. |
| 6,575,894 B2 | 6/2003 | Leysieffer et al. |
| 6,599,695 B2 | 7/2003 | Gage et al. |
| 6,640,118 B2 | 10/2003 | Van Heerden et al. |
| 6,640,121 B1 | 10/2003 | Telischi et al. |
| RE38,323 E | 11/2003 | Sugihara et al. |
| 6,647,297 B2 | 11/2003 | Scribner |
| 6,690,974 B2 | 2/2004 | Archer et al. |
| 6,697,674 B2 | 2/2004 | Leysieffer |
| 6,727,696 B2 | 4/2004 | Kruspe et al. |
| 6,744,367 B1 | 6/2004 | Forster |
| 6,788,976 B2 | 9/2004 | Gesotti |
| 6,795,737 B2 | 9/2004 | Gielen et al. |
| 6,807,445 B2 | 10/2004 | Baumann et al. |
| 6,839,596 B2 | 1/2005 | Nelson et al. |
| 6,850,802 B2 | 2/2005 | Holsheimer |
| 6,879,855 B2 | 4/2005 | Schulman et al. |
| 6,884,122 B2 | 4/2005 | Robinson et al. |
| 6,892,097 B2 | 5/2005 | Holsheimer |
| 6,893,812 B2 | 5/2005 | Woltering et al. |
| 6,894,616 B1 | 5/2005 | Forster |
| 6,902,547 B2 | 6/2005 | Aves et al. |
| 6,931,273 B2 | 8/2005 | Groenewegen et al. |
| 6,949,251 B2 | 9/2005 | Dalal et al. |
| 6,970,745 B2 | 11/2005 | Scribner |
| 6,976,998 B2 | 12/2005 | Rizzo et al. |
| 7,001,608 B2 | 2/2006 | Fishman et al. |
| 7,003,335 B2 | 2/2006 | Briancon |
| 7,010,351 B2 | 3/2006 | Firlik et al. |
| 7,027,873 B2 | 4/2006 | Pajunk et al. |
| 7,030,411 B2 | 4/2006 | Krulevitch et al. |
| 7,037,603 B2 | 5/2006 | Lasater |
| 7,047,080 B2 | 5/2006 | Palanker et al. |
| 7,058,455 B2 | 6/2006 | Huie, Jr. et al. |
| 7,079,882 B1 | 7/2006 | Schmidt |
| 7,101,542 B1 | 9/2006 | Vallera et al. |
| 7,106,190 B1 | 9/2006 | Owens |
| 7,107,104 B2 | 9/2006 | Keravel et al. |
| 7,115,071 B1 | 10/2006 | Sunbeck |
| 7,117,034 B2 | 10/2006 | Kronberg |
| 7,120,499 B2 | 10/2006 | Thrope et al. |
| 7,127,301 B1 | 10/2006 | Dkandan et al. |
| 7,155,278 B2 | 12/2006 | King et al. |
| 7,167,750 B2 | 1/2007 | Knudson et al. |
| 7,174,223 B2 | 2/2007 | Dalton et al. |
| 7,181,288 B1 | 2/2007 | Rezai et al. |
| 7,191,018 B2 | 3/2007 | Gielen et al. |
| 7,193,414 B2 | 3/2007 | Kruspe et al. |
| 7,206,632 B2 | 4/2007 | King |
| 7,209,787 B2 | 4/2007 | DiLorenzo |
| 7,218,216 B1 | 5/2007 | Uehran |

(56) References Cited

U.S. PATENT DOCUMENTS

| | | |
|---|---|---|
| 7,218,964 B2 | 5/2007 | Hill et al. |
| 7,228,178 B2 | 6/2007 | Carroll et al. |
| 7,228,727 B2 | 6/2007 | Discenzo |
| 7,239,918 B2 | 7/2007 | Strother et al. |
| 7,249,998 B2 | 7/2007 | van Esbroeck et al. |
| 7,283,867 B2 | 10/2007 | Strother et al. |
| 7,297,420 B2 | 11/2007 | Jiang |
| 7,299,034 B2 | 11/2007 | Kates |
| 7,308,303 B2 | 12/2007 | Whitehurst et al. |
| 7,308,317 B1 | 12/2007 | Dkandan et al. |
| 7,333,851 B2 | 2/2008 | Echauz et al. |
| 7,337,004 B2 | 2/2008 | Classen et al. |
| 7,349,169 B2 | 3/2008 | Lee et al. |
| RE40,209 E | 4/2008 | Sugihara et al. |
| 7,376,467 B2 | 5/2008 | Thrope et al. |
| 7,384,145 B2 | 6/2008 | Hetling et al. |
| 7,392,093 B2 | 6/2008 | Khan |
| 7,398,255 B2 | 7/2008 | Lauer et al. |
| 7,415,309 B2 | 8/2008 | McIntyre |
| 7,420,760 B2 | 9/2008 | Zhang et al. |
| 7,422,564 B2 | 9/2008 | Parsons et al. |
| 7,435,443 B2 | 10/2008 | Jiang |
| 7,435,585 B2 | 10/2008 | Tykocinski et al. |
| 7,437,193 B2 | 10/2008 | Parramon et al. |
| 7,437,196 B2 | 10/2008 | Wyler et al. |
| 7,483,747 B2 | 1/2009 | Gliner et al. |
| 7,499,745 B2 | 3/2009 | Littrup et al. |
| 7,499,748 B2 | 3/2009 | Moffitt et al. |
| 7,502,652 B2 | 3/2009 | Gaunt et al. |
| 7,519,419 B2 | 4/2009 | Jiang et al. |
| 7,529,582 B1 | 5/2009 | DiLorenzo |
| 7,553,307 B2 | 6/2009 | Bleich et al. |
| 7,555,343 B2 | 6/2009 | Bleich |
| 7,561,919 B2 | 7/2009 | Shalev et al. |
| 7,565,199 B2 | 7/2009 | Sheffield et al. |
| 7,565,200 B2 | 7/2009 | Wyler et al. |
| 7,571,002 B2 | 8/2009 | Thrope et al. |
| 7,571,006 B2 | 8/2009 | Gordon et al. |
| 7,578,819 B2 | 8/2009 | Bleich et al. |
| 7,584,004 B2 | 9/2009 | Caparso et al. |
| 7,587,238 B2 | 9/2009 | Moffitt et al. |
| 7,598,031 B2 | 10/2009 | Liew |
| 7,599,737 B2 | 10/2009 | Yomtov et al. |
| 7,620,456 B2 | 11/2009 | Gliner et al. |
| 7,622,303 B2 | 11/2009 | Soykan et al. |
| 7,636,597 B2 | 12/2009 | Gross et al. |
| 7,643,874 B2 | 1/2010 | Nitzan et al. |
| 7,657,308 B2 | 2/2010 | Miles et al. |
| 7,658,707 B2 | 2/2010 | Topolev |
| 7,662,558 B2 | 2/2010 | Liew |
| 7,676,274 B2 | 3/2010 | Hung et al. |
| 7,680,526 B2 | 3/2010 | McIntyre et al. |
| 7,684,866 B2 | 3/2010 | Fowler et al. |
| 7,689,285 B2 | 3/2010 | Garabet |
| D613,868 S | 4/2010 | Lhuillery et al. |
| 7,699,768 B2 | 4/2010 | Kishawi et al. |
| 7,704,740 B2 | 4/2010 | Schindler et al. |
| 7,706,888 B2 | 4/2010 | Jolly |
| 7,706,893 B2 | 4/2010 | Hung et al. |
| 7,711,416 B1 | 5/2010 | Akkin et al. |
| 7,715,919 B2 | 5/2010 | Osorio et al. |
| 7,715,924 B2 | 5/2010 | Rezai et al. |
| 7,725,196 B2 | 5/2010 | Machado et al. |
| 7,732,407 B2 | 6/2010 | Hunter |
| 7,738,968 B2 | 6/2010 | Bleich |
| 7,738,969 B2 | 6/2010 | Bleich |
| 7,740,631 B2 | 6/2010 | Bleich et al. |
| 7,747,318 B2 | 6/2010 | John et al. |
| 7,756,583 B2 | 7/2010 | Demarais et al. |
| 7,756,584 B2 | 7/2010 | Sheffield et al. |
| 7,769,462 B2 | 8/2010 | Meadows et al. |
| 7,769,470 B1 | 8/2010 | Rezai et al. |
| 7,798,982 B2 | 9/2010 | Zets et al. |
| 7,799,021 B2 | 9/2010 | Leung et al. |
| 7,801,603 B2 | 9/2010 | Westlund et al. |
| 7,813,809 B2 | 10/2010 | Strother et al. |
| 7,819,801 B2 | 10/2010 | Miles et al. |
| 7,819,869 B2 | 10/2010 | Godara et al. |
| 7,831,305 B2 | 11/2010 | Gliner |
| 7,844,340 B2 | 11/2010 | Pawlowicz, III |
| 7,877,136 B1 | 1/2011 | Moffitt et al. |
| 7,892,180 B2 | 2/2011 | Epley |
| 7,894,911 B2 | 2/2011 | Greenberg et al. |
| 7,894,914 B2 | 2/2011 | Stahmann et al. |
| 7,899,542 B2 | 3/2011 | Cowan et al. |
| 7,914,842 B1 | 3/2011 | Greenberg et al. |
| 7,917,231 B2 | 3/2011 | Farah et al. |
| 7,918,802 B2 | 4/2011 | Urmey |
| 7,922,676 B2 | 4/2011 | Daskal et al. |
| 7,943,632 B2 | 5/2011 | Katzman et al. |
| 7,945,330 B2 | 5/2011 | Gliner et al. |
| 7,947,448 B2 | 5/2011 | Couillard-Despres et al. |
| RE42,449 E | 6/2011 | Forster |
| 7,959,577 B2 | 6/2011 | Schmitz et al. |
| 7,963,915 B2 | 6/2011 | Bleich |
| 7,967,751 B2 | 6/2011 | Goscha et al. |
| 7,974,689 B2 | 7/2011 | Volpe et al. |
| 7,981,144 B2 | 7/2011 | Geist et al. |
| 7,988,688 B2 | 8/2011 | Webb et al. |
| 7,991,475 B1 | 8/2011 | Tang et al. |
| 7,991,480 B2 | 8/2011 | Stahmann et al. |
| 7,992,521 B2 | 8/2011 | Bocquier |
| 8,000,782 B2 | 8/2011 | Gharib et al. |
| 8,000,796 B2 | 8/2011 | Tass et al. |
| 8,000,804 B1 | 8/2011 | Wessendorf et al. |
| 8,010,202 B2 | 8/2011 | Shah et al. |
| 8,014,868 B2 | 9/2011 | Greenberg et al. |
| 8,014,878 B2 | 9/2011 | Greenberg et al. |
| 8,025,632 B2 | 9/2011 | Einarsson |
| 8,027,716 B2 | 9/2011 | Gharib et al. |
| 8,033,996 B2 | 10/2011 | Behar |
| 8,060,210 B1 | 11/2011 | Carroll |
| 8,065,012 B2 | 11/2011 | Firlik et al. |
| 8,067,173 B2 | 11/2011 | Liew |
| 8,073,526 B2 | 12/2011 | Graham et al. |
| 8,073,546 B2 | 12/2011 | Sheffield et al. |
| 8,075,556 B2 | 12/2011 | Betts |
| 8,078,252 B2 | 12/2011 | Kipke et al. |
| 8,090,446 B2 | 1/2012 | Fowler et al. |
| 8,092,398 B2 | 1/2012 | Weinberg et al. |
| 8,095,209 B2 | 1/2012 | Flaherty |
| 8,101,358 B2 | 1/2012 | Liew |
| 8,110,358 B2 | 2/2012 | Liew |
| 8,114,019 B2 | 2/2012 | Miles et al. |
| 8,114,597 B2 | 2/2012 | Liew |
| 8,116,875 B2 | 2/2012 | Osypka et al. |
| 8,126,562 B2 | 2/2012 | Fowler et al. |
| 8,131,376 B1 | 3/2012 | Faraji et al. |
| 8,133,674 B2 | 3/2012 | Liew |
| 8,133,675 B2 | 3/2012 | Liew |
| 8,135,472 B2 | 3/2012 | Fowler et al. |
| 8,137,258 B1 | 3/2012 | Dennis et al. |
| 8,137,284 B2 | 3/2012 | Miles et al. |
| 8,140,152 B2 | 3/2012 | John et al. |
| 8,140,162 B1 | 3/2012 | Jiang et al. |
| 8,140,170 B2 | 3/2012 | Rezai et al. |
| 8,148,072 B2 | 4/2012 | Liew |
| 8,155,757 B1 | 4/2012 | Neisz et al. |
| 8,160,713 B2 | 4/2012 | Greenberg et al. |
| 8,162,846 B2 | 4/2012 | Epley |
| 8,165,685 B1 | 4/2012 | Knutson et al. |
| 8,170,676 B2 | 5/2012 | Greenberg et al. |
| 8,174,371 B2 | 5/2012 | Schwieger |
| 8,180,453 B2 | 5/2012 | Greenberg et al. |
| 8,180,460 B2 | 5/2012 | Nevsmith et al. |
| 8,192,357 B2 | 6/2012 | Miles et al. |
| 8,195,300 B2 | 6/2012 | Gliner et al. |
| 8,195,307 B2 | 6/2012 | Vilims |
| 8,200,338 B2 | 6/2012 | Grennberg et al. |
| 8,215,773 B2 | 7/2012 | Gibson-Hom et al. |
| 8,216,135 B2 | 7/2012 | Goscha et al. |
| 8,226,661 B2 | 7/2012 | Balling et al. |
| 8,228,202 B2 | 7/2012 | Buchner et al. |
| 8,239,036 B2 | 8/2012 | Shah et al. |

(56) References Cited

U.S. PATENT DOCUMENTS

| | | |
|---|---|---|
| 8,255,044 B2 | 8/2012 | Miles et al. |
| 8,257,922 B2 | 9/2012 | Liew |
| 8,260,428 B2 | 9/2012 | Fink et al. |
| 8,260,439 B2 | 9/2012 | DiUbaldi et al. |
| 8,280,516 B2 | 10/2012 | Graupe |
| 8,301,266 B1 | 10/2012 | Zilberman et al. |
| 8,303,516 B2 | 11/2012 | Schmitz et al. |
| 8,308,665 B2 | 11/2012 | Harry et al. |
| 8,313,443 B2 | 11/2012 | Tom |
| 8,323,320 B2 | 12/2012 | Lowry et al. |
| 8,328,354 B2 | 12/2012 | Li et al. |
| 8,332,037 B2 | 12/2012 | Imran |
| 8,332,044 B2 | 12/2012 | McIntyre |
| 8,346,367 B2 | 1/2013 | Carroll |
| 8,352,022 B2 | 1/2013 | Akkin et al. |
| 8,359,083 B2 | 1/2013 | Clark et al. |
| 8,364,257 B2 | 1/2013 | Van Den Eerenbeemd et al. |
| 8,364,258 B2 | 1/2013 | Della Rocca et al. |
| 8,374,698 B2 | 2/2013 | Ok et al. |
| 8,374,701 B2 | 2/2013 | Hyde et al. |
| 8,382,656 B1 | 2/2013 | Brown |
| 8,386,032 B2 | 2/2013 | Bachinski et al. |
| 8,386,053 B2 | 2/2013 | Komet |
| 8,388,678 B2 | 3/2013 | Singhal et al. |
| 8,391,970 B2 | 3/2013 | Tracey et al. |
| 8,391,986 B2 | 3/2013 | Graupe et al. |
| 8,391,987 B2 | 3/2013 | Faraji et al. |
| 8,396,556 B2 | 3/2013 | Libbus et al. |
| 8,403,841 B2 | 3/2013 | Miles et al. |
| 8,406,886 B2 | 3/2013 | Gaunt et al. |
| 8,412,328 B2 | 4/2013 | Whelan et al. |
| 8,412,335 B2 | 4/2013 | Gliner et al. |
| 8,417,345 B2 | 4/2013 | Machado et al. |
| 8,419,653 B2 | 4/2013 | Bleich et al. |
| 8,428,732 B2 | 4/2013 | Nishida et al. |
| 8,428,738 B2 | 4/2013 | Valencia |
| 8,428,739 B2 | 4/2013 | Ahuja et al. |
| 8,430,882 B2 | 4/2013 | Lowry et al. |
| 8,444,640 B2 | 5/2013 | Demarais et al. |
| 8,457,764 B2 | 6/2013 | Ramachandran et al. |
| 8,460,167 B2 | 6/2013 | Chornenky et al. |
| 8,463,383 B2 | 6/2013 | Sakai et al. |
| 8,473,048 B2 | 6/2013 | Greenberg et al. |
| 8,494,640 B2 | 7/2013 | Peterson et al. |
| 8,494,642 B2 | 7/2013 | Cowan et al. |
| 8,498,717 B2 | 7/2013 | Lee et al. |
| 8,498,720 B2 | 7/2013 | Pellinen et al. |
| 8,506,613 B2 | 8/2013 | Webb et al. |
| 8,509,903 B2 | 8/2013 | York et al. |
| 8,512,235 B2 | 8/2013 | Miles et al. |
| 8,515,533 B2 | 8/2013 | Rofougaran et al. |
| 8,515,543 B2 | 8/2013 | Greenberg et al. |
| 8,517,961 B2 | 8/2013 | Imran et al. |
| 8,524,311 B1 | 9/2013 | Greenberg et al. |
| 8,532,776 B2 | 9/2013 | Greenberg et al. |
| 8,538,537 B2 | 9/2013 | Hulvershorn et al. |
| 8,543,210 B2 | 9/2013 | Sharma |
| 8,548,600 B2 | 10/2013 | Deem et al. |
| 8,554,328 B2 | 10/2013 | Faraji et al. |
| 8,554,337 B2 | 10/2013 | Barolat |
| 8,556,838 B2 | 10/2013 | Moutray |
| 8,560,041 B2 | 10/2013 | Flaherty et al. |
| 8,562,521 B2 | 10/2013 | Miles et al. |
| 8,565,894 B2 | 10/2013 | Vetter et al. |
| 8,568,331 B2 | 10/2013 | Bertagnoli et al. |
| 8,571,665 B2 | 10/2013 | Moffitt et al. |
| 8,579,837 B1 | 11/2013 | Makower et al. |
| 8,583,238 B1 | 11/2013 | Heldman et al. |
| 8,588,918 B2 | 11/2013 | Bighei, II |
| 8,594,798 B2 | 11/2013 | Osorio et al. |
| 8,600,514 B1 | 12/2013 | Carroll |
| 8,608,664 B2 | 12/2013 | Kunitake et al. |
| 8,612,002 B2 | 12/2013 | Faltys et al. |
| 8,615,308 B2 | 12/2013 | Hung et al. |
| 8,617,808 B2 | 12/2013 | Braesch-Andersen et al. |
| 8,626,265 B2 | 1/2014 | Hempel et al. |
| 8,626,305 B2 | 1/2014 | Nielsen et al. |
| 8,628,469 B2 | 1/2014 | Miles et al. |
| 8,634,930 B2 | 1/2014 | Dalal et al. |
| 8,634,932 B1 | 1/2014 | Ye et al. |
| 8,639,344 B2 | 1/2014 | Greenberg et al. |
| 8,644,900 B2 | 2/2014 | Balberg et al. |
| 8,644,937 B2 | 2/2014 | Greenberg et al. |
| 8,644,938 B2 | 2/2014 | Craggs |
| 8,647,346 B2 | 2/2014 | Bleich et al. |
| 8,649,845 B2 | 2/2014 | McIntyre et al. |
| 8,649,868 B2 | 2/2014 | Greenberg et al. |
| 8,652,129 B2 | 2/2014 | Wu et al. |
| 8,652,187 B2 | 2/2014 | Wells et al. |
| 8,655,455 B2 | 2/2014 | Mann et al. |
| 8,660,655 B2 | 2/2014 | Peterson et al. |
| 8,666,500 B2 | 3/2014 | Greenberg et al. |
| 8,667,971 B2 | 3/2014 | Makkar et al. |
| 8,667,972 B2 | 3/2014 | Makkar et al. |
| 8,669,058 B2 | 3/2014 | Liew |
| 8,670,837 B2 | 3/2014 | Daneshvar et al. |
| 8,674,838 B2 | 3/2014 | Konishi et al. |
| 8,676,274 B2 | 3/2014 | Li |
| 8,682,443 B2 | 3/2014 | Faraji et al. |
| 8,698,637 B2 | 4/2014 | Raichman |
| 8,702,685 B2 | 4/2014 | Schwartz et al. |
| 8,706,241 B2 | 4/2014 | Firlik et al. |
| 8,708,899 B2 | 4/2014 | Miles et al. |
| 8,712,517 B2 | 4/2014 | Jolly |
| 8,712,538 B2 | 4/2014 | Greenberg et al. |
| 8,712,549 B2 | 4/2014 | Zdeblick et al. |
| 8,721,637 B2 | 5/2014 | Zarins et al. |
| 8,725,251 B2 | 5/2014 | Della Rocca et al. |
| 8,734,339 B2 | 5/2014 | Rao et al. |
| 8,740,783 B2 | 6/2014 | Gharib et al. |
| 8,740,896 B2 | 6/2014 | Zarins et al. |
| 8,744,570 B2 | 6/2014 | Lee et al. |
| 8,750,957 B2 | 6/2014 | Tang et al. |
| 8,753,271 B1 | 6/2014 | Miles et al. |
| 8,755,896 B2 | 6/2014 | Humayun et al. |
| 8,761,889 B2 | 6/2014 | Wingeier et al. |
| 8,774,922 B2 | 7/2014 | Zarins et al. |
| 8,774,937 B2 | 7/2014 | Mercanzini et al. |
| 8,777,942 B2 | 7/2014 | Wu et al. |
| 8,781,603 B2 | 7/2014 | Ye et al. |
| 8,784,461 B2 | 7/2014 | Webb et al. |
| 8,788,064 B2 | 7/2014 | Mercanzini et al. |
| 8,788,065 B2 | 7/2014 | Rezai et al. |
| 8,790,338 B2 | 7/2014 | Asirvatham et al. |
| 8,798,756 B2 | 8/2014 | McClure et al. |
| 8,801,589 B2 | 8/2014 | Peterchev et al. |
| 8,805,467 B2 | 8/2014 | Yobas et al. |
| 8,805,517 B2 | 8/2014 | Radivojevic et al. |
| 8,805,521 B2 | 8/2014 | Carroll |
| 8,821,396 B1 | 9/2014 | Miles et al. |
| 8,831,750 B2 | 9/2014 | Ramachandran et al. |
| 8,834,545 B2 | 9/2014 | Statfurd et al. |
| 8,835,163 B2 | 9/2014 | Zhao et al. |
| 8,843,201 B1 | 9/2014 | Heldman et al. |
| 8,843,204 B2 | 9/2014 | Garnham et al. |
| 8,843,210 B2 | 9/2014 | Simon et al. |
| 8,849,412 B2 | 9/2014 | Perryman et al. |
| 8,855,767 B2 | 10/2014 | Faltys et al. |
| 8,862,236 B2 | 10/2014 | Wolpaw et al. |
| 8,864,665 B2 | 10/2014 | Rotondo et al. |
| 8,864,759 B2 | 10/2014 | Godara et al. |
| 8,866,621 B2 | 10/2014 | Wolfe et al. |
| 8,868,164 B2 | 10/2014 | Kabakov et al. |
| 8,868,172 B2 | 10/2014 | Leyde et al. |
| 8,868,216 B2 | 10/2014 | Dunagan |
| 8,870,857 B2 | 10/2014 | Seymour et al. |
| 8,874,216 B2 | 10/2014 | Kim et al. |
| 8,874,239 B2 | 10/2014 | Greenberg et al. |
| 8,880,189 B2 | 11/2014 | Lipani |
| 8,886,324 B2 | 11/2014 | Beuter et al. |
| 8,888,773 B2 | 11/2014 | Chang et al. |
| 8,892,215 B2 | 11/2014 | Lipani |
| 8,903,494 B2 | 12/2014 | Goldwasser et al. |
| 8,903,501 B2 | 12/2014 | Perryman |

(56) References Cited

U.S. PATENT DOCUMENTS

| | | |
|---|---|---|
| 8,909,343 B2 | 12/2014 | Towe |
| 8,909,344 B2 | 12/2014 | Arie et al. |
| 8,909,345 B1 | 12/2014 | Danilov et al. |
| 8,912,149 B1 | 12/2014 | Rawat et al. |
| 8,915,846 B2 | 12/2014 | Miles et al. |
| 8,915,867 B2 | 12/2014 | Imran et al. |
| 8,918,178 B2 | 12/2014 | Simon et al. |
| 8,921,473 B1 | 12/2014 | Hyman |
| 8,926,959 B2 | 1/2015 | Deisseroth et al. |
| 8,929,990 B2 | 1/2015 | Moffitt et al. |
| 8,932,196 B2 | 1/2015 | Chornenky et al. |
| 8,942,797 B2 | 1/2015 | Bartol et al. |
| 8,942,812 B2 | 1/2015 | Machado et al. |
| 8,942,821 B2 | 1/2015 | Barolat |
| 8,945,004 B2 | 2/2015 | Miles et al. |
| 8,945,216 B2 | 2/2015 | Parker et al. |
| 8,948,884 B2 | 2/2015 | Ramachandran et al. |
| 8,951,193 B2 | 2/2015 | Ong et al. |
| 8,954,144 B2 | 2/2015 | Anderson et al. |
| 8,954,150 B2 | 2/2015 | Swanson et al. |
| 8,954,157 B2 | 2/2015 | Faraji et al. |
| 8,954,167 B2 | 2/2015 | Zarembo et al. |
| 8,956,387 B2 | 2/2015 | Naghavi et al. |
| 8,958,862 B2 | 2/2015 | Hetke et al. |
| 8,958,883 B2 | 2/2015 | Mueller et al. |
| 8,958,890 B2 | 2/2015 | Kipke et al. |
| 8,965,513 B2 | 2/2015 | Wingeier et al. |
| 8,969,532 B2 | 3/2015 | DeFrees et al. |
| 8,972,026 B2 | 3/2015 | Kipke et al. |
| 8,974,402 B2 | 3/2015 | Oddsson et al. |
| 8,983,593 B2 | 3/2015 | Bartol et al. |
| 8,983,601 B2 | 3/2015 | Fukamachi et al. |
| 8,983,628 B2 | 3/2015 | Simon et al. |
| 8,983,629 B2 | 3/2015 | Simon et al. |
| 8,985,057 B2 | 3/2015 | Woodward |
| 8,986,294 B2 | 3/2015 | Demarais et al. |
| 8,992,522 B2 | 3/2015 | Pellegrino et al. |
| 8,996,131 B1 | 3/2015 | Owen et al. |
| 8,998,894 B2 | 4/2015 | Mauch et al. |
| 9,002,458 B2 | 4/2015 | Pal et al. |
| 9,002,477 B2 | 4/2015 | Burnett |
| 9,005,191 B2 | 4/2015 | Azamian et al. |
| 9,008,784 B2 | 4/2015 | Chan et al. |
| 9,014,810 B2 | 4/2015 | Sauter-Starace et al. |
| 9,014,811 B2 | 4/2015 | Pal et al. |
| 9,014,823 B2 | 4/2015 | Simon et al. |
| 9,019,106 B2 | 4/2015 | Alameh et al. |
| 9,020,598 B2 | 4/2015 | Simon et al. |
| 9,020,612 B1 | 4/2015 | Danilov et al. |
| 9,023,037 B2 | 5/2015 | Zarins et al. |
| 9,034,640 B2 | 5/2015 | Matos et al. |
| 9,037,268 B2 | 5/2015 | Knight |
| 9,042,958 B2 | 5/2015 | Karmarkar et al. |
| 9,043,001 B2 | 5/2015 | Simon et al. |
| 9,044,596 B2 | 6/2015 | Mahadevan-Jansen et al. |
| 9,044,611 B2 | 6/2015 | Zhao et al. |
| 9,056,197 B2 | 6/2015 | Kishawi et al. |
| 9,061,097 B2 | 6/2015 | Holt et al. |
| 9,061,134 B2 | 6/2015 | Askin, III et al. |
| 9,061,135 B1 | 6/2015 | Keller et al. |
| 9,072,886 B2 | 7/2015 | Gaunt et al. |
| 9,072,889 B1 | 7/2015 | Guarraia et al. |
| 9,072,891 B1 | 7/2015 | Rao |
| 9,084,550 B1 | 7/2015 | Bartol et al. |
| 9,084,610 B2 | 7/2015 | Goshgarian et al. |
| 9,084,895 B2 | 7/2015 | Greenberg et al. |
| 9,084,900 B2 | 7/2015 | Hershey et al. |
| 9,089,341 B2 | 7/2015 | Chomas et al. |
| 9,089,687 B2 | 7/2015 | Lee et al. |
| 9,089,691 B2 | 7/2015 | Libbus et al. |
| 9,095,267 B2 | 8/2015 | Halpern et al. |
| 9,095,320 B2 | 8/2015 | Littrup et al. |
| 9,095,538 B2 | 8/2015 | Yu et al. |
| 9,101,279 B2 | 8/2015 | Ritchey et al. |
| 9,113,912 B1 | 8/2015 | Mehta et al. |
| 9,114,261 B2 | 8/2015 | Yonce |
| 9,119,628 B1 | 9/2015 | Mehta et al. |
| 9,119,964 B2 | 9/2015 | Marnfeldt |
| 9,126,197 B2 | 9/2015 | Orwar et al. |
| 9,132,058 B2 | 9/2015 | Imboden et al. |
| 9,138,579 B2 | 9/2015 | Wolpaw et al. |
| 9,144,677 B2 | 9/2015 | Garnham et al. |
| 9,155,887 B2 | 10/2015 | Miller, III et al. |
| 9,158,890 B2 | 10/2015 | Meredith et al. |
| 9,162,010 B2 | 10/2015 | Lenarz et al. |
| 9,162,064 B2 | 10/2015 | Faltys et al. |
| 9,173,585 B2 | 11/2015 | Tsampazis et al. |
| 9,179,850 B2 | 11/2015 | Wingeier et al. |
| 9,179,875 B2 | 11/2015 | Hua |
| 9,189,613 B1 | 11/2015 | Tuthill et al. |
| 9,192,757 B2 | 11/2015 | Seymour |
| 9,192,767 B2 | 11/2015 | Mercanzini et al. |
| 9,199,089 B2 | 12/2015 | Perryman et al. |
| 9,205,275 B2 | 12/2015 | Pan et al. |
| 9,220,897 B2 | 12/2015 | Perryman et al. |
| 9,220,899 B2 | 12/2015 | Cattaneo et al. |
| 9,220,900 B2 | 12/2015 | Libbus et al. |
| 9,221,177 B2 | 12/2015 | Herr et al. |
| 9,227,051 B1 | 1/2016 | Fisk et al. |
| 9,227,056 B1 | 1/2016 | Heldman et al. |
| 9,254,382 B2 | 2/2016 | Ahmad et al. |
| 9,855,427 B2 | 1/2018 | Bennett et al. |
| 9,895,546 B2 | 2/2018 | Jiang et al. |
| 10,009,852 B2 | 6/2018 | Law et al. |
| 10,021,239 B2 | 7/2018 | Ledingham et al. |
| 10,118,040 B2 | 11/2018 | Zhu |
| 10,226,575 B2 | 3/2019 | Miller et al. |
| 10,243,412 B1 | 3/2019 | Fink et al. |
| 10,257,885 B2 | 4/2019 | Chung |
| 10,261,568 B2 | 4/2019 | Jensen et al. |
| 10,303,122 B2 | 5/2019 | Choi et al. |
| 10,342,977 B2 | 7/2019 | Raghunathan |
| 10,412,828 B1 | 9/2019 | Tamakawa |
| 2001/0034477 A1 | 10/2001 | Mansfield et al. |
| 2001/0055776 A1 | 12/2001 | Greenwalt |
| 2002/0009461 A1 | 1/2002 | Isacson et al. |
| 2002/0019652 A1 | 2/2002 | Silva et al. |
| 2002/0031497 A1 | 3/2002 | Fraser et al. |
| 2002/0034819 A1 | 3/2002 | Smith et al. |
| 2002/0055779 A1 | 5/2002 | Andrews |
| 2002/0090722 A1 | 7/2002 | Dominko et al. |
| 2002/0136705 A1 | 9/2002 | Dinsmore |
| 2002/0176849 A1 | 11/2002 | Slepian |
| 2003/0002297 A1 | 1/2003 | Nemtsev |
| 2003/0004547 A1 | 1/2003 | Owen et al. |
| 2003/0049328 A1 | 3/2003 | Dalal et al. |
| 2003/0088274 A1 | 5/2003 | Gliner et al. |
| 2003/0097161 A1 | 5/2003 | Firlik et al. |
| 2003/0100367 A1 | 5/2003 | Cooke |
| 2003/0104993 A1 | 6/2003 | Rueger et al. |
| 2003/0109901 A1 | 6/2003 | Greatbatch |
| 2003/0125786 A1 | 7/2003 | Gliner et al. |
| 2003/0149450 A1 | 8/2003 | Mayberg |
| 2003/0157712 A1 | 8/2003 | Daniel et al. |
| 2003/0195441 A1 | 10/2003 | Firouzgar |
| 2003/0198664 A1 | 10/2003 | Sullivan et al. |
| 2003/0232055 A1 | 12/2003 | Medzhitov |
| 2004/0005291 A1 | 1/2004 | Rogers et al. |
| 2004/0014662 A1 | 1/2004 | Lindquist et al. |
| 2004/0028613 A1 | 2/2004 | Quay |
| 2004/0030365 A1 | 2/2004 | Rubin |
| 2004/0038888 A1 | 2/2004 | Mercer et al. |
| 2004/0048279 A1 | 3/2004 | Olek et al. |
| 2004/0048373 A1 | 3/2004 | Gage et al. |
| 2004/0049134 A1 | 3/2004 | Fosaya et al. |
| 2004/0054300 A1 | 3/2004 | Hung et al. |
| 2004/0062755 A1 | 4/2004 | Smith et al. |
| 2004/0064052 A1 | 4/2004 | Chance et al. |
| 2004/0081652 A1 | 4/2004 | Zack et al. |
| 2004/0093093 A1 | 5/2004 | Andrews |
| 2004/0097401 A1 | 5/2004 | Datta |
| 2004/0097839 A1 | 5/2004 | Epley |
| 2004/0102525 A1 | 5/2004 | Kozachuk |
| 2004/0106966 A1 | 6/2004 | Scribner et al. |

(56) References Cited

U.S. PATENT DOCUMENTS

| | | |
|---|---|---|
| 2004/0121464 A1 | 6/2004 | Rathjen et al. |
| 2004/0143170 A1 | 7/2004 | DuRousseau |
| 2004/0147975 A1 | 7/2004 | Popovic et al. |
| 2004/0156826 A1 | 8/2004 | Dangond et al. |
| 2004/0162583 A1 | 8/2004 | Bingham et al. |
| 2004/0172100 A1 | 9/2004 | Humayun et al. |
| 2004/0172102 A1 | 9/2004 | Leysieffer |
| 2004/0185557 A1 | 9/2004 | Smith et al. |
| 2004/0199235 A1 | 10/2004 | Younis |
| 2004/0212504 A1 | 10/2004 | Forcier et al. |
| 2004/0219184 A1 | 11/2004 | Brown et al. |
| 2004/0228831 A1 | 11/2004 | Belinka et al. |
| 2004/0229702 A1 | 11/2004 | Cooke |
| 2004/0230226 A1 | 11/2004 | Bingham et al. |
| 2004/0243021 A1 | 12/2004 | Murphy et al. |
| 2005/0003998 A1 | 1/2005 | Bertilsson et al. |
| 2005/0015133 A1 | 1/2005 | Ibrahim et al. |
| 2005/0020519 A1 | 1/2005 | Albiston et al. |
| 2005/0020945 A1 | 1/2005 | Tosaya et al. |
| 2005/0038473 A1 | 2/2005 | Tamarkin et al. |
| 2005/0054096 A1 | 3/2005 | Piniella |
| 2005/0054907 A1 | 3/2005 | Page et al. |
| 2005/0070819 A1 | 3/2005 | Poux et al. |
| 2005/0073649 A1 | 4/2005 | Spector |
| 2005/0107859 A1 | 5/2005 | Low et al. |
| 2005/0125044 A1 | 6/2005 | Tracey |
| 2005/0165323 A1 | 7/2005 | Montgomery et al. |
| 2005/0203366 A1 | 9/2005 | Donoghue et al. |
| 2005/0203601 A1 | 9/2005 | Palanker et al. |
| 2005/0222631 A1 | 10/2005 | Dalal et al. |
| 2005/0226852 A1 | 10/2005 | Toda et al. |
| 2005/0234370 A1 | 10/2005 | Beal et al. |
| 2005/0267552 A1 | 12/2005 | Conquergood et al. |
| 2005/0272097 A1 | 12/2005 | Calenoff |
| 2005/0273890 A1 | 12/2005 | Flaherty et al. |
| 2005/0277918 A1 | 12/2005 | Shah et al. |
| 2006/0034767 A1 | 2/2006 | Lum et al. |
| 2006/0047326 A1 | 3/2006 | Wheeler |
| 2006/0049950 A1 | 3/2006 | Lockhart |
| 2006/0049957 A1 | 3/2006 | Surgenor et al. |
| 2006/0058627 A1 | 3/2006 | Flaherty et al. |
| 2006/0118035 A1 | 6/2006 | Lasater |
| 2006/0122458 A1 | 6/2006 | Bleich |
| 2006/0122529 A1 | 6/2006 | Tsau |
| 2006/0122864 A1 | 6/2006 | Gottesman et al. |
| 2006/0140930 A1 | 6/2006 | Rodriguez et al. |
| 2006/0149345 A1 | 7/2006 | Boggs et al. |
| 2006/0161225 A1 | 7/2006 | Sormann et al. |
| 2006/0167498 A1 | 7/2006 | DiLorenzo |
| 2006/0167564 A1 | 7/2006 | Flaherty et al. |
| 2006/0171933 A1 | 8/2006 | Short |
| 2006/0184219 A1 | 8/2006 | Pajunk et al. |
| 2006/0190056 A1 | 8/2006 | Fowler et al. |
| 2006/0195146 A1 | 8/2006 | Tracey et al. |
| 2006/0195153 A1 | 8/2006 | Diubaldi et al. |
| 2006/0206167 A1 | 9/2006 | Flaherty et al. |
| 2006/0206178 A1 | 9/2006 | Kim |
| 2006/0234376 A1 | 10/2006 | Mistry et al. |
| 2006/0263336 A1 | 11/2006 | Caplan |
| 2006/0265037 A1 | 11/2006 | Kuzma |
| 2006/0281130 A1 | 12/2006 | Bock et al. |
| 2007/0005106 A1 | 1/2007 | Adducci |
| 2007/0021803 A1 | 1/2007 | Deem et al. |
| 2007/0043591 A1 | 2/2007 | Meretei et al. |
| 2007/0049814 A1 | 3/2007 | Muccio |
| 2007/0049842 A1 | 3/2007 | Hill et al. |
| 2007/0067004 A1 | 3/2007 | Boveja et al. |
| 2007/0073361 A1 | 3/2007 | Goren et al. |
| 2007/0088335 A1 | 4/2007 | Jolly |
| 2007/0100393 A1 | 5/2007 | Whitehurst et al. |
| 2007/0102009 A1 | 5/2007 | Wong et al. |
| 2007/0107071 A1 | 5/2007 | Couillard-Despres |
| 2007/0123778 A1 | 5/2007 | Kantorovich |
| 2007/0129769 A1 | 6/2007 | Bourget et al. |
| 2007/0134657 A1 | 6/2007 | Poznansky et al. |
| 2007/0135846 A1 | 6/2007 | Knudson et al. |
| 2007/0165322 A1 | 7/2007 | Strom et al. |
| 2007/0173893 A1 | 7/2007 | Pitts |
| 2007/0173903 A1 | 7/2007 | Goren et al. |
| 2007/0179558 A1 | 8/2007 | Gliner et al. |
| 2007/0180542 A1 | 8/2007 | Brinster et al. |
| 2007/0192881 A1 | 8/2007 | Brinster et al. |
| 2007/0203533 A1 | 8/2007 | Goren et al. |
| 2007/0208212 A1 | 9/2007 | DiLorenzo |
| 2007/0208385 A1 | 9/2007 | Carroll et al. |
| 2007/0219074 A1 | 9/2007 | Pride |
| 2007/0239211 A1 | 10/2007 | Lorincz et al. |
| 2007/0249952 A1 | 10/2007 | Rubin et al. |
| 2007/0276449 A1 | 11/2007 | Gunter et al. |
| 2007/0282396 A1 | 12/2007 | Overstreet et al. |
| 2007/0287613 A1 | 12/2007 | Adducci |
| 2007/0293893 A1 | 12/2007 | Stolen et al. |
| 2007/0299483 A1 | 12/2007 | Strother et al. |
| 2008/0002276 A1 | 1/2008 | Strom et al. |
| 2008/0033520 A1 | 2/2008 | Jolly |
| 2008/0040951 A1 | 2/2008 | Kates |
| 2008/0057028 A1 | 3/2008 | Alitalo et al. |
| 2008/0064946 A1 | 3/2008 | Greenberg et al. |
| 2008/0071321 A1 | 3/2008 | Boggs et al. |
| 2008/0074794 A1 | 3/2008 | Lee et al. |
| 2008/0077192 A1 | 3/2008 | Harry et al. |
| 2008/0095747 A1 | 4/2008 | Rutishauser et al. |
| 2008/0097530 A1 | 4/2008 | Muccio et al. |
| 2008/0120029 A1 | 5/2008 | Zelek et al. |
| 2008/0125870 A1 | 5/2008 | Carmichael et al. |
| 2008/0133016 A1 | 6/2008 | Heinz |
| 2008/0139907 A1 | 6/2008 | Rao et al. |
| 2008/0154335 A1 | 6/2008 | Rope et al. |
| 2008/0161879 A1 | 7/2008 | Firlik et al. |
| 2008/0161882 A1 | 7/2008 | Firlik et al. |
| 2008/0161887 A1 | 7/2008 | Hagen |
| 2008/0170234 A1 | 7/2008 | Kim |
| 2008/0170316 A1 | 7/2008 | Kim |
| 2008/0195163 A1 | 8/2008 | Scharmer |
| 2008/0200967 A1 | 8/2008 | Ponomarev et al. |
| 2008/0208280 A1 | 8/2008 | Lindenthaler et al. |
| 2008/0215112 A1 | 9/2008 | Firlik et al. |
| 2008/0221653 A1 | 9/2008 | Agrawal et al. |
| 2008/0241208 A1 | 10/2008 | Shanley et al. |
| 2008/0242607 A1 | 10/2008 | DeFrees |
| 2008/0243218 A1 | 10/2008 | Bottomley et al. |
| 2008/0248959 A1 | 10/2008 | DeFrees |
| 2008/0249439 A1 | 10/2008 | Tracey et al. |
| 2008/0253992 A1 | 10/2008 | DeFrees et al. |
| 2008/0255582 A1 | 10/2008 | Harris |
| 2008/0262557 A1 | 10/2008 | Brown |
| 2008/0262584 A1 | 10/2008 | Bottomley et al. |
| 2008/0274958 A1 | 11/2008 | DeFrees |
| 2008/0275546 A1 | 11/2008 | Storey et al. |
| 2008/0280818 A1 | 11/2008 | DeFrees |
| 2008/0312538 A1 | 12/2008 | Shahar et al. |
| 2008/0318314 A1 | 12/2008 | Fulga et al. |
| 2009/0012586 A1 | 1/2009 | Kepecs |
| 2009/0012590 A1 | 1/2009 | Inman et al. |
| 2009/0029912 A1 | 1/2009 | Gronthos et al. |
| 2009/0036938 A1 | 2/2009 | Shipley et al. |
| 2009/0036945 A1 | 2/2009 | Chancellor et al. |
| 2009/0054800 A1 | 2/2009 | Martinerie et al. |
| 2009/0054950 A1 | 2/2009 | Stephens |
| 2009/0076421 A1 | 3/2009 | Grant |
| 2009/0076444 A1 | 3/2009 | Machado et al. |
| 2009/0086015 A1 | 4/2009 | Larsen et al. |
| 2009/0105149 A1 | 4/2009 | Albrechtsen et al. |
| 2009/0112278 A1 | 4/2009 | Wingeier et al. |
| 2009/0112279 A1 | 4/2009 | Wingeier et al. |
| 2009/0118777 A1 | 5/2009 | Iki et al. |
| 2009/0118788 A1 | 5/2009 | Firlik et al. |
| 2009/0124965 A1 | 5/2009 | Greenberg et al. |
| 2009/0131995 A1 | 5/2009 | Sloan et al. |
| 2009/0132018 A1 | 5/2009 | DiUbaldi et al. |
| 2009/0149782 A1 | 6/2009 | Cohen |
| 2009/0149900 A1 | 6/2009 | Moffitt et al. |
| 2009/0157091 A1 | 6/2009 | Buysman |
| 2009/0171381 A1 | 7/2009 | Schmitz et al. |

(56) References Cited

U.S. PATENT DOCUMENTS

| | | |
|---|---|---|
| 2009/0182393 A1 | 7/2009 | Bachinski |
| 2009/0201671 A1 | 8/2009 | Huntley |
| 2009/0214474 A1 | 8/2009 | Jennings |
| 2009/0215896 A1 | 8/2009 | Morseman et al. |
| 2009/0220466 A1 | 9/2009 | Ratajczak et al. |
| 2009/0226598 A1 | 9/2009 | Feng et al. |
| 2009/0227025 A1 | 9/2009 | Nichols et al. |
| 2009/0227831 A1 | 9/2009 | Burnett et al. |
| 2009/0227965 A1 | 9/2009 | Wijesiriwardana |
| 2009/0234265 A1 | 9/2009 | Reid et al. |
| 2009/0258048 A1 | 10/2009 | Ward et al. |
| 2009/0270958 A1 | 10/2009 | Greenberg et al. |
| 2009/0292338 A1 | 11/2009 | Gordon et al. |
| 2009/0299439 A1 | 12/2009 | Mire et al. |
| 2009/0306728 A1 | 12/2009 | Wright et al. |
| 2009/0306745 A1 | 12/2009 | Parker et al. |
| 2009/0326612 A1 | 12/2009 | Distler |
| 2010/0004654 A1 | 1/2010 | Schmitz et al. |
| 2010/0010550 A1 | 1/2010 | Ponomarev et al. |
| 2010/0016732 A1 | 1/2010 | Wells et al. |
| 2010/0035299 A1 | 2/2010 | DeFrees et al. |
| 2010/0037755 A1 | 2/2010 | McMillen et al. |
| 2010/0042180 A1 | 2/2010 | Mueller et al. |
| 2010/0042185 A1 | 2/2010 | Curtis |
| 2010/0045595 A1 | 2/2010 | Bakke |
| 2010/0047915 A1 | 2/2010 | Soykan et al. |
| 2010/0092983 A1 | 4/2010 | Liew |
| 2010/0092984 A1 | 4/2010 | Liew |
| 2010/0094311 A1 | 4/2010 | Jolly et al. |
| 2010/0099786 A1 | 4/2010 | Dias et al. |
| 2010/0112026 A1 | 5/2010 | Karp et al. |
| 2010/0114195 A1 | 5/2010 | Burnes et al. |
| 2010/0124745 A1 | 5/2010 | Liew |
| 2010/0124746 A1 | 5/2010 | Liew |
| 2010/0145427 A1 | 6/2010 | Gliner et al. |
| 2010/0168739 A1 | 7/2010 | Wu et al. |
| 2010/0179284 A1 | 7/2010 | Ward et al. |
| 2010/0185042 A1 | 7/2010 | Schneider et al. |
| 2010/0189712 A1 | 7/2010 | L'Heureux et al. |
| 2010/0203520 A1 | 8/2010 | Liew |
| 2010/0204538 A1 | 8/2010 | Burnett et al. |
| 2010/0204777 A1 | 8/2010 | Storey et al. |
| 2010/0211172 A1 | 8/2010 | Bellamkonda et al. |
| 2010/0222630 A1 | 9/2010 | Mangrum et al. |
| 2010/0222844 A1 | 9/2010 | Troosters et al. |
| 2010/0241195 A1 | 9/2010 | Meadows et al. |
| 2010/0268055 A1 | 10/2010 | Jung et al. |
| 2010/0268125 A9 | 10/2010 | Epley |
| 2010/0280570 A1 | 11/2010 | Sturm et al. |
| 2010/0280571 A1 | 11/2010 | Sloan |
| 2010/0286067 A1 | 11/2010 | DeFrees |
| 2010/0292759 A1 | 11/2010 | Hahn et al. |
| 2010/0298916 A1 | 11/2010 | Rabischong et al. |
| 2010/0304864 A1 | 12/2010 | Johnson et al. |
| 2010/0305674 A1 | 12/2010 | Zarembo et al. |
| 2010/0310529 A1 | 12/2010 | Aizman |
| 2010/0324355 A1 | 12/2010 | Spitaels et al. |
| 2010/0324626 A1 | 12/2010 | Lefkovitz |
| 2011/0009959 A1 | 1/2011 | Tiedtke |
| 2011/0014189 A1 | 1/2011 | Soula et al. |
| 2011/0022105 A9 | 1/2011 | Owen et al. |
| 2011/0022131 A1 | 1/2011 | Giuliano |
| 2011/0028345 A1 | 2/2011 | Fang et al. |
| 2011/0040204 A1 | 2/2011 | Ivorra et al. |
| 2011/0040349 A1 | 2/2011 | Graupe |
| 2011/0059447 A1 | 3/2011 | Liew |
| 2011/0060266 A1 | 3/2011 | Streeter et al. |
| 2011/0082531 A1 | 4/2011 | Swanson et al. |
| 2011/0092863 A1 | 4/2011 | Kim et al. |
| 2011/0098777 A1 | 4/2011 | Silverstone |
| 2011/0106207 A1 | 5/2011 | Cauller et al. |
| 2011/0106219 A1 | 5/2011 | Cauller et al. |
| 2011/0112352 A1 | 5/2011 | Pilla et al. |
| 2011/0118556 A1 | 5/2011 | Siegel et al. |
| 2011/0124959 A1 | 5/2011 | Murison |
| 2011/0137189 A1 | 6/2011 | Kuo et al. |
| 2011/0158444 A1 | 6/2011 | Waldmann |
| 2011/0177029 A1 | 7/2011 | DeFrees |
| 2011/0184269 A1 | 7/2011 | Sauter-Starace et al. |
| 2011/0190849 A1 | 8/2011 | Faltys |
| 2011/0190882 A1 | 8/2011 | Parker et al. |
| 2011/0195106 A1 | 8/2011 | McMurtrey |
| 2011/0196454 A1 | 8/2011 | Strand et al. |
| 2011/0202120 A1 | 8/2011 | Ball et al. |
| 2011/0208226 A1 | 8/2011 | Fatone et al. |
| 2011/0218593 A1 | 9/2011 | Rubinstein et al. |
| 2011/0224565 A1 | 9/2011 | Ong et al. |
| 2011/0224754 A1 | 9/2011 | Wei |
| 2011/0257501 A1 | 10/2011 | Huys et al. |
| 2011/0257504 A1 | 10/2011 | Hendricks et al. |
| 2011/0262501 A1 | 10/2011 | Webster et al. |
| 2011/0264178 A1 | 10/2011 | Mehregany et al. |
| 2011/0268776 A1 | 11/2011 | Schapira et al. |
| 2011/0270345 A1 | 11/2011 | Johnston et al. |
| 2011/0270361 A1 | 11/2011 | Borsody |
| 2011/0295156 A1 | 12/2011 | Arturi |
| 2011/0301662 A1 | 12/2011 | Bar-Yoseph et al. |
| 2011/0313270 A1 | 12/2011 | Neves et al. |
| 2011/0319703 A1 | 12/2011 | Wiskerke et al. |
| 2012/0016431 A1 | 1/2012 | Paul et al. |
| 2012/0016440 A1 | 1/2012 | Muccio |
| 2012/0022616 A1 | 1/2012 | Garnham et al. |
| 2012/0035684 A1 | 2/2012 | Thompson et al. |
| 2012/0045487 A1 | 2/2012 | Lahann et al. |
| 2012/0046702 A1 | 2/2012 | Gibson |
| 2012/0059389 A1 | 3/2012 | Larson et al. |
| 2012/0064628 A1 | 3/2012 | Blick et al. |
| 2012/0076830 A1 | 3/2012 | Sitharaman et al. |
| 2012/0078327 A1 | 3/2012 | Sloan et al. |
| 2012/0089047 A1 | 4/2012 | Ryba et al. |
| 2012/0095166 A1 | 4/2012 | Ward et al. |
| 2012/0095524 A1 | 4/2012 | Nelson et al. |
| 2012/0101326 A1 | 4/2012 | Simon et al. |
| 2012/0101413 A1 | 4/2012 | Beetel et al. |
| 2012/0109233 A1 | 5/2012 | Lee et al. |
| 2012/0123508 A1 | 5/2012 | Wentz et al. |
| 2012/0124470 A1 | 5/2012 | West et al. |
| 2012/0130360 A1 | 5/2012 | Buckley et al. |
| 2012/0134965 A1 | 5/2012 | Kim et al. |
| 2012/0136232 A1 | 5/2012 | Jeong et al. |
| 2012/0143293 A1 | 6/2012 | Mauch et al. |
| 2012/0158095 A1 | 6/2012 | Jolly |
| 2012/0158104 A1 | 6/2012 | Huynh et al. |
| 2012/0158113 A1 | 6/2012 | Jolly et al. |
| 2012/0158114 A1 | 6/2012 | Debruyne et al. |
| 2012/0179076 A1 | 7/2012 | Bavelier et al. |
| 2012/0185173 A1 | 7/2012 | Yamamoto et al. |
| 2012/0191052 A1 | 7/2012 | Rao |
| 2012/0191086 A1 | 7/2012 | Moll et al. |
| 2012/0197092 A1 | 8/2012 | Luo et al. |
| 2012/0197252 A1 | 8/2012 | Deem et al. |
| 2012/0197374 A1 | 8/2012 | Vogt et al. |
| 2012/0214737 A1 | 8/2012 | Marchionni |
| 2012/0221072 A1 | 8/2012 | Fukamachi et al. |
| 2012/0226331 A1 | 9/2012 | Banna et al. |
| 2012/0237557 A1 | 9/2012 | Lewitus et al. |
| 2012/0238924 A1 | 9/2012 | Avni |
| 2012/0239363 A1 | 9/2012 | Durrani et al. |
| 2012/0244503 A1 | 9/2012 | Neveldine |
| 2012/0245534 A1 | 9/2012 | Jolly |
| 2012/0253236 A1 | 10/2012 | Snow et al. |
| 2012/0259255 A1 | 10/2012 | Tomlinson et al. |
| 2012/0259390 A1 | 10/2012 | Canion |
| 2012/0277825 A1 | 11/2012 | Mawson et al. |
| 2012/0277842 A1 | 11/2012 | Kunis |
| 2012/0282228 A1 | 11/2012 | Bhasin |
| 2012/0283800 A1 | 11/2012 | Perryman et al. |
| 2012/0296191 A1 | 11/2012 | McGrath et al. |
| 2012/0296230 A1 | 11/2012 | Davis et al. |
| 2012/0296444 A1 | 11/2012 | Greenberg et al. |
| 2012/0302856 A1 | 11/2012 | Chang et al. |
| 2012/0310140 A1 | 12/2012 | Kramer et al. |
| 2012/0323288 A1 | 12/2012 | Anderson et al. |
| 2013/0006322 A1 | 1/2013 | Tai |

(56) References Cited

U.S. PATENT DOCUMENTS

| | | |
|---|---|---|
| 2013/0012831 A1 | 1/2013 | Schmitz et al. |
| 2013/0013022 A1* | 1/2013 | De Oliveira Barroso Júnior ........ A61F 5/48 607/41 |
| 2013/0018240 A1 | 1/2013 | McCoy |
| 2013/0018444 A1 | 1/2013 | Glenn et al. |
| 2013/0035745 A1 | 2/2013 | Ahmed et al. |
| 2013/0041432 A1 | 2/2013 | Tucker et al. |
| 2013/0052712 A1 | 2/2013 | Cha et al. |
| 2013/0053853 A1 | 2/2013 | Schmitz et al. |
| 2013/0053934 A1 | 2/2013 | Gluckman et al. |
| 2013/0066147 A1 | 3/2013 | Brown |
| 2013/0066216 A1 | 3/2013 | Park |
| 2013/0066391 A1 | 3/2013 | Hulvershorn et al. |
| 2013/0066392 A1 | 3/2013 | Simon et al. |
| 2013/0066395 A1 | 3/2013 | Simon et al. |
| 2013/0072808 A1 | 3/2013 | Neves et al. |
| 2013/0072835 A1 | 3/2013 | Harry et al. |
| 2013/0090542 A1 | 4/2013 | Kipke et al. |
| 2013/0090711 A1 | 4/2013 | Ramachandran et al. |
| 2013/0101635 A1 | 4/2013 | Park et al. |
| 2013/0116685 A1 | 5/2013 | Deem et al. |
| 2013/0116744 A1 | 5/2013 | Blum et al. |
| 2013/0122528 A1 | 5/2013 | Tyrell et al. |
| 2013/0123568 A1 | 5/2013 | Hamilton et al. |
| 2013/0123570 A1 | 5/2013 | Ly et al. |
| 2013/0131743 A1 | 5/2013 | Yamasaki et al. |
| 2013/0131753 A1 | 5/2013 | Simon et al. |
| 2013/0137955 A1 | 5/2013 | Kong et al. |
| 2013/0144143 A1 | 6/2013 | Kim et al. |
| 2013/0144369 A1 | 6/2013 | Elias et al. |
| 2013/0144370 A1 | 6/2013 | Debruyne et al. |
| 2013/0150653 A1 | 6/2013 | Borsody |
| 2013/0154838 A1 | 6/2013 | Alameh et al. |
| 2013/0157229 A1 | 6/2013 | Lauilzen et al. |
| 2013/0178765 A1 | 7/2013 | Mishelevich |
| 2013/0184792 A1 | 7/2013 | Simon et al. |
| 2013/0184795 A1 | 7/2013 | Kipke et al. |
| 2013/0184799 A1 | 7/2013 | Kipke et al. |
| 2013/0204122 A1 | 8/2013 | Hendler et al. |
| 2013/0204317 A1 | 8/2013 | Sauter-Starace et al. |
| 2013/0210041 A1 | 8/2013 | Anderberg et al. |
| 2013/0218456 A1 | 8/2013 | Zelek et al. |
| 2013/0231725 A1 | 9/2013 | Williams et al. |
| 2013/0238066 A1 | 9/2013 | Joseph et al. |
| 2013/0238074 A1 | 9/2013 | Zimmerling |
| 2013/0245480 A1 | 9/2013 | Crockford |
| 2013/0245486 A1 | 9/2013 | Simon et al. |
| 2013/0245711 A1 | 9/2013 | Simon et al. |
| 2013/0245712 A1 | 9/2013 | Simon et al. |
| 2013/0245717 A1 | 9/2013 | Stohl et al. |
| 2013/0245765 A1 | 9/2013 | Lowry et al. |
| 2013/0248226 A1 | 9/2013 | Sime et al. |
| 2013/0253299 A1 | 9/2013 | Weber et al. |
| 2013/0274540 A1 | 10/2013 | Pilla et al. |
| 2013/0274658 A1 | 10/2013 | Steinke et al. |
| 2013/0274842 A1 | 10/2013 | Gaunt et al. |
| 2013/0280233 A1 | 10/2013 | Kahn et al. |
| 2013/0282001 A1 | 10/2013 | Hezi-Yamit et al. |
| 2013/0282090 A1 | 10/2013 | Decré et al. |
| 2013/0288233 A1 | 10/2013 | Murray |
| 2013/0289659 A1 | 10/2013 | Nelson et al. |
| 2013/0289678 A1 | 10/2013 | Clark et al. |
| 2013/0289686 A1 | 10/2013 | Masson et al. |
| 2013/0296767 A1 | 11/2013 | Zarins et al. |
| 2013/0309278 A1 | 11/2013 | Peyman |
| 2013/0310909 A1 | 11/2013 | Simon et al. |
| 2013/0317400 A1 | 11/2013 | Ferezy |
| 2013/0317580 A1 | 11/2013 | Simon et al. |
| 2013/0324994 A1 | 12/2013 | Pellegrino et al. |
| 2013/0331869 A1 | 12/2013 | Runge et al. |
| 2013/0331910 A1 | 12/2013 | Lamont et al. |
| 2013/0338729 A1 | 12/2013 | Spector |
| 2013/0341185 A1 | 12/2013 | Collaert et al. |
| 2014/0003696 A1 | 1/2014 | Taghva |
| 2014/0018792 A1 | 1/2014 | Gang et al. |
| 2014/0022162 A1 | 1/2014 | Yu et al. |
| 2014/0023999 A1 | 1/2014 | Greder |
| 2014/0024981 A1 | 1/2014 | Chun et al. |
| 2014/0025301 A1 | 1/2014 | Storm et al. |
| 2014/0030735 A1 | 1/2014 | Merali et al. |
| 2014/0046423 A1 | 2/2014 | Rajguru et al. |
| 2014/0051938 A1 | 2/2014 | Goldstein et al. |
| 2014/0058481 A1 | 2/2014 | Perryman et al. |
| 2014/0058483 A1 | 2/2014 | Zao et al. |
| 2014/0066924 A1 | 3/2014 | Azamian et al. |
| 2014/0073883 A1 | 3/2014 | Rao et al. |
| 2014/0074186 A1 | 3/2014 | Faltys et al. |
| 2014/0081682 A1 | 3/2014 | Perlmuter |
| 2014/0094674 A1 | 4/2014 | Nurmikko et al. |
| 2014/0099352 A1 | 4/2014 | Matheny |
| 2014/0107397 A1 | 4/2014 | Simon et al. |
| 2014/0107398 A1 | 4/2014 | Simon et al. |
| 2014/0114168 A1 | 4/2014 | Block et al. |
| 2014/0127171 A1 | 5/2014 | Nocera et al. |
| 2014/0128939 A1 | 5/2014 | Embrey et al. |
| 2014/0135607 A1 | 5/2014 | Lee et al. |
| 2014/0135680 A1 | 5/2014 | Peyman |
| 2014/0142374 A1 | 5/2014 | Makower et al. |
| 2014/0148649 A1 | 5/2014 | Miles et al. |
| 2014/0148871 A1 | 5/2014 | Southwell et al. |
| 2014/0148872 A1 | 5/2014 | Goldwasser et al. |
| 2014/0155811 A1 | 6/2014 | Gibson |
| 2014/0155973 A1 | 6/2014 | Grigsby et al. |
| 2014/0163580 A1 | 6/2014 | Tischendorf et al. |
| 2014/0163641 A1 | 6/2014 | Yao et al. |
| 2014/0163658 A1 | 6/2014 | Faraji et al. |
| 2014/0171807 A1 | 6/2014 | Akkin et al. |
| 2014/0180036 A1 | 6/2014 | Bukkapatnam et al. |
| 2014/0180196 A1 | 6/2014 | Stone et al. |
| 2014/0180365 A1 | 6/2014 | Perryman et al. |
| 2014/0187872 A1 | 7/2014 | Stivoric et al. |
| 2014/0194951 A1 | 7/2014 | Gong et al. |
| 2014/0197937 A1 | 7/2014 | Huang et al. |
| 2014/0200432 A1 | 7/2014 | Banerji et al. |
| 2014/0200466 A1 | 7/2014 | Sereno et al. |
| 2014/0200496 A1 | 7/2014 | Hyde et al. |
| 2014/0200681 A1 | 7/2014 | Kennedy et al. |
| 2014/0206947 A1 | 7/2014 | Isserow et al. |
| 2014/0207292 A1 | 7/2014 | Ramagem et al. |
| 2014/0213842 A1 | 7/2014 | Simon et al. |
| 2014/0213971 A1 | 7/2014 | Dolan et al. |
| 2014/0220555 A1 | 8/2014 | Chen et al. |
| 2014/0222125 A1 | 8/2014 | Glenn et al. |
| 2014/0225763 A1 | 8/2014 | Kavaler et al. |
| 2014/0228901 A1 | 8/2014 | Vogt |
| 2014/0228926 A1 | 8/2014 | Santina et al. |
| 2014/0235950 A1 | 8/2014 | Miles et al. |
| 2014/0236249 A1 | 8/2014 | Rao et al. |
| 2014/0236847 A1 | 8/2014 | Hamilton |
| 2014/0243616 A1 | 8/2014 | Johnson |
| 2014/0243932 A1 | 8/2014 | Libbus et al. |
| 2014/0249395 A1 | 9/2014 | Zhou et al. |
| 2014/0255461 A9 | 9/2014 | McMurtrey |
| 2014/0257063 A1 | 9/2014 | Ong et al. |
| 2014/0257437 A1 | 9/2014 | Simon et al. |
| 2014/0267123 A1 | 9/2014 | Ludwig |
| 2014/0275737 A1 | 9/2014 | Shore et al. |
| 2014/0276718 A1 | 9/2014 | Turovskiy et al. |
| 2014/0276760 A1 | 9/2014 | Bonyak et al. |
| 2014/0277031 A1 | 9/2014 | Ballakur et al. |
| 2014/0277033 A1 | 9/2014 | Taylor et al. |
| 2014/0277220 A1 | 9/2014 | Brennan et al. |
| 2014/0277237 A1 | 9/2014 | Maskara et al. |
| 2014/0277271 A1 | 9/2014 | Chan et al. |
| 2014/0277310 A1 | 9/2014 | Beetel et al. |
| 2014/0277582 A1 | 9/2014 | Leuthardt et al. |
| 2014/0288379 A1 | 9/2014 | Miles et al. |
| 2014/0296646 A1 | 10/2014 | Wingeier et al. |
| 2014/0300490 A1 | 10/2014 | Kotz et al. |
| 2014/0303525 A1 | 10/2014 | Sitharaman |
| 2014/0303548 A1 | 10/2014 | Jolly et al. |
| 2014/0304773 A1 | 10/2014 | Woods et al. |
| 2014/0309548 A1 | 10/2014 | Merz et al. |

(56) References Cited

U.S. PATENT DOCUMENTS

| | | |
|---|---|---|
| 2014/0316398 A1 | 10/2014 | Kelly et al. |
| 2014/0320289 A1 | 10/2014 | Raichman |
| 2014/0324120 A1 | 10/2014 | Bogie et al. |
| 2014/0330337 A1 | 11/2014 | Linke et al. |
| 2014/0336631 A1 | 11/2014 | Wu et al. |
| 2014/0336722 A1 | 11/2014 | Lima et al. |
| 2014/0350041 A1 | 11/2014 | Fun et al. |
| 2014/0350633 A1 | 11/2014 | Gustafson et al. |
| 2014/0357453 A1 | 12/2014 | Tamanaha |
| 2014/0357933 A1 | 12/2014 | Lee et al. |
| 2014/0360511 A1 | 12/2014 | Mohler |
| 2014/0371547 A1 | 12/2014 | Gartenberg et al. |
| 2014/0371564 A1 | 12/2014 | Anikeeva et al. |
| 2014/0371622 A1 | 12/2014 | Hausman et al. |
| 2014/0375457 A1 | 12/2014 | Diaz |
| 2014/0378779 A1 | 12/2014 | Freeman et al. |
| 2014/0378789 A1 | 12/2014 | McKinley et al. |
| 2014/0378946 A1 | 12/2014 | Thompson et al. |
| 2014/0379045 A1 | 12/2014 | Rahimi et al. |
| 2014/0379049 A1 | 12/2014 | Mashiach et al. |
| 2015/0005607 A1 | 1/2015 | Cui et al. |
| 2015/0005680 A1 | 1/2015 | Lipani |
| 2015/0005840 A1 | 1/2015 | Pal et al. |
| 2015/0005841 A1 | 1/2015 | Pal et al. |
| 2015/0005851 A1 | 1/2015 | Bradley |
| 2015/0010607 A1 | 1/2015 | Francis et al. |
| 2015/0012079 A1 | 1/2015 | Goroszeniuk et al. |
| 2015/0016647 A1 | 1/2015 | Martinez et al. |
| 2015/0017140 A1 | 1/2015 | Bhatia et al. |
| 2015/0018659 A1 | 1/2015 | Ware et al. |
| 2015/0032044 A9 | 1/2015 | Peyman |
| 2015/0032178 A1 | 1/2015 | Simon et al. |
| 2015/0032184 A1 | 1/2015 | Muccio |
| 2015/0038886 A1 | 2/2015 | Snow |
| 2015/0039055 A1 | 2/2015 | Wagner et al. |
| 2015/0049325 A1 | 2/2015 | Curtis |
| 2015/0051439 A1 | 2/2015 | Hillbratt et al. |
| 2015/0051684 A1 | 2/2015 | Greenberg et al. |
| 2015/0057736 A1 | 2/2015 | Zachar |
| 2015/0059390 A1 | 3/2015 | Hayes |
| 2015/0062018 A1 | 3/2015 | Naidu et al. |
| 2015/0066126 A1 | 3/2015 | Marx et al. |
| 2015/0067422 A1 | 3/2015 | Hamilton |
| 2015/0073232 A1 | 3/2015 | Ahmad et al. |
| 2015/0073520 A1 | 3/2015 | Strahl et al. |
| 2015/0080709 A1 | 3/2015 | Chaturvedi |
| 2015/0080926 A1 | 3/2015 | Emery |
| 2015/0088030 A1 | 3/2015 | Taylor |
| 2015/0088223 A1 | 3/2015 | Blum et al. |
| 2015/0088224 A1 | 3/2015 | Goldwasser et al. |
| 2015/0088225 A1 | 3/2015 | Noble et al. |
| 2015/0102925 A1 | 4/2015 | Foldyna et al. |
| 2015/0105794 A1 | 4/2015 | Dhanasingh et al. |
| 2015/0105795 A1 | 4/2015 | Lenarz et al. |
| 2015/0112234 A1 | 4/2015 | McCaffrey et al. |
| 2015/0112321 A1 | 4/2015 | Cadouri |
| 2015/0112359 A1 | 4/2015 | Gillbe |
| 2015/0112360 A1 | 4/2015 | Pellinen et al. |
| 2015/0112404 A1 | 4/2015 | Holding et al. |
| 2015/0112405 A1 | 4/2015 | Brown et al. |
| 2015/0112408 A1 | 4/2015 | Kals |
| 2015/0119673 A1 | 4/2015 | Pellinen et al. |
| 2015/0119790 A1 | 4/2015 | Moffitt et al. |
| 2015/0119954 A2 | 4/2015 | Bhadra et al. |
| 2015/0119989 A1 | 4/2015 | Pimenta et al. |
| 2015/0126997 A1 | 5/2015 | Beetel et al. |
| 2015/0133761 A1 | 5/2015 | Vetter et al. |
| 2015/0133956 A1 | 5/2015 | Dayan et al. |
| 2015/0135840 A1 | 5/2015 | Sato et al. |
| 2015/0148643 A1 | 5/2015 | Small et al. |
| 2015/0148644 A1 | 5/2015 | Vaidyanathan et al. |
| 2015/0148736 A1 | 5/2015 | Jolly et al. |
| 2015/0148869 A1 | 5/2015 | Alan et al. |
| 2015/0148878 A1 | 5/2015 | Zoo et al. |
| 2015/0150508 A1 | 6/2015 | Glenn et al. |
| 2015/0157398 A1 | 6/2015 | Zarins et al. |
| 2015/0157851 A1 | 6/2015 | Sefkow et al. |
| 2015/0157854 A1 | 6/2015 | Hetke et al. |
| 2015/0157862 A1 | 6/2015 | Greenberg et al. |
| 2015/0164360 A1 | 6/2015 | Kipke et al. |
| 2015/0164401 A1 | 6/2015 | Toth et al. |
| 2015/0173673 A1 | 6/2015 | Toth et al. |
| 2015/0173918 A1 | 6/2015 | Herr et al. |
| 2015/0174403 A1 | 6/2015 | Pal et al. |
| 2015/0174418 A1 | 6/2015 | Tyler et al. |
| 2015/0182753 A1 | 7/2015 | Harris et al. |
| 2015/0190635 A1 | 7/2015 | Neuvonen et al. |
| 2015/0190636 A1 | 7/2015 | Simon et al. |
| 2015/0190637 A1 | 7/2015 | Simon et al. |
| 2015/0196767 A1 | 7/2015 | Ahmed |
| 2015/0201855 A1 | 7/2015 | Pellinen et al. |
| 2015/0202331 A1 | 7/2015 | Blumenfeld et al. |
| 2015/0202437 A1 | 7/2015 | Franke et al. |
| 2015/0209104 A1 | 7/2015 | Tran et al. |
| 2015/0209577 A1 | 7/2015 | Golestanirad et al. |
| 2015/0209586 A1 | 7/2015 | Silva et al. |
| 2015/0217125 A1 | 8/2015 | Chornenky et al. |
| 2015/0223731 A1 | 8/2015 | Sahin |
| 2015/0224300 A1 | 8/2015 | Hagr et al. |
| 2015/0224330 A1 | 8/2015 | Kaib et al. |
| 2015/0230749 A1 | 8/2015 | Gharib et al. |
| 2015/0231396 A1 | 8/2015 | Burdick et al. |
| 2015/0235529 A1 | 8/2015 | Deschamps |
| 2015/0238104 A1 | 8/2015 | Tass |
| 2015/0238253 A1 | 8/2015 | Wu et al. |
| 2015/0238764 A1 | 8/2015 | Franke |
| 2015/0246072 A1 | 9/2015 | Bhatia et al. |
| 2015/0248470 A1 | 9/2015 | Coleman et al. |
| 2015/0251004 A1 | 9/2015 | Imran et al. |
| 2015/0254992 A1 | 9/2015 | Sethi |
| 2015/0257824 A1 | 9/2015 | Mauch |
| 2015/0272805 A1 | 10/2015 | Burnett et al. |
| 2015/0273206 A1 | 10/2015 | Monteiro |
| 2015/0283365 A1 | 10/2015 | Dacey et al. |
| 2015/0284416 A1 | 10/2015 | Zhao |
| 2015/0290439 A1 | 10/2015 | Eldredge et al. |
| 2015/0290450 A1 | 10/2015 | Kolb et al. |
| 2015/0290464 A1 | 10/2015 | Monteiro |
| 2015/0290472 A1 | 10/2015 | Maguire et al. |
| 2015/0297104 A1 | 10/2015 | Chen et al. |
| 2015/0297444 A1 | 10/2015 | Tass |
| 2015/0297914 A1 | 10/2015 | Hamid et al. |
| 2015/0305667 A1 | 10/2015 | Durand |
| 2015/0305686 A1 | 10/2015 | Coleman et al. |
| 2015/0310762 A1 | 10/2015 | Seim et al. |
| 2015/0313498 A1 | 11/2015 | Coleman et al. |
| 2015/0313512 A1 | 11/2015 | Hausman et al. |
| 2015/0314017 A1 | 11/2015 | Zhao |
| 2015/0320560 A1 | 11/2015 | Mulliken et al. |
| 2015/0320588 A1 | 11/2015 | Connor |
| 2015/0321000 A1 | 11/2015 | Rosenbluth et al. |
| 2015/0321010 A1 | 11/2015 | Marnfeldt |
| 2015/0321017 A1 | 11/2015 | Perryman et al. |
| 2015/0322155 A1 | 11/2015 | Zhao |
| 2015/0328454 A1 | 11/2015 | Lambert |
| 2015/0328455 A1 | 11/2015 | Meadows et al. |
| 2015/0335288 A1 | 11/2015 | Toth et al. |
| 2015/0335876 A1 | 11/2015 | Jeffery et al. |
| 2015/0335877 A1 | 11/2015 | Jeffery et al. |
| 2015/0335883 A1 | 11/2015 | Halpern et al. |
| 2015/0335888 A1 | 11/2015 | Demers et al. |
| 2015/0343196 A1 | 12/2015 | Vasapollo |
| 2015/0343215 A1 | 12/2015 | Ridder |
| 2015/0343242 A1 | 12/2015 | Tyler et al. |
| 2015/0354922 A1 | 12/2015 | Carriere |
| 2015/0359704 A1 | 12/2015 | Imboden et al. |
| 2015/0364018 A1 | 12/2015 | Mirov et al. |
| 2015/0374515 A1 | 12/2015 | Meijer et al. |
| 2015/0379880 A1 | 12/2015 | Sethi |
| 2016/0015962 A1 | 1/2016 | Maragheh et al. |
| 2017/0001003 A1 | 1/2017 | Pivonka et al. |
| 2017/0080216 A1 | 3/2017 | Pham |
| 2017/0209693 A1 | 7/2017 | An et al. |
| 2017/0224990 A1 | 8/2017 | Goldwasser et al. |

(56) References Cited

U.S. PATENT DOCUMENTS

| | | | |
|---|---|---|---|
| 2017/0312512 A1 | 11/2017 | Creasey et al. | |
| 2017/0312526 A1 | 11/2017 | Steinke et al. | |
| 2017/0333695 A1 | 11/2017 | Kaplan et al. | |
| 2018/0116877 A1 | 5/2018 | Ineichen | |
| 2018/0133479 A1 | 5/2018 | Bennett et al. | |
| 2018/0161587 A1 | 6/2018 | Beyer et al. | |
| 2018/0318585 A1 | 11/2018 | Pfeifer | |
| 2019/0357794 A1* | 11/2019 | Bardy | A61B 5/282 |
| 2020/0069941 A1 | 3/2020 | Campean et al. | |
| 2020/0069942 A1 | 3/2020 | Campean et al. | |

FOREIGN PATENT DOCUMENTS

| | | | |
|---|---|---|---|
| EP | 2211977 A1 | 8/2010 | |
| FR | 2646779 B1 | 7/1993 | |
| JP | 2011502707 A | 1/2011 | |
| JP | 2012512682 A | 6/2012 | |
| JP | 2013500080 A | 1/2013 | |
| JP | 2013512076 A | 4/2013 | |
| JP | 2017526496 A | 9/2017 | |
| KR | 100397119 B1 | 9/2003 | |
| KR | 1020140098782 A | 8/2014 | |
| WO | 2009064641 A1 | 5/2009 | |
| WO | 2011011748 A1 | 1/2011 | |
| WO | 2011053607 A1 | 5/2011 | |
| WO | 2012129574 A2 | 9/2012 | |
| WO | 2015183620 A2 | 12/2015 | |
| WO | 2015183620 A3 | 4/2016 | |
| WO | WO-2019094365 A1 * | 5/2019 | A61N 1/025 |
| WO | 2019094365 A9 | 12/2019 | |
| WO | 2020264214 A1 | 12/2020 | |

OTHER PUBLICATIONS

US 8,613,701 B2, 12/2013, Rao et al. (withdrawn)
US 8,652,133 B2, 02/2014, Zarins et al. (withdrawn)
History-Computer (HC). "What is a Real-Time Clock (RTC) and Why are They Important in Computing?" <URL: https://history-computer.com/real-time-clock> (Year: 2022).*
Jarrett, ME; Neuromodulation for constipation and fecal incontinence; Urol Clin North Am; 2005; 79-87; 32.
Jarvis, JC, et al.; Functional electrical stimulation for control of internal organ function; Neuromodulation; 2001; 155-164; 4.
Jesus, LE, et al.; Psychosocial and respiratory disease related to severe bladder dysfunction and non-monosymptomatic enuresis; J Pediatr Urol; 2015;Abstract.
Jezernik, S, et al.; Electrical stimulation for the treatment of bladder dysfunction: current status and future possibilities; Neurol Res; 2002; 413-430; 24;Abstract.
Jiang, CH; Modulation of the micturition reflex pathway by intravesical electrical stimulation: an experimental study in the rat; Neurourol Urodyn; 1998; 543-553; 17.
Jimenez-Toscano, M, et al.; Efficacy and quality of life after transcutaneous posterior tibial neuromodulation for faecal incontinence; Colorectal Dis; 2015; 718-723; 17.
Jin, H, et al.; Electrical neuromodulation at acupoint ST36 normalizes impaired colonic motility induced by rectal distension in dogs; Am J Physiol Gastrointest Liver Physiol; 2015; G368-376; 309.
Johnsen, NV, et al.; The role of electrical stimulation techniques in the management of the male patient with urgency incontinence; Curr Opin Urol; 2014; 560-565; 24.
Johnston, TE, et al.; Implantable FES system for upright mobility and bladder and bowel function for individuals with spinal cord injury; Spinal Cord; 2005; 713-723; 43.
Joussain, C, et al.; Electrical management of neurogenic lower urinary tract disorders; Ann Phys Rehabil Med; 2015; 245-250; 58.
Julius, F, et al.; Catheter tip granuloma associated with sacral region intrathecal drug administration; Neuromodulation; 2003; 225-228; 6.

Kachur, JF, et al.; Neuromodulation of guinea pig intestinal electrolyte transport by cholecystokinin octapeptide; Gastroenterology; 1991; 344-349; 100;Abstract.
Kacker, R, et al.; Electrical and mechanical office-based neuromodulation; Urol Clin North Am; 2013; 581-589; 40.
Kacker, R, et al.; Selection of ideal candidates for neuromodulation in refractory overactive bladder; Curr Urol Rep; 2010; 372-378; 11.
Kantartzis, K, et al.; Sacral neuromodulation and intravesical botulinum toxin for refractory overactive bladder; Curr Opin Obstet Gynecol; 2012; 331-336; 24.
Kantartzis, KL, et al.; Cost-effectiveness of test phase implantation strategies for InterStim(R) sacral neuromodulation; Female Pelvic Med Reconstr Surg; 2013; 322-327; 19;Abstract.
Kapoor, DS, et al.; Combined urinary and faecal incontinence; Int Urogynecol J Pelvic Floor Dysfunct; 2005; 321-328; 16.
Karademir, K, et al.; A peripheric neuromodulation technique for curing detrusor overactivity: Stoller afferent neurostimulation; Scand J Urol Nephrol; 2005; 230-233; 39.
Karam, R, et al.; Real-Time Classification of Bladder Events for Effective Diagnosis and Treatment of Urinary Incontinence; IEEE Trans Biomed Eng; 2015.
Karmarkar, R, et al.; Emerging drugs for overactive bladder; Expert Opin Emerg Drugs; 2015; 613-624; 20;Abstracl.
Karram, MM; Sacral neuromodulation: emerging technology with expanding indications; Int Urogynecol J; 2010; 1443; 21.
Karsenty, G, et al.; Botulinum toxin type a injections into the trigone to treat idiopathic overactive bladder do not induce vesicoureteral reflux; J Urol; 2007; 1011-1014; 177.
Karsenty, G, et al.; Understanding detrusor sphincter dyssynergia—significance of chronology; Urology; 2005; 763-768; 66.
Katsuragi, T, et al.; Cholinergic neuromodulation by ATP, adenosine and its N6-substituted analogues in guinea-pig ileum; Clin Exp Pharmacol Physiol; 1985; 73-78; 12;Abstract.
Katsuragi, T, et al.; Involvement of dihydropyridine-sensitive Ca2+ channels in adenosine-evoked inhibition of acetylcholine release from guinea pig ileal preparation; J Neurochem; 1990; 363-369; 55.
Katsuragi, T, et al.; Possible transsynaptic cholinergic neuromodulation by ATP released from ileal longitudinal muscles of guinea pigs; Life Sci; 1993; 911-918; 53.
Kaufmann, S, et al.; Unilateral vs bilateral sacral neuromodulation in pigs with formalin-induced detrusor hyperactivity; BJU Int; 2009; 260-263; 103.
Kavia, R, et al.; A functional magnetic resonance imaging study of the effect of sacral neuromodulation on brain responses in women with Fowler's syndrome; BJU Int; 2010; 366-372; 105.
Kavia, R, et al.; Overactive bladder; J R Soc Promot Health; 2005; 176-179; 125;Abstract.
Kenefick, NJ; Sacral nerve neuromodulation for the treatment of lower bowel motility disorders; Ann R Coll Surg Engl; 2006; 617-623; 88.
Keppene, V, et al.; [Neuromodulation in the management of neurogenic lower urinary tract dysfunction]; Prog Urol; 2007; 609-615; 17;Abstract.
Kessler, TM, et al.; [Sacral neuromodulation for neurogenic bladder dysfunction]; Urologe A; 2012; 179-183; 51.
Kessler, TM, et al.; [Urodynamic phenomena in the aging bladder]; Urologe A; 2004; 542-546; 43.
Kessler, TM, et al.; Prolonged sacral neuromodulation testing using permanent leads: a more reliable patient selection method?; Eur Urol; 2005; 660-665; 47.
Kessler, TM, et al.; Sacral neuromodulation for refractory lower urinary tract dysfunction: results of a nationwide registry in Switzerland; Eur Urol; 2007; 1357-1363; 51.
Kessler, TM, et al.; Urologists' referral attitude for sacral neuromodulation for treating refractory idiopathic overactive bladder syndrome: discrete choice experiment; Neurourol Urodyn; 2014; 1240-1246; 33.
Killinger, KA, et al.; Secondary changes in bowel function after successful treatment of voiding symptoms with neuromodulation; Neurourol Urodyn; 2011; 133-137; 30.
Kim, JH, et al.; Sacral nerve stimulation for treatment of intractable pain associated with cauda equina syndrome; J Korean Neurosurg Soc; 2010; 473-476; 47.

(56) References Cited

OTHER PUBLICATIONS

Kinder, MV, et al.; Neuronal circuitry of the lower urinary tract; central and peripheral neuronal control of the micturition cycle; Anat Embryol (Berl); 1995; 195-209; 192.

Kirkham, AP, et al.; Neuromodulation through sacral nerve roots 2 to 4 with a Finetech-Brindley sacral posterior and anterior root stimulator; Spinal Cord; 2002; 272-281; 40.

Kirkham, AP, et al.; The acute effects of continuous and conditional neuromodulation on the bladder in spinal cord injury; Spinal Cord; 2001; 420-428; 39.

Klingler, HC, et al.; Use of peripheral neuromodulation of the S3 region for treatment of detrusor overactivity: a urodynamic-based study; Urology; 2000; 766-771; 56.

Knowles, CH, et al.; Percutaneous tibial nerve stimulation versus sham electrical stimulation for the treatment of faecal incontinence in adults (CONFIDeNT): a double-blind, multicentre, pragmatic, parallel-group, randomised controlled trial; Lancet; 2015; 1640-1648; 386.

Knupfer, S, et al.; [Therapy-refractory overactive bladder: alternative treatment approaches]; Urologe A; 2011; 806-809; 50.

Knupfer, SC, et al.; Protocol for a randomized, placebo-controlled, double-blind clinical trial investigating sacral Teuromodulation for neurogenic lower urinary tract dysfunction; BMC Urol; 2014; 65; 14.

Kocjancic, E, et al.; Sacral neuromodulation for urinary retention in a kidney-transplant patient; Urol Int; 2005; 187-188; 75.

Kohli, N, et al.; InterStim Therapy: A Contemporary Approach to Overactive Bladder; Rev Obstet Gynecol; 2009; 18-27; 2.

Kohli, N, et al.; Neuromodulation techniques for the treatment of the overactive bladder; Clin Obstet Gynecol; 2002; 218-232; 45.

Koldewijn, EL; [What to do if pills do not work for urge incontinence—still many questions and ambiguities]; Ned Tijdschr Geneeskd; 2012; A5099; 156;Abstract.

Kosan, M, et al.; Alteration in contractile responses in human detrusor smooth muscle from obstructed bladders with overactivity; Urol Int; 2008; 193-200; 80.

[No Author Listed]. 3V Lithium Button Cells. Engineering Specifications. Renata Batteries, Dec. 2010. 3 pages.

[No Author Listed]. Energizer CR2032 Lithium Coin. Product Datasheet. Energizer. 1 page.

[No Author Listed]. Lithium Battery Model CR2032. Specification. Omnergy, 9 pages.

[No Author Listed]. Lithium Manganese Dioxide Battery CR2032. Data Sheet. Hitachi Maxell Ltd, Nov. 2008. 1 page.

[No Author Listed]. Manganese Dioxide Coin Batteries. Individual Specifications. Panasonic, Aug. 2005. 1 page.

[No Author Listed]. nRF5 SDK v15.0.0. Documentation. Nordic Semiconductor, 2018. 15 pages. URL: https://infocenter.nordicsemi.com/index.jsp?topic=%2Fcom.nordic.infocenter.sdk5.v15.0.0%2Findex.html [last accessed May 2, 2022].

[No Author Listed]. S132 SoftDevice v6.1. Specification. Nordic Semiconductor, Aug. 2018. 114 pages.

Furset, K, et al.; High Pulse Drain Impact on CR2032 Coin Cell Battery Capacity; 2011.

ISR issued in international application No. PCT/US2022/014004, dated May 11, 2022.

Bernstein, AJ, et al.; Expanding indications for neuromodulation; Urol Clin North Am; 2005; 59-63; 32.

Bertapelle, MP, et al.; Sacral neuromodulation and Botulinum toxin A for refractory idiopathic overactive bladder: a cost-utility analysis in the perspective of Italian Healthcare System; World J Urol; 2015; 1109-1117; 33.

Beusterien, K, et al.; Use of best-worst scaling to assess patient perceptions of treatments for refractory overactive bladder; Neurourol Urodyn; 2015;Abstract.

Biemans, JM, et al.; Efficacy and effectiveness of percutaneous tibial nerve stimulation in the treatment of pelvic argan disorders: a systematic review; Neuromodulation; 2013; 25-33; discussion 33; 16.

Bleier, JI, et al.; Surgical management of fecal incontinence; Gastroenterol Clin North Am; 2013; 815-836; 42.

Blok, BF, et al.; Different brain effects during chronic and acute sacral neuromodulation in urge incontinent patients with implanted neurostimulators; BJU Int; 2006; 1238-1243; 98.

Bolton, JF, et al.; Neuromodulation 10 years on: how widely should we use this technique in bladder dysfunction? Curr Opin Urol; 2009; 375-379; 19.

Bosch, JL, et al.; Neuromodulation: urodynamic effects of sacral (S3) spinal nerve stimulation in patients with detrusor instability or detrusor hyperflexia; Behav Brain Res; 1998; 141-150; 92.

Bosch, JL, et al.; Sacral nerve neuromodulation in the treatment of patients with refractory motor urge incontinence ong-term results of a prospective longitudinal study; J Urol; 2000; 1219-1222; 163.

Bosch, JL, et al.; What treatment should we use if drugs fail for OAB; and, what really works after drugs?; Neurourol Urodyn; 2010; 658-661; 29.

Bosch, JL; An update on sacral neuromodulation: where do we stand with this in the management of lower urinary tract dysfunction in 2010?; BJU Int; 2010; 1432-1442; 106.

Bosch, JL; Sacral neuromodulation in the treatment of the unstable bladder; Curr Opin Urol; 1998; 287-291; 8.

Bosch, JL; Sacral neuromodulation: treatment success is not just a matter of optimal electrode position; BJU Int; 2000; 20-21; discussion 22-23; 85 Suppl 3.

Bouchelouche, K, et al.; Recent developments in the management of interstitial cystitis; Curr Opin Urol; 2003; 309-313; 13.

Bouguen, G, et al.; Effects of transcutaneous tibial nerve stimulation on anorectal physiology in fecal incontinence: a double-blind placebo-controlled cross-over evaluation; Neurogastroenterol Motil; 2014; 247-254; 26.

Bower, WF, et al.; A pilot study of the home application of transcutaneous neuromodulation in children with urgency ar urge incontinence; J Urol; 2001; 2420-2422; 166.

Bower, WF, et al.; A review of non-invasive electro neuromodulation as an intervention for non-neurogenic bladder Jysfunction in children; Neurourol Urodyn; 2004; 63-67; 23.

Bower, WF, et al.; A urodynamic study of surface neuromodulation versus sham in detrusor instability and sensory urgency; J Urol; 1998; 2133-2136; 160.

Braun, PM, et al.; [Chronic sacral bilateral neuromodulation. Using a minimal invasive implantation technique in patients with disorders of bladder function]; Urologe A; 2002; 44-47; 41.

Braun, PM, et al.; Alterations of cortical electrical activity in patients with sacral neuromodulator; Eur Urol; 2002; 562-566; discussion 566-567; 41.

Braun, PM, et al.; Stimulation signal modification in a porcine model for suppression of unstable detrusor contractions; Urology; 2003; 839-844; 61.

Braun, PM, et al.; Tailored laminectomy: a new technique for neuromodulator implantation; J Urol; 1999; 1607-1609; 162.

Brink, TS, et al.; A Chronic, Conscious Large Animal Platform to Quantify Therapeutic Effects of Sacral Neuromodulation on Bladder Function; J Urol; 2015; 252-258; 194.

Bristow, SE, et al.; TENS: a treatment option for bladder dysfunction; Int Urogynecol J Pelvic Floor Dysfunct; 1996; 185-190; 7.

Brooks, DR, et al.; The Caenorhabditis elegans orthologue of mammalian puromycin-sensitive aminopeptidase has roles in embryogenesis and reproduction; J Biol Chem; 2003; 42795-42801; 278.

Brosa, M, et al.; Cost-effectiveness analysis of sacral neuromodulation (SNM) with Interstim for fecal incontinence patients in Spain; Curr Med Res Opin; 2008; 907-918; 24.

Bross, S, et al.; [Sacral neuromodulation in patients with nonobstructive, chronic urinary retention: relevance of the carbachol test and influence of associated nerve lession]; Aktuelle Urol; 2003; 157-161; 34;Abstract.

Bross, S, et al.; The role of the carbachol test and concomitant diseases in patients with nonobstructive urinary retention undergoing sacral neuromodulation; World J Urol; 2003; 346-349; 20.

Brouwer, R, et al.; Sacral nerve neuromodulation is effective treatment for fecal incontinence in the presence of a sphincter

(56) References Cited

OTHER PUBLICATIONS defect, pudendal neuropathy, or previous sphincter repair; Dis Colon Rectum; 2010; 273-278; 53.
Brown, DR, et al.; Delta-opioid receptor mRNA expression and immunohistochemical localization in porcine ileum; Dig Dis Sci; 1998; 1402-1410; 43.
Brown, ET, et al.; New evidence in the treatment of overactive bladder; Curr Opin Obstet Gynecol; 2015; 366-372; 27.
Brown, SR, et al.; Surgery for faecal incontinence in adults; Cochrane Database Syst Rev; 2013; Cd001757; 7.
Buback, D; The use of neuromodulation for treatment of urinary incontinence; Aorn j; 2001; 176-178, 181-177, 189-190; quiz 191-176; 73;Abstract.
Bugbee, M, et al.; An implant for chronic selective stimulation of nerves; Med Eng Phys; 2001; 29-36; 23.
Buhmann, H, et al.; [Update on fecal incontinence]; Praxis (Bern 1994); 2014; 1313-1321; 103.
Burks, FN, et al.; Neuromodulation and the neurogenic bladder; Urol Clin North Am; 2010; 559-565; 37.
Burks, FN, et al.; Neuromodulation versus medication for overactive bladder: the case for early intervention; Curr Urol Rep; 2009; 342-346; 10.
Burnstock, G, et al.; P2X receptors in health and disease; Adv Pharmacol; 2011; 333-372; 61;Abstract.
Burnstock, G; Innervation of bladder and bowel; Ciba Found Symp; 1990; 2-18; discussion 18-26; 151;Abstract.
Burnstock, G; Introduction and perspective, historical note; Front Cell Neurosci; 2013; 227; 7.
Burnstock, G; Introductory overview of purinergic signalling; Front Biosci (Elite Ed); 2011; 896-900; 3;Abstract.
Burnstock, G; Purinergic cotransmission; F1000 Biol Rep; 2009; 46; 1.
Burnstock, G; Purinergic signalling in the gastrointestinal tract and related organs in health and disease; Purinergic Signal; 2014; 18323; 10.
Burnstock, G; Purinergic signalling: Its unpopular beginning, its acceptance and its exciting future; Bioessays; 2012; 218-225; 34.
Burnstock, G; Purinergic signalling: past, present and future; Braz J Med Biol Res; 2009; 42437; 42.
Burnstock, G; The journey to establish purinergic signalling in the gut; Neurogastroenterol Motil; 2008; 42601; 20 Suppl 1.
Cadish, LA, et al.; Stimulation latency and comparison of cycling regimens in women using sacral neuromodulation; Neurourol Urodyn; 2016;Abstract.
Cameron, AP, et al.; Battery explantation after sacral neuromodulation in the Medicare population; Neurourol Urodyn; 2013; 238-241; 32.
Campbell, JD, et al.; Treatment success for overactive bladder with urinary urge incontinence refractory to oral antimuscarinics: a review of published evidence; BMC Urol; 2009; 18; 9.
Campin, L, et al.; [Urinary functional disorders bound to deep endometriosis and to its treatment: review of the literature]; J Gynecol Obstet Biol Reprod (Paris); 2014; 431-442; 43;Abstract.
Peters, KM, et al.; Effect of Sacral Neuromodulation on Outcome Measures and Urine Chemokines in Interstitial Cystitis/Painful Bladder Syndrome Patients; Low Urin Tract Symptoms; 2015; 77-83; 7.
Peters, KM, et al.; Effect of Sacral Neuromodulation Rate on Overactive Bladder Symptoms: A Randomized Crossover Feasibility Study; Low Urin Tract Symptoms; 2013; 129-133; 5.
Peters, KM, et al.; Is sensory testing during lead placement crucial for achieving positive outcomes after sacral neuromodulation?; Neurourol Urodyn; 2011; 1489-1492; 30.
Peters, KM, et al.; Percutaneous tibial nerve stimulation for the long-term treatment of overactive bladder: 3-year results of the STEP study; J Urol; 2013; 2194-2201; 189.
Peters, KM, et al.; Predictors of reoperation after sacral neuromodulation: A single institution evaluation of over 400 patients; Neurourol Urodyn; 2015;Abstract.
Peters, KM, et al.; Randomized trial of percutaneous tibial nerve stimulation versus Sham efficacy in the treatment of overactive bladder syndrome: results from the SUmiT trial; J Urol; 2010; 1438-1443; 183.
Peters, KM; Alternative approaches to sacral nerve stimulation; Int Urogynecol J; 2010; 1559-1563; 21.
Peters, KM; Sacral neuromodulation is an effective treatment for interstitial cystitis/bladder pain syndrome: pro; J Urol; 2012; 2043-2044; 188.
Pettit, PD, et al.; Sacral neuromodulation: new applications in the treatment of female pelvic floor dysfunction; Curr Opin Obstet Gynecol; 2002; 521-525; 14.
Peyronnet, B, et al.; [Management of overactive bladder in women]; Prog Urol; 2015; 877-883; 25;Abstract.
Phe, V, et al.; How to define a refractory idiopathic overactive bladder?; Neurourol Urodyn; 2015; 42411; 34.
Possover, M, et al.; Neuromodulation of the superior hypogastric plexus: a new option to treat bladder atonia secondary to radical pelvic surgery?; Surg Neurol; 2009; 573-576; 72.
Possover, M, et al.; Risks, symptoms, and management of pelvic nerve damage secondary to surgery for pelvic organ prolapse: a report of 95 cases; Int Urogynecol J; 2011; 1485-1490; 22.
Possover, M; A novel implantation technique for pudendal nerve stimulation for treatment of overactive bladder and urgency incontinence; J Minim Invasive Gynecol; 2014; 888-892; 21.
Possover, M; Laparoscopic management of endopelvic etiologies of pudendal pain in 134 consecutive patients; J Urol; 2009; 1732-1736; 181.
Possover, M; The laparoscopic implantation of neuroprothesis to the sacral plexus for therapy of neurogenic Madder dysfunctions after failure of percutaneous sacral nerve stimulation; Neuromodulation; 2010; 141-144; 13.
Possover, M; The sacral LION procedure for recovery of bladder/rectum/sexual functions in paraplegic patients after explantation of a previous Finetech-Brindley controller; J Minim Invasive Gynecol; 2009; 98-101; 16.
Powell, CR, et al.; Long-term outcomes of urgency-frequency syndrome due to painful bladder syndrome treated with sacral neuromodulation and analysis of failures; J Urol; 2010; 173-176; 183.
Pucciani, F; A review on functional results of sphincter-saving surgery for rectal cancer: the anterior resection syndrome; Updates Surg; 2013; 257-263; 65.
Puccini, F, et al.; Sacral neuromodulation: an effective treatment for lower urinary tract symptoms in multiple sclerosis; Int Urogynecol J; 2016; 347-354; 27.
Qin, C, et al.; Is constant current or constant voltage spinal cord stimulation superior for the suppression of nociceptive visceral and somatic stimuli? A rat model; Neuromodulation; 2012; 132-142; discussion 143; 15.
Rahnama'i, MS, et al.; Evidence for prostaglandin E2 receptor expression in the intramural ganglia of the guinea pig urinary bladder; J Chem Neuroanat; 2015; 43-47; 64-65.
Rai, BP, et al.; Anticholinergic drugs versus non-drug active therapies for non-neurogenic overactive bladder syndrome in adults; Cochrane Database Syst Rev; 2012; Cd003193; 12;Abstract.
Ramage, L, et al.; A systematic review of sacral nerve stimulation for low anterior resection syndrome; Colorectal Dis; 2015; 762-771; 17.
Ramundo, JM, et al.; State of the science: pathology and management of the patient with overactive bladder; Ostomy Wound Manage; 2002; 22-27; 48.
Rana, MV, et al.; Tripolar spinal cord stimulation for the treatment of abdominal pain associated with irritable bowel syndrome; Neuromodulation; 2013; 73-77; discussion 77; 16.
Rashid, TG, et al.; Male incontinence: onabotulinum toxin A and sacral nerve stimulation; Curr Opin Urol; 2013; 545-551; 23.
Rasmussen, NT, et al.; Successful use of sacral neuromodulation after failed bladder augmentation; Can Urol Assoc J; 2009; E49-50; 3.
Ratto, C, et al.; Minimally invasive sacral neuromodulation implant technique: modifications to the conventional procedure; Dis Colon Rectum; 2003; 414-417; 46.

(56) References Cited

OTHER PUBLICATIONS

Ratto, C, et al.; Sacral neuromodulation in the treatment of defecation disorders; Acta Neurochir Suppl; 2007; 341-350; 97;Abstract.
Rawashdeh, YF, et al.; International Children's Continence Society's recommendations for therapeutic intervention in congenital neuropathic bladder and bowel dysfunction in children; Neurourol Urodyn; 2012; 615-620; 31.
Reese, JN, et al.; Role of spinal metabotropic glutamate receptor 5 in pudendal inhibition of the nociceptive bladder reflex in cats; Am J Physiol Renal Physiol; 2015; F832-838; 308.
Reitz, A, et al.; Topographic anatomy of a new posterior approach to the pudendal nerve for stimulation; Eur Urol; 2007; 1350-1355; discussion 1355-1356; 51.
Reyblat, P, et al.; Augmentation enterocystoplasty in overactive bladder: is there still a role?; Curr Urol Rep; 2010; 132-439; 11.
Riazimand, SH, et al.; A rat model for studying effects of sacral neuromodulation on the contractile activity of a chronically inflamed bladder; BJU Int; 2004; 158-163; 94.
Riazimand, SH, et al.; Interaction between neurotransmitter antagonists and effects of sacral neuromodulation in rats with chronically hyperactive bladder; BJU Int; 2005; 900-908; 96.
Richter, EO, et al.; Percutaneous cephalocaudal implantation of epidural stimulation electrodes over sacral nerve roots—a technical note on the importance of the lateral approach; Neuromodulation; 2011; 62-67; discussion 67; 14.
Ridout, AE, et al.; Tibial nerve stimulation for overactive bladder syndrome unresponsive to medical therapy; J Obstet Gynaecol; 2010; 111-114; 30.
Rigaud, J, et al.; [Specific treatments for painful bladder syndrome]; Prog Urol; 2010; 1044-1053; 20;Abstract.
Rimmer, CJ, et al.; Short-term Outcomes of a Randomized Pilot Trial of 2 Treatment Regimens of Transcutaneous Tibial Nerve Stimulation for Fecal Incontinence; Dis Colon Rectum; 2015; 974-982; 58.
Ripetti, V, et al.; Sacral nerve neuromodulation improves physical, psychological and social quality of life in patients with fecal incontinence; Tech Coloproctol; 2002; 147-152; 6.
Rittenmeyer, H; Sacral nerve neuromodulation (InterStim). Part I: Review of the InterStim system; Urol Nurs; 2008; 15-20; 28.
Robaina Padron, FJ; [Surgical neuromodulation: new frontiers in neurosurgery]; Neurocirugia (Astur); 2008; 143-155; 19;Abstract.
Robinson, D, et al.; Overactive bladder: diagnosis and management; Maturitas; 2012; 188-193; 71.
Robinson, D, et al.; The management of overactive bladder refractory to medical therapy; Maturitas; 2013; 101-104; 75.
Robinson, D, et al.; The medical management of refractory overactive bladder; Maturitas; 2013; 386-390; 74.
Rogers, MJ, et al.; Propranolol, but not naloxone, enhances spinal reflex bladder activity and reduces pudendal inhibition in cats; Am J Physiol Regul Integr Comp Physiol; 2015; R42-49; 308.
Rogers, MJ, et al.; Role of glycine in nociceptive and non-nociceptive bladder reflexes and pudendal afferent inhibition of these reflexes in cats; Neurourol Urodyn; 2015;Abstract.
Romero Maroto, J, et al.; [Techniques and current practice of urodynamics. Problems and traps]; Aetas Urol Esp; 2003; 75-91; 27;Abstract.
Roth, TM; Blunt trauma leading to delayed extrusion of sacral nerve implant; Int Urogynecol J Pelvic Floor Dysfunct; 2009; 735-737; 20.
Findlay, JM, et al.; Peripheral neuromodulation via posterior tibial nerve stimulation—a potential treatment for faecal ncontinence?; Ann R Coll Surg Engl; 2010; 385-390; 92.
Firoozi, F, et al.; Increasing patient preparedness for sacral neuromodulation improves patient reported outcomes despite leaving objective measures of success unchanged; J Urol; 2013; 594-597; 190.
Fjorback, MV, et al.; A portable device for experimental treatment of neurogenic detrusor overactivity; Neuromodulation; 2003; 158-165; 6.
Foditsch, EE, et al.; Laparoscopic placement of a tined lead electrode on the pudendal nerve with urodynamic monitoring of bladder function during electrical stimulation: an acute experimental study in healthy female pigs; Springerplus; 2014; 309; 3.
Foon, R, et al.; The overactive bladder; Ther Adv Urol; 2010; 147-155; 2.
Ford, AP, et al.; P2X3 receptors and sensitization of autonomic reflexes; Auton Neurosci; 2015; 16-24; 191.
Fowler, CJ; The perspective of a neurologist on treatment-related research in fecal and urinary incontinence; Gastroenterology; 2004; S172-174; 126.
Franzen, K, et al.; Surgery for urinary incontinence in women 65 years and older: a systematic review; Int Urogynecol J; 2015; 1095-1102; 26.
Fraser, MO, et al.; Neural control of the urethra and development of pharmacotherapy for stress urinary incontinence; BJU Int; 2003; 743-748; 91.
Freeman, RM, et al.; Overactive bladder; Best Pract Res Clin Obstet Gynaecol; 2005; 829-841; 19.
French, JS, et al.; What do spinal cord injury consumers want? A review of spinal cord injury consumer priorities and neuroprosthesis from the 2008 neural interfaces conference; Neuromodulalion; 2010; 229-231; 13.
Frokjaer, JB, et al.; Modulation of vagal tone enhances gastroduodenal motility and reduces somatic pain sensitivity; Neurogastroenterol Motil; 2016.
Fu, G, et al.; [Neuromodulation for treatment for neurogenic bowel dysfunction]; Zhonghua Wai Ke Za Zhi; 2009; 128-131; 47.
Gaj, F, et al.; [Chronic pelvic pain treatment with posterior tibial nerve stimulation]; Clin Ter; 2011; e111-114; 162; Abstract.
Gajewski, JB, et al.; The long-term efficacy of sacral neuromodulation in the management of intractable cases of bladder pain syndrome: 14 years of experience in one centre; BJU Int; 2011; 1258-1264; 107.
Game, X, et al.; [Alternative treatments for interstitial cystitis]; Prog Urol; 2009; 357-363; 19;Abstract.
Game, X, et al.; Outcome after treatment of detrusor-sphincter dyssynergia by temporary stent; Spinal Cord; 2008; 74-77; 46.
Game, X; [Sacral neuromodulation and sexuality]; Prog Urol; 2008; 167; 18;Abstract.
Ganio, E, et al.; Neuromodulation for fecal incontinence: outcome in 16 patients with definitive implant. The initial Italian Sacral Neurostimulation Group (GINS) experience; Dis Colon Rectum; 2001; 965-970; 44.
George, E, et al.; Use of combined anticholinergic medication and sacral neuromodulation in the treatment of refractory overactive bladder; Female Pelvic Med Reconstr Surg; 2011; 97-99; 17;Abstract.
Ghazwani, YQ, et al.; Efficacy of sacral neuromodulation in treatment of bladder pain syndrome: long-term follow-up; Neurourol Urodyn; 2011; 1271-1275; 30.
Ghiselli, R, et al.; Nitric oxide synthase expression in rat anorectal tissue after sacral neuromodulation; J Surg Res; 2012; 29-33; 176.
Giarenis, I, et al.; Management of refractory overactive bladder; Minerva Ginecol; 2013; 41-52; 65;Abstract.
Giarenis, I, et al.; Managing urinary incontinence: what works?; Climacteric; 2014; 26-33; 17 Suppl 2;Abstract.
Gibbons, SJ, et al.; Review article: carbon monoxide in gastrointestinal physiology and its potential in therapeutics; Aliment Pharmacol Ther; 2013; 689-702; 38.
Gill, BC, et al.; Improved sexual and urinary function in women with sacral nerve stimulation; Neuromodulation; 2011; 436-443; discussion 443; 14.
Gill, BC, et al.; Improvement of bowel dysfunction with sacral neuromodulation for refractory urge urinary incontinence; Int Urogynecol J; 2012; 735-741; 23.
Gleason, JL, et al.; Sacral neuromodulation effects on periurethral sensation and urethral sphincter activity; Neurourol Urodyn; 2013; 476-479; 32.
Glinski, RW, et al.; Refractory overactive bladder: Beyond oral anticholinergic therapy; Indian J Urol; 2007; 166-173; 23.
Gonzalez-Chamorro, F, et al.; [Current status of neurostimulation and neuromodulation for vesicourethral dysfunction]; Arch Esp Urol; 1997; 687-694; 50;Abstract.

(56) References Cited

OTHER PUBLICATIONS

Gonzalez-Chamorro, F, et al.; [Neurostimulation and neuromodulation in urinary incontinence]; Rev Med Univ Navarra; 2004; 75-84; 48;Abstract.
Gormley, EA, et al.; Diagnosis and treatment of overactive bladder (non-neurogenic) in adults: AUA/SUFU guideline amendment; J Urol; 2015; 1572-1580; 193.
Gottwald, T, et al.; [Sex differences in neuromodulation of mucosal mast cells in the rat jejunum]; Langenbecks Arch Chir; 1997; 157-163; 382;Abstract.
Govaert, B, et al.; Neuromodulation for functional bowel disorders; Best Pract Res Clin Gastroenterol; 2009; 545-553; 23.
Govier, FE, et al.; Percutaneous afferent neuromodulation for the refractory overactive bladder: results of a multicenter study; J Urol; 2001; 1193-1198; 165.
Green, BT, et al.; Neuromodulation of enteropathogen internalization in Peyer's patches from porcine jejunum; J Neuroimmunol; 2003; 74-82; 141.
Griffin, KM, et al.; Sacral nerve stimulation increases activation of the primary somatosensory cortex by anal canal stimulation in an experimental model; Br J Surg; 2011; 1160-1169; 98.
Grill, WM; Electrical activation of spinal neural circuits: application to motor-system neural prostheses; Neuromodulation; 2000; 97-106; 3.
Groen, J, et al.; Chronic pudendal nerve neuromodulation in women with idiopathic refractory detrusor overactivity incontinence: results of a pilot study with a novel minimally invasive implantable mini-stimulator; Neurourol Urodyn; 2005; 226-230; 24.
Groen, J, et al.; Computerized assessment of detrusor instability in patients treated with sacral neuromodulation; J Urol; 2001; 169-173; 165.
Groen, J, et al.; Neuromodulation techniques in the treatment of the overactive bladder; BJU Int; 2001; 723-731; 87.
Groen, J, et al.; Sacral neuromodulation in women with idiopathic detrusor overactivity incontinence: decreased overactivity but unchanged bladder contraction strength and urethral resistance during voiding; J Urol; 2006; 1005-1009; discussion 1009; 175.
Groen, LA, et al.; Sacral neuromodulation with an implantable pulse generator in children with lower urinary tract symptoms: 15-year experience; J Urol; 2012; 1313-1317; 188.
Groenendijk, PM, et al.; Five-Year Follow-up After Sacral Neuromodulation: Single Center Experience; Neuromodulation; 2007; 363-368; 10.
Groenendijk, PM, et al.; Urodynamic evaluation of sacral neuromodulation for urge urinary incontinence; BJU Int; 2008; 325-329; 101.
Gross, T, et al.; Transcutaneous Electrical Nerve Stimulation for Treating Neurogenic Lower Urinary Tract Dysfunction: A Systematic Review; Eur Urol; 2016;Abstract.
Grossi, U, et al.; Sacral neuromodulation for anorectal dysfunction secondary to congenital imperforate anus: report of two cases; Int J Colorectal Dis; 2014; 889-890; 29.
Grunewald, V; Neuromodulation/neurostimulation; World J Urol; 1998; 299-300; 16.
Guerci, B, et al.; Gastric electrical stimulation for the treatment of diabetic gastroparesis; Diabetes Metab; 2012; 393-402; 38.
Gulur, DM, et al.; Management of overactive bladder; Nat Rev Urol; 2010; 572-582; 7.
Nambiar, A, et al.; Chapter 4: Guidelines for the diagnosis and treatment of overactive bladder (OAB) and neurogenic detrusor overactivity (NDO); Neurourol Urodyn; 2014; S21-25; 33 Suppl 3.
Natalin, R, et al.; Management of OAB in those over age 65; Curr Urol Rep; 2013; 379-385; 14.
Ng, CK, et al.; Refractory overactive bladder in men: update on novel therapies; Curr Urol Rep; 2006; 456-461; 7.
Nijman, RJ; Classification and treatment of functional incontinence in children; BJU Int; 2000; 37-42; discussion 45-36; 85 Suppl 3.
Nijman, RJ; Role of antimuscarinics in the treatment of non-neurogenic daytime urinary incontinence in children; Urology; 2004; 45-50; 63.
Nilsson, KF, et al.; Estimation of endogenous adenosine activity at adenosine receptors in guinea-pig ileum using a new pharmacological method; Acta Physiol (Oxf); 2010; 231-241; 199.
Nitti, VW; Urodynamics, Incontinence, and Neurourology: Highlights from the Society for Urodynamics and Female Urology Annual Winter Meeting, Feb. 28-Mar. 2, 2008, Miami, FL; Rev Urol; 2008; 229-231; 10.
Noblett, K, et al.; Results of a prospective, multicenter study evaluating quality of life, safety, and efficacy of sacral neuromodulation at twelve months in subjects with symptoms of overactive bladder; Neurourol Urodyn; 2016; 246-251; 35.
Noblett, KL, et al.; Sacral nerve stimulation for the treatment of refractory voiding and bowel dysfunction; Am J Obstet Gynecol; 2014; 99-106; 210.
Nordling, J; Surgical treatment of painful bladder syndrome/interstitial cystitis; Womens Health (Lond Engl); 2006; 233-238; 2.
Nyarangi-Dix, JN, et al.; [Overactive bladder syndrome. Are there indications for surgical therapy?]; Urologe A; 2006; 1289-1290, 1292; 45.
Occhino, JA, et al.; Sacral nerve modulation in overactive bladder; Curr Urol Rep; 2010; 348-352; 11.
Oerlemans, DJ, et al.; Is on-demand sacral neuromodulation in patients with OAB syndrome a feasible therapy regime?; Neurourol Urodyn; 2011; 1493-1496; 30.
Oerlemans, DJ, et al.; Sacral nerve stimulation for neuromodulation of the lower urinary tract; Neurourol Urodyn; 2008; 28-33; 27.
Offiah, I, et al.; Interstitial cystitis/bladder pain syndrome: diagnosis and management; Int Urogynecol J; 2013; 1243-1256; 24.
Oliver, S, et al.; Measuring the sensations of urge and bladder filling during cystometry in urge incontinence and the effects of neuromodulation; Neurourol Urodyn; 2003; 42567; 22.
Oliver_et_al-2003-Neurourology_and_Urodynamics.
Olivera, CK, et al.; Non-antimuscarinic treatment for overactive bladder: a systematic review; Am J Obstet Gynecol; 2016;Abstract.
Olujide, LO, et al.; Female voiding dysfunction; Best Pract Res Clin Obstet Gynaecol; 2005; 807-828; 19.
Oom, DM, et al.; Anterior sphincteroplasty for fecal incontinence: a single center experience in the era of sacral neuromodulation; Dis Colon Rectum; 2009; 1681-1687; 52.
Oom, DM, et al.; Is sacral neuromodulation for fecal incontinence worthwhile in patients with associated pelvic floor injury?; Dis Colon Rectum; 2010; 422-427; 53.
Ordia, JI, et al.; Continuous intrathecal baclofen infusion delivered by a programmable pump for the treatment of severe spasticity following traumatic brain injury; Neuromodulation; 2002; 103-107; 5.
O'Reilly, BA, et al.; A prospective randomised double-blind controlled trial evaluating the effect of trans-sacral magnetic stimulation in women with overactive bladder; Int Urogynecol J Pelvic Floor Dysfunct; 2008; 497-502; 19.
Osman, NI, et al.; Fowler's syndrome-a cause of unexplained urinary retention in young women?; Nat Rev Urol; 2014; 87-98; 11;Abstract.
Osman, NI, et al.; Overactive bladder syndrome: Current pathophysiological concepts and therapeutic approaches; Arab J Urol; 2013; 313-318; 11.
Otto, W, et al.; [Sacral neuromodulation as second-line treatment strategy for lower urinary tract symptoms of various aetiologies: experience of a German high-volume clinic]; Aktuelle Urol; 2012; 162-166; 43;Abstract.
Ozyalcin, NS, et al.; [Sacral nerve stimulation in fecal incontinence; efficacy and safety]; Agri; 2004; 35-44; 16;Abstract.
Panicker, JN, et al.; Lower urinary tract dysfunction in the neurological patient: clinical assessment and management; Lancet Neurol; 2015; 720-732; 14.
Pannek, J, et al.; [Initial results of Stoller peripheral neuromodulation in disorders of bladder function]; Urologe A; 2003; 1470-1476; 42.
Parija, SC, et al.; Adenosine- and alpha,beta-methylene ATP-induced differential inhibition of cholinergic and non-cholinergic neurogenic responses in rat urinary bladder; Br J Pharmacol; 1991; 396-400; 102.

(56) References Cited

OTHER PUBLICATIONS

Park, SH, et al.; Overactive bladder: treatment options for the aging woman; Int J Fertil Womens Med; 2005; 37-44; 50;Abstract.
Parnell, BA, et al.; The effect of sacral neuromodulation on pudendal nerve function and female sexual function; Neurourol Urodyn; 2015; 456-460; 34.
Pascual, I, et al.; Sacral nerve stimulation for fecal incontinence; Rev Esp Enferm Dig; 2011; 355-359; 103.
Patidar, N, et al.; Transcutaneous posterior tibial nerve stimulation in pediatric overactive bladder: A preliminary report; J Pediatr Urol; 2015; 351.e351-356; 11.
Pauls, RN, et al.; Effects of sacral neuromodulation on female sexual function; Int Urogynecol J Pelvic Floor Dysfunct; 2007; 391-395; 18.
Peeters, K, et al.; Long-term follow-up of sacral neuromodulation for lower urinary tract dysfunction; BJU Int; 2014; 789-794; 113.
Peirce, C, et al.; Central representation of the inferior rectal nerve of the rat; Dis Colon Rectum; 2010; 315-320; 53.
Pelaez, E, et al.; [Epidural spinal cord stimulation for interstitial cystitis]; Rev Esp Anestesiol Reanim; 2004; 549-552; 51;Abstract.
Pelliccioni, G, et al.; External anal sphincter responses after S3 spinal root surface electrical stimulation; Neurourol Urodyn; 2006; 788-791; 25.
Pena, G, et al.; Cholinergic regulatory lymphocytes re-establish neuromodulation of innate immune responses in sepsis; J Immunol; 2011; 718-725; 187.
Peng, CW, et al.; Pudendal neuromodulation with a closed-loop control strategy to improve bladder functions in the animal study; Conf Proc IEEE Eng Med Biol Soc; 2013; 3626-3629; 2013.
Penson, DF; Re: Cost-effectiveness analysis of sacral neuromodulation and botulinum toxin a treatment for patients with idiopathic overactive bladder; J Urol; 2012; 2157-2158; 187.
Penson, DF; Re: Physician Use of Sacral Neuromodulation among Medicare Beneficiaries with Overactive Bladder and Urinary Retention; J Urol; 2016; 689; 195.
Perissinotto et al.; Transcutaneous Tibial Nerve Stimulation in the Treatment of Lower UrinaryTract Symptoms and Its Impact on Health-Related Quality of Life in Patients With ParkinsonDisease; J Wound, Ostomy and Continence Nurses Society; 2015; 94-99; 42.
Perrigot, M, et al.; [Perineal electrical stimulation and rehabilitation in urinary incontinence and other symptoms of non-neurologic origin]; Ann Readapt Med Phys; 2008; 479-490; 51;Abstract.
Pescatori, LC, et al.; Sphincteroplasty for anal incontinence; Gastroenterol Rep (Oxf); 2014; 92-97; 2.
Peters, KM, et al.; Characterization of a clinical cohort of 87 women with interstitial cystitis/painful bladder syndrome; Urology; 2008; 634-640; 71.
Peters, KM, et al.; Chronic pudendal neuromodulation: expanding available treatment options for refractory urologic symptoms; Neurourol Urodyn; 2010; 1267-1271; 29.
Peters, KM, et al.; Clinical outcomes of sacral neuromodulation in patients with neurologic conditions; Urology; 2013; 738-743; 81.
Peters, KM, et al.; Does patient age impact outcomes of neuromodulation?; Neurourol Urodyn; 2013; 30-36; 32.
Abdel Raheem, A, et al.; Voiding dysfunction in women: Howto manage it correctly; Arab J Urol; 2013; 319-330; 11.
Abraham, N, et al.; Urgency aftera sling: review of the management; Curr Urol Rep; 2014; 400; 15.
Abrams, P, et al.; The role of neuromodulation in the management of urinary urge incontinence; BJU Int; 2003; 355-359; 91.
Abrams, P; The role of neuromodulation in the management of urinary urge incontinence; BJU Int; 2004; 1116; 93.
Allahdin, S, et al.; An overview of treatment of overactive bladder syndrome in women; J Obstet Gynaecol; 2012; 217-221; 32.
Alo, KM, et al.; Sacral nerve root stimulation for the treatment of urge incontinence and detrusor dysfunction utilizing a cephalocaudal intraspinal method of lead insertion: a case report; Neuromodulation; 2001; 53-58; 4.
Alo, KM, et al.; Selective Nerve Root Stimulation (SNRS) for the Treatment of Intractable Pelvic Pain and Motor Dysfunction: A Case Report; Neuromodulation; 2001; 19-23; 4.
Al-Shaiji, TF, et al.; Pelvic electrical neuromodulation for the treatment of overactive bladder symptoms; Adv Urol; 2011; 757454; 2011.
Al-Zahrani, AA, et al.; Long-term outcome and surgical interventions after sacral neuromodulation implant for lower urinary tract symptoms: 14-year experience at 1 center; J Urol; 2011; 981-986; 185.
Amarenco, G, et al.; Urodynamic effect of acute transcutaneous posterior tibial nerve stimulation in overactive bladder; J Urol; 2003; 2210-2215; 169.
Amend, B, et al.; [Second-line therapy of idiopathic detrusor overactivity. Sacral neuromodulation and botulinum toxin A]; Urologe A; 2010; 245-252; 49.
Amend, B, et al.; Prolonged percutaneous SNM testing does not cause infection-related explanation; BJU Int; 2013; 485-491; 111.
Amoroso, L, et al.; Sacral-neuromodulation CT-guided; Radiol Med; 2005; 421-429; 109;Abstract.
Amundsen, CL, et al.; Sacral neuromodulation for intractable urge incontinence: are there factors associated with cure?; Urology; 2005; 746-750; 66.
Amundsen, CL, et al.; Sacral neuromodulation in an older, urge-incontinent population; Am J Obstet Gynecol; 2002; 1462-1465; discussion 1465; 187.
Amundsen, CL, et al.; The Refractory Overactive Bladder: Sacral NEuromodulation vs. BoTulinum Toxin Assessment: Rosetta trial; Contemp Clin Trials; 2014; 272-283; 37.
Anger, JT, et al.; The effect of sacral neuromodulation on anticholinergic use and expenditures in a privately insured population; Neuromodulation; 2014; 72-74; discussion 74; 17.
Antolak, SJ, Jr., et al.; Therapeutic pudendal nerve blocks using corticosteroids cure pelvic pain after failure of sacral neuromodulation; Pain Med; 2009; 186-189; 10.
Antolak, SJ, Jr.; Re: Sacral neuromodulation for the symptomatic treatment of refractory interstitial cystitis: a prospective study; J Urol; 2003; 1956; author reply 1956; 170.
Anton, PA; Stress and mind-body impact on the course of inflammatory bowel diseases; Semin Gastrointest Dis; 1999; 14-19; 10;Abstract.
Aoun, F, et al.; [Lower urinary tract dysfunction following radical hysterectomy]; Prog Urol; 2015; 1184-1190; 25; Abstract.
Apostolidis, A; Neuromodulation for intractable OAB; Neurourol Urodyn; 2011; 766-770; 30.
Arlandis, S, et al.; Cost-effectiveness of sacral neuromodulation compared to botulinum neurotoxin a or continued medical management in refractory overactive bladder; Value Health; 2011; 219-228; 14.
Arnold, J, et al.; Overactive bladder syndrome—management and treatment options; Aust Fam Physician; 2012; 378-883; 41.
Arrabal-Polo, MA, et al.; Clinical efficacy in the treatment of overactive bladder refractory to anticholinergics by posterior tibial nerve stimulation; Korean J Urol; 2012; 483-486; 53.
Atiemo, HO, et al.; Evaluation and management of refractory overactive bladder; Curr Urol Rep; 2006; 370-375; 7.
Atnip, S, et al.; A unique approach to severe constipation; Urol Nurs; 2011; 348-350; 31.
Badawi, JK, et al.; [Current diagnostics and therapy of the overactive bladder and urge incontinence]; Dtsch Med Wochenschr; 2005; 1503-1506; 130;Abstract.
Badlani, GH; Update on lower urinary tract symptoms; ScientificWorldJournal; 2009; 499-500; 9.
Baeten, CG; Status of sacral neuromodulation for refractory constipation; Colorectal Dis; 2011; 19-22; 13 Suppl 2.
Balchandra, P, et al.; Women's perspective: intra-detrusor botox versus sacral neuromodulation for overactive bladder symptoms after unsuccessful anticholinergic treatment; Int Urogynecol J; 2014; 1059-1064; 25.
Banakhar, M, et al.; Effect of sacral neuromodulation on female sexual function and quality of life: Are they correlated?; Can Urol Assoc J; 2014; E762-767; 8.

(56) References Cited

OTHER PUBLICATIONS

Banakhar, M, et al.; Sacral Neuromodulation for Genitourinary Problems; Prog Neurol Surg; 2015; 192-199; 29; Abstract.
Banakhar, MA, et al.; Sacral neuromodulation and refractory overactive bladder: an emerging tool for an old problem; Ther Adv Urol; 2012; 179-185; 4.
Bannowsky, A, et al.; [Sacral neuromodulation in treatment of functional disorders of the lower urinary tract. An overview of basic principles, indications, outcomes]; Urologe A; 2003; 1357-1365; 42.
Bannowsky, A, et al.; Urodynamic changes and response rates in patients treated with permanent electrodes compared to conventional wire electrodes in the peripheral nerve evaluation test; World J Urol; 2008; 623-626; 26.
Banyo, T; [The role of electrical neuromodulation in the therapy of chronic lower urinary tract dysfunction]; Ideggyogy Sz; 2003; 68-71; 56;Abstract.
Barnett, G, et al.; Re: Cost of neuromodulation therapies for overactive bladder: percutaneous tibial nerve stimulation versus sacral nerve stimulation: M. Martinson, S. MacDiarmid and E. Black J Urol 2013; 189:210-216; J Urol; 2013; 1444-1445; 190.
Baron, M, et al.; [Does urinary sacral neuromodulation improve bowel symptoms other than fecal incontinence: A systematic review]; Prog Urol; 2016;Abstract.
Barroso U Jr et al.; Electrical nerve stimulation for overactive bladder in children;Nature Reviews Urology; 2011; 402-407; 8.
Barroso, U, Jr., et al.; Posterior tibial nerve stimulation vs parasacral transcutaneous neuromodulation for overactive bladder in children; J Urol; 2013; 673-677; 190.
Bartley, J, et al.; Neuromodulation for overactive bladder; Nat Rev Urol; 2013; 513-521; 10.
Bartley, JM, et al.; Understanding clinic options for overactive bladder; Curr Urol Rep; 2013; 541-548; 14.
Batla, A, et al.; Lower urinary tract dysfunction in patients with functional movement disorders; J Neurol Sci; 2016; 192-194; 361.
Bayrak, O, et al.; Botulinum toxin injections for treating neurogenic detrusor overactivity; Turk J Urol; 2015; 221-227; 41.
Bemelmans, BL, et al.; Neuromodulation by implant for treating lower urinary tract symptoms and dysfunction; Eur Urol; 1999; 81-91; 36;Abstract.
Beneton, C, et al.; [The medical treatment of overactive bladder]; Neurochirurgie; 2003; 369-376; 49;Abstract.
Benson, JT, et al.; Pudendal neuralgia, a severe pain syndrome; Am J Obstet Gynecol; 2005; 1663-1668; 192.
Benson, JT; New therapeutic options for urge incontinence; Curr Womens Health Rep; 2001; 61-66; 1;Abstract.
Benson-Cooper, S, et al.; Introduction of sacral neuromodulation for the treatment of faecal incontinence; N Z Med J; 2013; 47-53; 126.
Maher, CF, et al.; Percutaneous sacral nerve root neuromodulation for intractable interstitial cystitis; J Urol; 2001; 384-886; 165.
Maher, RM, et al.; A novel externally applied neuromuscular stimulator for the treatment of stress urinary incontinence in women—a pilot study; Neuromodulation; 2013; 590-594; discussion 594; 16.
Majerus, SJ, et al.; Low-power wireless micromanometer system for acute and chronic bladder-pressure monitoring IEEE Trans Biomed Eng; 2011; 763-767; 58.
Majerus, SJ, et al.; Wireless, Ultra-Low-Power Implantable Sensor for Chronic Bladder Pressure Monitoring; ACM J Emerg Technol Comput Syst; 2012;8.
Mally, AD, et al.; Role of opioid and metabotropic glutamate 5 receptors in pudendal inhibition of bladder overactivity in cats; J Urol; 2013; 1574-1579; 189.
Malossi, J, et al.; Sacral neuromodulation for the treatment of bladder dysfunction; Curr Urol Rep; 2002; 61-66; 3.
Malouf, AJ, et al.; Short-term effects of sacral nerve stimulation for idiopathic slow transit constipation; World J Surg; 2002; 166-170; 26.
Mamopoulos, A, et al.; Active sacral neuromodulator during pregnancy: a unique case report; Am J Obstet Gynecol; 2014; e4-5; 211.
Manriquez, V, et al.; Transcutaneous posterior tibial nerve stimulation versus extended release oxybutynin in overactive bladder patients. A prospective randomized trial; Eur J Obstet Gynecol Reprod Biol; 2016; 42531; 196.
Marcelissen, T, et al.; Is the screening method of sacral neuromodulation a prognostic factor for long-term success?; J Urol; 2011; 583-587; 185.
Marcelissen, T, et al.; Sacral neuromodulation as a treatment for chronic pelvic pain; J Urol; 2011; 387-393; 186.
Marcelissen, TA, et al.; Long-term results of sacral neuromodulation with the lined lead procedure; J Urol; 2010; 1997-2000; 184.
Marcelissen, TA, et al.; Psychological and psychiatric factors as predictors for success in sacral neuromodulation treatment; BJU Int; 2011; 1834-1838; 108.
Marcelissen, TA, et al.; The effect of pulse rate changes on the clinical outcome of sacral neuromodulation; J Urol; 2011; 1781-1785; 185.
Marcelissen, TA, et al.; The use of bilateral sacral nerve stimulation in patients with loss of unilateral treatment efficacy; J Urol; 2011; 976-980; 185.
Marinkovic, SP, et al.; Neuromodulation for Overactive Bladder Symptoms in Women Utilizing Either Motor or Sensory/Motor Provocation With a Minimum Nine-Year Follow-Up; Neuromodulation; 2015; 517-521; discussion 521; 18.
Martin Braun, P, et al.; [Continuous bilateral sacral neuromodulation as a minimally invasive implantation technique in patients with functional bladder changes]; Arch Esp Urol; 2003; 497-501; 56.
Martinson, M, et al.; Cost of neuromodulation therapies for overactive bladder: percutaneous tibial nerve stimulation versus sacral nerve stimulation; J Urol; 2013; 210-216; 189.
Mason, MD, et al.; Prospective Evaluation of Sacral Neuromodulation in Children: Outcomes and Urodynamic Predictors of Success; J Urol; 2016.
Matsuta, Y, et al.; Contribution of opioid and metabotropic glutamate receptor mechanisms to inhibition of bladder overactivity by tibial nerve stimulation; Am J Physiol Regul Integr Comp Physiol; 2013; R126-133; 305.
Matsuta, Y, et al.; Effect of methysergide on pudendal inhibition of micturition reflex in cats; Exp Neurol; 2013; 250-258; 247.
Matsuta, Y, et al.; Poststimulation inhibition of the micturition reflex induced by tibial nerve stimulation in rats; Physiol Rep; 2014; e00205; 2.
Mauroy, B, et al.; [Long-term results of interferential current stimulation in the treatment of bladder instability]; Prog Urol; 2001; 34-39; 11; Abstract.
Mayer, R; Neuromodulation—who, what, when, where and why?; J Urol; 2010; 17-18; 183.
Mayr, CA, et al.; Cost-effectiveness of novel therapies for overactive bladder; Expert Rev Pharmacoecon Outcomes Res; 2014; 527-535; 14.
Mazo, EB, et al.; [Temporary sacral and tibial neuromodulation in treating patients with overactive urinary bladder]; Zh Vopr Neirokhir Im N N Burdenko; 2002; 17-21; Abstract.
Mazo, EB, et al.; [Temporary sacral neuromodulation in patients with urge incontinence]; Urologiia; 2000; 42-46; ;Abstract.
Mazo, EB, et al.; [The role of somatosensory evoked potentials in prognosis of efficacy of tibial neuromodulation in patients with hyperactive urinary bladder]; Urologiia; 2005; 49-52; ;Abstract.
Mcachran, SE, et al.; Sacral neuromodulation in the older woman; Clin Obstet Gynecol; 2007; 735-744; 50.
McKertich, K; Urinary incontinence-procedural and surgical treatments for women; Aust Fam Physician; 2008; 122-131; 37.
McNevin, MS, et al.; Outcomes associated with Interstim therapy for medically refractory fecal incontinence; Am J Surg; 2014; 735-737; discussion 737-788; 207.
Mehnert, U, et al.; [Neuro-urological dysfunction of the lower urinary tract in CNS diseases: pathophysiology, epidemiology, and treatment options]; Urologe A; 2012; 189-197; 51.
Mehnert, U, et al.; The management of urinary incontinence in the male neurological patient; Curr Opin Urol; 2014; 586-592; 24.
Meissnitzer, T, et al.; CT-Guided Lead Placement for Selective Sacral Neuromodulation to Treat Lower Urinary Tract Dysfunctions; AJR Am J Roentgenol; 2015; 1139-1142; 205.

(56) References Cited

OTHER PUBLICATIONS

Melenhorst, J, et al.; Sacral neuromodulation in patients with faecal incontinence: results of the first 100 permanent implantations; Colorectal Dis; 2007; 725-730; 9.

Meurette, G, et al.; Sacral nerve stimulation enhances epithelial barrier of the rectum: results from a porcine model; Neurogastroenterol Motil; 2012; 267-273, e110; 24.

Michael Craggs and Jonathon McFarlane; Neuromodulation of the lower urinary tract; Experimental Physiology (1999), 84, 149-160.

Michelsen, HB, et al.; Rectal volume tolerability and anal pressures in patients with fecal incontinence treated with sacral nerve stimulation; Dis Colon Rectum; 2006; 1039-1044; 49.

Miller, JJ, et al.; Diagnosis and treatment of overactive bladder; Minerva Ginecol; 2005; 501-520; 57;Abstract.

Milne, JL; Behavioral therapies for overactive bladder: making sense of the evidence; J Wound Ostomy Continence Nurs; 2008; 93-101; quiz 102-103; 35;Abstract.

Minardi, D, et al.; Activity and expression of nitric oxide synthase in rat bladder after sacral neuromodulation; Int J Immunopathol Pharmacol; 2008; 129-135; 21;Abstract.

Minardi, D, et al.; Lower urinary tract and bowel disorders and multiple sclerosis: role of sacral neuromodulation: a preliminary report; Neuromodulation; 2005; 176-181; 8.

Miotla, P, et al.; [Sacral nerve stimulation in the treatment of the lower urinary tract function disorders]; Ginekol Pol; 2011; 851-856; 82.

Mishra, NN; Clinical presentation and treatment of bladder pain syndrome/interstitial cystitis (BPS/IC) in India; Transl Androl Urol; 2015; 512-523; 4.

Moon, KH, et al.; Prospective Trial of Sacral Neuromodulation for Refractory Overactive Bladder Syndrome in Korean Patients; Low Urin Tract Symptoms; 2014; 175-179; 6.

Moutzouris, DA, et al.; Interstitial cystitis: an unsolved enigma; Clin J Am Soc Nephrol; 2009; 1844-1857; 4.

Murphy, AM, et al.; Treatment of overactive bladder: what is on the horizon?; Int Urogynecol J; 2013; 42503; 24.

Musco, S, et al.; Percutaneous Tibial Nerve Stimulation Improves Female Sexual Function in Women With Overactive Bladder Syndrome; J Sex Med; 2016.

N. Patidar et al.; Transcutaneous posterior tibial nerve stimulation in pediatric overactivebladder: A preliminary report; Journal of Pediatric Urology; 2015; 351.e1-351.e6; 11.

Nakib, N, et al.; Neuromodulation versus neurotoxin for the treatment of refractory detrusor overactivity: for neuromodulation; Nat Clin Pract Urol; 2008; 118-119; 5.

Sutherland, RS, et al.; Vesicourethral function in mice with genetic disruption of neuronal nitric oxide synthase; J Urol; 1997; 1109-1116; 157.

Svensson, L, et al.; Neuromodulation of experimental Shigella infection reduces damage to the gut mucosa; Microbes Infect; 2004; 256-264; 6.

Swinn, MJ, et al.; The cause and natural history of isolated urinary retention in young women; J Urol; 2002; 151-156; 167.

Tai et al., "FootStim: Neuromodulation therapy for overactive bladder"; http://www.engineering.pitt.edu/Sub-Sites/Programs/Coulter/Projects/2013—FootStim/: retrieved on Sep. 26, 2017.

Fai, C, et al.; Bladder inhibition by intermittent pudendal nerve stimulation in cat using transdermal amplitude-modulated signal (TAMS); Neurourol Urodyn; 2012; 1181-1184; 31.

Tai, C, et al.; Inhibition of bladder overactivity by stimulation of feline pudendal nerve using transdermal amplitude-modulated signal (TAMS); BJU Int; 2012; 782-787; 109.

Tai, C, et al.; Irritation induced bladder overactivity is suppressed by tibial nerve stimulation in cats; J Urol; 2011; 326-330; 186.

Tai, C, et al.; Prolonged poststimulation inhibition of bladder activity induced by tibial nerve stimulation in cats; Am J Physiol Renal Physiol; 2011; F385-392; 300.

Takahashi, S, et al.; Overactive bladder: magnetic versus electrical stimulation; CurrOpin Obstet Gynecol; 2003; 429-433; 15.

Tanagho, EA; Concepts of neuromodulation; Neurourol Urodyn; 1993; 487-488; 12.

Tanagho, EA; Neuromodulation in the management of voiding dysfunction in children; J Urol; 1992; 655-657; 148; Abstract.

Tang, H, et al.; Combination of sacral neuromodulation and tolterodine for treatment of idiopathic overactive bladder in women: a clinical trial; Urol J; 2014; 1800-1805; 11.

Taweel, WA, et al.; Neurogenic bladder in spinal cord injury patients; Res Rep Urol; 2015; 85-99; 7.

Thin, NN, et al.; Randomized clinical trial of sacral versus percutaneous tibial nerve stimulation in patients with faecal incontinence; Br J Surg; 2015; 349-358; 102.

Thin, NN, et al.; Systematic review of the clinical effectiveness of neuromodulation in the treatment of faecal incontinence; Br J Surg; 2013; 1430-1447; 100.

Thomas, GP, et al.; A pilot study of transcutaneous sacral nerve stimulation for faecal incontinence; Colorectal Dis; 2013; 1406-1409; 15.

Thomas, GP, et al.; Sacral nerve stimulation for faecal incontinence secondary to congenital imperforate anus; Tech Coloproctol; 2013; 227-229; 17.

Thompson, JH, et al.; Sacral neuromodulation: Therapy evolution; Indian J Urol; 2010; 379-384; 26.

Thoua, NM, et al.; Internal anal sphincter atrophy in patients with systemic sclerosis; Rheumatology (Oxford); 2011; 1596-1602; 50.

Tian, Y, et al.; Inhibitory Effect and Possible Mechanism of Intraurethral Stimulation on Overactive Bladder in Female Rats; Int Neurourol J; 2015; 151-157; 19.

Tirlapur, SA, et al.; Nerve stimulation for chronic pelvic pain and bladder pain syndrome: a systematic review; Acta Obstet Gynecol Scand; 2013; 881-887; 92.

Tjandra, JJ, et al.; Sacral nerve stimulation is more effective than optimal medical therapy for severe fecal incontinence: a randomized, controlled study; Dis Colon Rectum; 2008; 494-502; 51.

Tomonori Yamanishi et al.; Neuromodulation for the Treatment of Lower Urinary TractSymptoms; Low Urin Tract Symptoms; 2015; 121-132; 7.

Traynor, TR, et al.; Neuromodulation of ion transport in porcine distal colon: NPY reduces secretory actions of eukotrienes; Am J Physiol; 1995; R426-431; 269;Abstract.

Trevizol, AP, et al.; Trigeminal Nerve Stimulation (TNS) for the Treatment of Irritable Bowel Syndrome in an Elderiy Patient with Major Depressive Disorder: A Case Study; Brain Stimul; 2015; 1235-1236; 8.

Turner, WH, et al.; Smooth muscle of the bladder in the normal and the diseased state: pathophysiology, diagnosis and treatment; Pharmacol Ther; 1997; 77-110; 75.

Ullah, S, et al.; Temporary gastric neuromodulation for intractable nausea and vomiting; Ann R Coll Surg Engl; 2011; 624-628; 93.

Uludag, O, et al.; [Sacral neuromodulation is effective in the treatment of fecal incontinence with intact sphincter muscles; a prospective study]; Ned Tijdschr Geneeskd; 2002; 989-993; 146;Abstract.

Uludag, O, et al.; Sacral neuromodulation in patients with fecal incontinence: a single-center study; Dis Colon Rectum; 2004; 1350-1357; 47.

Uludag, O, et al.; Sacral neuromodulation: does it affect the rectoanal angle in patients with fecal incontinence?; World J Surg; 2010; 1109-1114; 34.

Uludag, O, et al.; Sacral neuromodulation: long-term outcome and quality of life in patients with faecal incontinence; Colorectal Dis; 2011; 1162-1166; 13.

Uludag, O, et al.; Sacral neuromodulation; does it affect colonic transit time in patients with faecal incontinence?; Colorectal Dis; 2006; 318-322; 8.

Unger, CA, et al.; Fecal incontinence: the role of the urologist; Curr Urol Rep; 2014; 388; 15.

Unwala, DJ, et al.; Repeated botulinum toxin injection for idiopathic overactive bladder: will chemodenervation become a long-term solution?; Curr Urol Rep; 2007; 419-424; 8.

Uranga, A, et al.; An integrated implantable electrical sacral root stimulator for bladder control; Neuromodulation; 2002; 238-247; 5.

(56) References Cited

OTHER PUBLICATIONS

Vaarala, MH, et al.; Sacral neuromodulation in urological indications: the Finnish experience; Scand J Urol Nephrol; 2011; 46-51; 45.
Vaizey, CJ, et al.; Effects of short term sacral nerve stimulation on anal and rectal function in patients with anal incontinence; Gut; 1999; 407-412; 44.
Vallet, C, et al.; Sacral nerve stimulation for faecal incontinence: response rate, satisfaction and the value of preoperative investigation in patient selection; Colorectal Dis; 2010; 247-253; 12.
Van Balken, MR, et al.; Prognostic factors for successful percutaneous tibial nerve stimulation; Eur Urol; 2006; 360-365; 49.
Van Balken, MR, et al.; Sexual functioning in patients with lower urinary tract dysfunction improves after percutaneous tibial nerve stimulation; Int J Impot Res; 2006; 470-475; discussion 476; 18.
Van Balken, MR, et al.; The use of electrical devices for the treatment of bladder dysfunction: a review of methods; J Urol; 2004; 846-851; 172.
Van Balken, MR; Percutaneous tibial nerve stimulation: the Urgent PC device; Expert Rev Med Devices; 2007; 393-698; 4.
Van Der Aa, HE, et al.; Sacral anterior root stimulation for bladder control: clinical results; Arch Physiol Biochem; 1999; 248-256; 107.
Van Der Pal, F, et al.; Current opinion on the working mechanisms of neuromodulation in the treatment of lower urinary tract dysfunction; Curr Opin Urol; 2006; 261-267; 16.
Van Der Pal, F, et al.; Implant-Driven Tibial Nerve Stimulation in the Treatment of Refractory Overactive Bladder Syndrome: 12-Month Follow-up; Neuromodulation; 2006; 163-171; 9.
Van Kerrebroeck, P; Editorial comment re: Killinger et al. "Secondary changes in bowel function after successful treatment of voiding symptoms with neuromodulation"; Neurourol Urodyn; 2011; 1403; 30.
Van Kerrebroeck, PE, et al.; Results of sacral neuromodulation therapy for urinary voiding dysfunction: outcomes of a prospective, worldwide clinical study; J Urol; 2007; 2029-2034; 178.
Van Kerrebroeck, PE; Advances in the role of sacral nerve neuromodulation in lower urinary tract symptoms; Int Urogynecol J; 2010; S467-474; 21 Suppl 2.
Van Kerrebroeck, PE; Neuromodulation and other electrostimulatory techniques; Scand J Urol Nephrol Suppl; 2002; 82-86.
Van Kerrebroeck, PE; The role of electrical stimulation in voiding dysfunction; Eur Urol; 1998; 27-30; 34 Suppl 1; Abstract.
Canbaz Kabay, S, et al.; Long term sustained therapeutic effects of percutaneous posterior tibial nerve stimulation treatment of neurogenic overactive bladder in multiple sclerosis patients: 12-months results; Neurourol Urodyn; 2015; Abstract.
Cardarelli, S, et al.; Efficacy of sacral neuromodulation on urological diseases: a multicentric research project; Urologia; 2012; 90-96; 79.
Cardot, V, et al.; [Guidelines for the treatment of urinary incontinence in women with refiactory idiopathic vesical hyperactivity using sacral neuromodulation]; Prog Urol; 2010; S161-169; 20 Suppl 2;Abstract.
Carey, HV, et al.; Neuromodulation of intestinal transport in the suckling mouse; Am J Physiol; 1989; R481-486; 256; Abstract.
Carey, M, et al.; Sacral nerve root stimulation for lower urinary tract dysfunction: overcoming the problem of lead migration; BJU Int; 2001; 15-18; 87.
Carlson, JJ, et al.; Estimating the cost-effectiveness of onabotulinumtoxinA for neurogenic detrusor overactivity in the United States; Clin Ther; 2013; 414-424; 35.
Carlucci, L, et al.; Functional variability of sacral roots in bladder control; J Neurosurg Spine; 2014; 961-965; 21.
Carr, MC; Conservative nonsurgical management of spina bifida; Curr Urol Rep; 2010; 109-113; 11.
Carrington, EV, et al.; A systematic review of sacral nerve stimulation mechanisms in the treatment of fecal ncontinence and constipation; Neurogastroenterol Motil; 2014; 1222-1237; 26.

Chaabane, W, et al.; Sacral neuromodulation for treating neurogenic bladder dysfunction: clinical and urodynamic study; Neurourol Urodyn; 2011; 547-550; 30.
Dhan, DK, et al.; Effective treatment of dyssynergic defecation using sacral neuromodulation in a patient with cerebral palsy; Female Pelvic Med Reconstr Surg; 2015; e27-29; 21;Abstract.
Chancellor, MB, et al.; Principles of Sacral Nerve Stimulation (SNS) for the Treatment of Bladder and Urethral Sphincter Dysfunctions; Neuromodulation; 2000; 16-26; 3.
Chandra, A, et al.; Neuromodulation of perineally transposed antropylorus with pudendal nerve anastomosis following total anorectal reconstruction in humans; Neurogastroenterol Motil; 2014; 1342-1348; 26.
Chapple, C, et al.; The second-line management of idiopathic overactive bladder: what is the place of sacral neuromodulation and botulinum toxin-A in contemporary practice?; BJU Int; 2009; 1188-1190; 104.
Chapple, CR, et al.; Surgery for detrusor overactivity; World J Urol; 1998; 268-273; 16.
Chartier-Kastler, E, et al.; [Sacral neuromodulation with InterStim system: Results from the French national register]; Prog Urol; 2011; 209-217; 21;Abstract.
Chartier-Kastler, E, et al.; [Update on the second line management of idiopathic overactive bladder]; Prog Urol; 2009; 530-537; 19;Abstract.
Chartier-Kastler, E; Sacral neuromodulation for treating the symptoms of overactive bladder syndrome and non-obstructive urinary retention: >10 years of clinical experience; BJU Int; 2008; 417-423; 101.
Chatoor, D, et al.; Constipation and evacuation disorders; Best Pract Res Clin Gastroenterol; 2009; 517-530; 23.
Dhen, G, et al.; Sacral neuromodulation for neurogenic bladder and bowel dysfunction with multiple symptoms secondary to spinal cord disease; Spinal Cord; 2014;Abstract.
Chen, G, et al.; The inhibitory effects of pudendal nerve stimulation on bladder overactivity in spinal cord injury dogs; is early stimulation necessary?; Neuromodulation; 2012; 232-237; discussion 237; 15.
Chen, ML, et al.; Electrical stimulation of somatic afferent nerves in the foot increases bladder capacity in healthy human subjects; J Urol; 2014; 1009-1013; 191.
Chen, SC, et al.; Pudendal neuromodulation improves voiding efficiency in diabetic rats; Neurourol Urodyn; 2013; 293-300; 32.
Chiarioni, G, et al.; Neuromodulation for fecal incontinence: an effective surgical intervention; World J Gastroenterol; 2013; 7048-7054; 19.
Choudhary, M, et al.; Inhibitory effects of tibial nerve stimulation on bladder neurophysiology in rats; Springerplus; 2016; 35; 5.
Christopher J. Chermansky et al., "MP68-15 Electrical Stimulation of Afferent Nerves in the Foot Nith Transcutaneous Adhesive Pad Electrodes Improves Overactive Bladder Symptoms in Nomen", The Journal of Urology, vol. 195, No. 4S, Supplement, Monday, May 9, 2016,2 pages.
Christopher J. Chermansky, "Foot/Hand Neuromodulation for Overactive Bladder (OAB) (FootStim)"; First Posted: Oct. 30, 2013; http://clinicaltrials.govict2/show/NCT01972061; pp. 1-5.
Colaco, M, et al.; Current guidelines in the management of interstitial cystitis; Transl Androl Urol; 2015; 677-683; 4.
Collins, SM; Is the irritable gut an inflamed gut?; Scand J Gastroenterol Suppl; 1992; 102-105; 192;Abstract.
Comiter, CV; Conscious Neuromodulation of the Bladder before Clinical Use; J Urol; 2015; 16-17; 194.
Comiter, CV; Sacral neuromodulation for the symptomatic treatment of refractory interstitial cystitis: a prospective study; J Urol; 2003; 1369-1373; 169.
Corcos, J, et al.; Canadian Urological Association guidelines on urinary incontinence; Can J Urol; 2006; 3127-3138; 13;Abstract.
Cornu, JN; Actual treatment of overactive bladder and urge urinary incontinence; Minerva Urol Nefrol; 2013; 21-35; 65;Abstract.
Costa, JA, et al.; Spinal cord neuromodulation for voiding dysfunction; Clin Obstet Gynecol; 2000; 676-688; 43.
Craggs, M, et al.; Neuromodulation of the lower urinary tract; Exp Physiol; 1999; 149-160; 84.

(56) References Cited

OTHER PUBLICATIONS

Craggs, MD; Objective measurement of bladder sensation: use of a new patient-activated device and response to neuromodulation; BJU Int; 2005; 29-36; 96 Suppl 1.
Crock, LW, et al.; Central amygdala metabotropic glutamate receptor 5 in the modulation of visceral pain; J Meurosci; 2012; 14217-14226; 32.
Dahms, SE, et al.; Sacral neurostimulation and neuromodulation in urological practice; Curr Opin Urol; 2000; 329-335; 10.
Daneshgari, F, et al.; Future directions in pelvic neuromodulation; Urol Clin North Am; 2005; 113-115; viii; 32.
Daneshgari, F; Applications of neuromodulation of the lower urinary tract in female urology; Int Braz J Urol; 2006; 262-272; 32.
Daniels, DH, et al.; Sacral neuromodulation in diabetic patients: success and complications in the treatment of voiding dysfunction; Neurourol Urodyn; 2010; 578-581; 29.
Dasgupta, R, et al.; Changes in brain activity following sacral neuromodulation for urinary retention; J Urol; 2005; 2268-2272; 174.
Dasgupta, R, et al.; The management of female voiding dysfunction: Fowler's syndrome—a contemporary update; Curr Opin Urol; 2003; 293-299; 13.
Davis, T, et al.; Sacral neuromodulation outcomes for the treatment of refractory idiopathic detrusor overactivity stratified by indication: Lack of anticholinergic efficacy versus intolerability; Can Urol Assoc J; 2013; 176-178; 7.
De Boer, TA, et al.; [Male urinary incontinence]; Ned Tijdschr Geneeskd; 2008; 797-802; 152;Abstract.
De Gennaro, M, et al.; Current state of nerve stimulation technique for lower urinary tract dysfunction in children; J Urol; 2011; 1571-1577; 185.
De Gennaro, M, et al.; Percutaneous tibial nerve neuromodulation is well tolerated in children and effective for treating refractory vesical dysfunction; J Urol; 2004; 1911-1913; 171.
De Groat, WC, et al.; Impact of Bioelectronic Medicine on the Neural Regulation of Pelvic Visceral Function; Bioelectron Med; 2015; 25-36; 2015.
De Seze, M, et al.; [Peripheral electrical stimulation in neurogenic bladder]; Ann Readapt Med Phys; 2008; 473-478; 51;Abstract.
Deffieux, X, et al.; [Voiding dysfunction after surgical resection of deeply infiltrating endometriosis: pathophysiology and management]; Gynecol Obstet Fertil; 2007; S8-13; 35 Suppl 1;Abstract.
Kovacevic, M, et al.; Reflex neuromodulation of bladder function elicited by posterior tibial nerve stimulation in anesthetized rats; Am J Physiol Renal Physiol; 2015; F320-329; 308.
Krames, E, et al.; Spinal cord stimulation reverses pain and diarrheal episodes of irritable bowel syndrome: a case report; Neuromodulation; 2004; 82-88; 7.
Krivoborodov, GG, et al.; [Afferent stimulation of the tibial nerve in patients with hyperactive bladder]; Urologiia 2002; 36-39; Abstract.
Krivoborodov, GG, et al.; [Tibial neuromodulation in the treatment of neurogenic detrusor hyperactivity in patients with Parkinson's disease]; Urologiia; 2006; 42435; ;Abstract.
Krolczyk, G, et al.; Effects of continuous microchip (MC) vagal neuromodulation on gastrointestinal function in rats; J Physiol Pharmacol; 2001; 705-715; 52.
Kubota, M, et al.; Effects of neuromodulation with sacral magnetic stimulation for intractable bowel or bladder dysfunction in postoperative patients with anorectal malformation: a preliminary report; PediatrSurg Int; 2011; 599-603; 27.
Kumsar, S, et al.; Effects of sacral neuromodulation on isolated urinary bladder function in a rat model of spinal cord injury; Neuromodulation; 2015; 67-74; discussion 74-65; 18.
Kuo, HC; Recovery of detrusor function after urethral botulinum A toxin injection in patients with idiopathic low detrusor contractility and voiding dysfunction; Urology; 2007; 57-61; discussion 61-52; 69.
Kuo, TL, et al.; Pelvic floor spasm as a cause of voiding dysfunction; Curr Opin Urol; 2015; 311-316; 25.

Kurpad, R, et al.; The evaluation and management of refractory neurogenic overactive bladder; Curr Urol Rep; 2014; 444; 15.
Kutzenberger, J; [Neurogenic urinary incontinence. Value of surgical management]; Urologe A; 2008; 699-706; 47.
La, Th, et al.; Intermittent sacral neuromodulation for idiopathic urgency urinary incontinence in women; Neurourol Urodyn; 2015;Abstract.
Laudano, MA, et al.; Disparities in the Use of Sacral Neuromodulation among Medicare Beneficiaries; J Urol; 2015; 449-453; 194.
Laviana, A, et al.; Sacral neuromodulation for refractory overactive bladder, interstitial cystitis, and painful bladder syndrome; Neurosurg Clin N Am; 2014; 33-46; 25.
Lay, AH, et al.; The role of neuromodulation in patients with neurogenic overactive bladder; Curr Urol Rep; 2012; 343-347; 13.
Lazzeri, M, et al.; The challenge of overactive bladder therapy: alternative to antimuscarinic agents; Int Braz J Urol; 2006; 620-630; 32.
Le, NB, et al.; Expanding the Role of Neuromodulation for Overactive Bladder: New Indications and Alternatives to Delivery; Curr Bladder Dysfunct Rep; 2011; 25-30; 6.
Leclers, F, et al.; [Cystomanometric study of bladder sensation during sacral neuromodulation test]; Prog Urol; 2005; 238-243; 15;Abstract.
Lee, YY; What's New in the Toolbox for Constipation and Fecal Incontinence?; Front Med (Lausanne); 2014; 5; 1.
Leicht, W, et al.; [Botulinum toxin versus sacral neuromodulation for idiopathic detrusor overactivity]; Urologe A; 2012; 348-351; 51.
Leng, WW, et al.; How sacral nerve stimulation neuromodulation works; Urol Clin North Am; 2005; 42692; 32.
Leong, FC, et al.; Neuromodulation for the treatment of urinary incontinence; Mo Med; 2007; 435-439; 104;Abstract.
Leong, RK, et al.; Cost-effectiveness analysis of sacral neuromodulation and botulinum toxin A treatment for patients with idiopathic overactive bladder; BJU Int; 2011; 558-564; 108.
Leong, RK, et al.; Current information on sacral neuromodulation and botulinum toxin treatment for refractory idiopathic overactive bladder syndrome: a review; Urol Int; 2010; 245-253; 84.
Leong, RK, et al.; PNE versus 1st stage tined lead procedure: a direct comparison to select the most sensitive test method to identify patients suitable for sacral neuromodulation therapy; Neurourol Urodyn; 2011; 1249-1252; 30.
Leong, RK, et al.; Satisfaction and patient experience with sacral neuromodulation: results of a single center sample survey; J Urol; 2011; 588-592; 185.
Levin, PJ, et al.; Psychosocial factors related to the use of InterStim(R) for the treatment of refractory overactive bladder; Female Pelvic Med Reconstr Surg; 2014; 272-275; 20;Abstract.
Levin, PJ, et al.; The efficacy of posterior tibial nerve stimulation for the treatment of overactive bladder in women: a systematic review; Int Urogynecol J; 2012; 1591-1597; 23.
Levy, RM; The evolving definition of neuromodulation; Neuromodulation; 2014; 207-210; 17.
Lewis, JM, et al.; Non-traditional management of the neurogenic bladder: tissue engineering and neuromodulation; ScientificWorldJournal; 2007; 1230-1241; 7.
Liao, KK, et al.; Effect of sacral neuromodulation on the spinal nociceptive reflex of patients with idiopathic overactive bladder; Neuromodulation; 2008; 50-55; 11.
Liberman, D, et al.; Concerns regarding sacral neuromodulation as a treatment option for medical-refractory overactive bladder; Can Urol Assoc J; 2011; 285-287; 5.
Lin, YT, et al.; Effects of pudendal neuromodulation on bladder function in chronic spinal cord-injured rats; J Formos Med Assoc; 2015.
Linares Quevedo, AI, et al.; [Posterior sacral root neuromodulation in the treatment of chronic urinary dysfunction]; Actas Urol Esp; 2002; 250-260; 26;Abstract.
Lippmann, QK, et al.; Successful use of sacral neuromodulation in a 12-year-old with cerebral palsy and neurogenic bladder; Neuromodulation; 2014; 396-398; 17.
Lombardi, G, et al.; Clinical concomitant benefits on pelvic floor dysfunctions after sacral neuromodulation in patients with incomplete spinal cord injury; Spinal Cord; 2011; 629-636; 49.

(56) References Cited

OTHER PUBLICATIONS

Lombardi, G, et al.; Clinical female sexual outcome after sacral neuromodulation implant for lower urinary tract symptom (LUTS); J Sex Med; 2008; 1411-1417; 5.

Lombardi, G, et al.; Clinical outcome of sacral neuromodulation in incomplete spinal cord injured patients suffering from neurogenic lower urinary tract symptoms; Spinal Cord; 2009; 486-491; 47.

Lombardi, G, et al.; Clinical outcome of sacral neuromodulation in incomplete spinal cord-injured patients suffering from neurogenic bowel dysfunctions; Spinal Cord; 2010; 154-159; 48.

Lombardi, G, et al.; Intravesical electrostimulation versus sacral neuromodulation for incomplete spinal cord patients suffering from neurogenic non-obstructive urinary retention; Spinal Cord; 2013; 571-578; 51.

Lombardi, G, et al.; Sacral neuromodulation and female sexuality; Int Urogynecol J; 2015; 1751-1757; 26.

Lombardi, G, et al.; Sacral neuromodulation for lower urinary tract dysfunction and impact on erectile function; J Sex Med; 2008; 2135-2140; 5.

Lombardi, G, et al.; Sacral neuromodulation for neurogenic non-obstructive urinary retention in incomplete spinal cord patients: a ten-year follow-up single-centre experience; Spinal Cord; 2014; 241-245; 52.

Lopez-Delgado, A, et al.; Effect on anal pressure of percutaneous posterior tibial nerve stimulation for faecal incontinence; Colorectal Dis; 2014; 533-537; 16.

Lowette, K, et al.; Role of corticosterone in the murine enteric nervous system during fasting; Am J Physiol Gastrointest Liver Physiol; 2014; G905-913; 307.

Lyon, TD, et al.; Pudendal but not tibial nerve stimulation inhibits bladder contractions induced by stimulation of pontine micturition center in cats; Am J Physiol Regul Integr Comp Physiol; 2016; R366-374; 310.

M. Matsushita et al.; Primary somatosensory evoked magnetic fields elicited by sacralsurface electrical stimulation; Neuroscience Letters; 2008; 77?80; 431.

Madersbacher, H, et al.; What are the causes and consequences of bladder overdistension? ICI-RS 2011; Neurourol Urodyn; 2012; 317-321; 31.

Madersbacher, H; Overactive bladder—a practical approach to evaluation and management; J Med Liban; 2004; 220-226; 52;Abstract.

Maeda, Y, et al.; Sacral nerve stimulation for faecal incontinence and constipation: a European consensus statement; Colorectal Dis; 2015; O74-87; 17.

Shen, B, et al.; Neuromodulation of bladder activity by stimulation of feline pudendal nerve using a transdermal amplitude modulated signal (TAMS); Neurourol Urodyn; 2011; 1686-1694; 30.

Shepherd, JP, et al.; InterStim Sacral Neuromodulation and Botox Botulinum—A Toxin Intradetrusor Injections for Relactory Urge Urinary Incontinence: A Decision Analysis Comparing Outcomes Including Efficacy and Complications; Female Pelvic Med Reconstr Surg; 2011; 199-203; 17;Abstract.

Sherif, H, et al.; Posterior tibial nerve stimulation as treatment for the overactive bladder; Arab J Urol; 2013; 131-135; 11.

Sheriff, MK, et al.; Neuromodulation of detrusor hyper-reflexia by functional magnetic stimulation of the sacral roots; Br J Urol; 1996; 39-46; 78;Abstract.

Sherman, ND, et al.; Current and future techniques of neuromodulation for bladder dysfunction; Curr Urol Rep; 2007; 448-454; 8.

Sherman, ND, et al.; Sacral neuromodulation for the treatment of refractory urinary urge incontinence after stress incontinence surgery; Am J Obstet Gynecol; 2005; 2083-2087; 193.

Sherman, ND, et al.; The current use of neuromodulation for bladder dysfunction; Minerva Ginecol; 2006; 283-293; 58;Abstract.

Shi, P, et al.; Bladder response to acute sacral neuromodulation while treating rats in different phases of complete spinal cord injury: a preliminary study; Int Braz J Urol; 2015; 1194-1201; 41.

Shi, P, et al.; Effects of acute sacral neuromodulation on bladder reflex in complete spinal cord injury rats; Neuromodulation; 2013; 583-589; discussion 589; 16.

Shvarts, PG, et al.; [The modern methods of the electrical stimulation for the management of neurogenic disturbances of urination]; Vopr Kurortol Fizioter Lech Fiz Kult; 2015; 18-21; 92.

Siegel, S, et al.; Results of a prospective, randomized, multicenter study evaluating sacral neuromodulation with InterStim therapy compared to standard medical therapy at 6-months in subjects with mild symptoms of overactive bladder, Neurourol Urodyn; 2015; 224-230; 34.

Sievert, KD, et al.; [Unconventional treatment procedures of the bladder in paraplegia and myelomeningocele]; Urologe A; 2012; 1692-1696; 51.

Sievert, KD, et al.; Early sacral neuromodulation prevents urinary incontinence after complete spinal cord injury; Ann Neurol; 2010; 74-84; 67.

Sievert, KD; Neuromodulation; Neurourol Urodyn; 2005; 310; 24.

Signorello, D, et al.; Impact of sacral neuromodulation on female sexual function and his correlation with clinical outcome and quality of life indexes: a monocentric experience; J Sex Med; 2011; 1147-1155; 8.

Sillen, U, et al.; Effects of transcutaneous neuromodulation (TENS) on overactive bladder symptoms in children: a randomized controlled trial; J Pediatr Urol; 2014; 1100-1105; 10.

Silveri, M, et al.; Voiding dysfunction in x-linked adrenoleukodystrophy: symptom score and urodynamic findings; J Urol; 2004; 2651-2653; 171.

Sivalingam, N, et al.; Concepts in the management of the overactive bladder in women; Med J Malaysia; 2012; 137-141; quiz 142; 67.

Skobejko-Wlodarska, L; [Non-neurogenic lower urinary tract dysfunction]; Pol Merkur Lekarski; 2008; 131-137; 24 Suppl 4;Abstract.

Smaldone, MC, et al.; Neuromodulation versus neurotoxin for the treatment of refractory detrusor overactivity: for neurotoxin; Nat Clin Pract Urol; 2008; 120-121; 5.

Smith, AL, et al.; Contemporary management of overactive bladder; Postgrad Med; 2012; 104-116; 124;Abstract.

Smits, MA, et al.; [Neuromodulation as a treatment for overactive bladder syndrome]; Ned Tijdschr Geneeskd; 2012; A4135; 156;Abstract.

Smits, MA, et al.; Sacral neuromodulation in patients with idiopathic overactive bladder after initial botulinum toxin therapy; J Urol; 2013; 2148-2152; 190.

Snellings, AE, et al.; Effects of stimulation site and stimulation parameters on bladder inhibition by electrical nerve stimulation; BJU Int; 2012; 136-143; 110.

South, MM, et al.; Detrusor overactivity does not predict outcome of sacral neuromodulation test stimulation; Int Urogynecol J Pelvic Floor Dysfunct; 2007; 1395-1398; 18.

Speer, LM, et al.; Chronic Pelvic Pain in Women; Am Fam Physician; 2016; 380-387; 93.

Spinelli, M, et al.; A new minimally invasive procedure for pudendal nerve stimulation to treat neurogenic bladder: description of the method and preliminary data; Neurourol Urodyn; 2005; 305-309; 24.

Spinelli, M, et al.; Latest technologic and surgical developments in using InterStim Therapy for sacral neuromodulation: impact on treatment success and safety; Eur Urol; 2008; 1287-1296; 54.

Spinelli, M, et al.; New sacral neuromodulation lead for percutaneous implantation using local anesthesia: description and first experience; J Urol; 2003; 1905-1907; 170.

Srivastava, D; Efficacy of sacral neuromodulation in treating chronic pain related to painful bladder syndrome/interstitial cystitis in adults; J Anaesthesiol Clin Pharmacol; 2012; 428-435; 28.

Starkman, JS, et al.; Management of refractory urinary urge incontinence following urogynecological surgery with sacral neuromodulation; Neurourol Urodyn; 2007; 29-35; discussion 36; 26.

Starkman, JS, et al.; Refractory overactive bladder after urethrolysis for bladder outlet obstruction: management with sacral neuromodulation; Int Urogynecol J Pelvic Floor Dysfunct; 2008; 277-282; 19.

Starkman, JS, et al.; Surgical options for drug-refractory overactive bladder patients; Rev Urol; 2010; e97-e110; 12.

Starkman, JS, et al.; The evolution of obstruction induced overactive bladder symptoms following urethrolysis for female bladder outlet obstruction; J Urol; 2008; 1018-1023; 179.

(56) References Cited

OTHER PUBLICATIONS

Steanu, ID, et al.; The Place of the Ice Water Test (IWT) in the Evaluation of the Patients with Traumatic Spinal Cord Injury; Maedica (Buchar); 2012; 125-130; 7.
Stephany, HA, et al.; Prospective evaluation of sacral nerve modulation in children with validated questionnaires; J Urol; 2013; 1516-1522; 190.
Stoffel, JT; Contemporary management of the neurogenic bladder for multiple sclerosis patients; Urol Clin North Am; 2010; 547-557; 37.
Su, X, et al.; Comparison of neural targets for neuromodulation of bladder micturition reflex in the rat; Am J Physiol Renal Physiol; 2012; F1196-1206; 303.
Su, X, et al.; Differentiation and interaction of tibial versus spinal nerve stimulation for micturition control in the rat; Neurourol Urodyn; 2015; 92-97; 34.
Su, X, et al.; Neuromodulation attenuates bladder hyperactivity in a rat cystitis model; BMC Urol; 2013; 70; 13.
Su, X, et al.; Neuromodulation in a rat model of the bladder micturition reflex; Am J Physiol Renal Physiol; 2012; F477-486; 302.
Su, X, et al.; Optimization of Neuromodulation for Bladder Control in a Rat Cystitis Model; Neuromodulation; 2016; 101-107; 19.
Su, X, et al.; Preclinical assessment of potential interactions between botulinum toxin and neuromodulation for bladder micturition reflex; BMC Urol; 2015; 50; 15.
Su, X, et al.; Quantification of effectiveness of bilateral and unilateral neuromodulation in the rat bladder rhythmic contraction model; BMC Urol; 2013; 34; 13.
Su, X, et al.; Role of the endogenous opioid system in modulation of urinary bladder activity by spinal nerve stimulation; Am J Physiol Renal Physiol; 2013; F52-60; 305.
Sullivan, J, et al.; Overactive detrusor; Curr Opin Urol; 1999; 291-296; 9.
Sullivan, J, et al.; The overactive bladder: neuropharmacological basis of clinical management; Curr Opin Obstet Gynecol; 1999; 477-483; 11.
Sun, Y, et al.; Effects of neural blocking agents on motor activity and secretion in the proximal and distal rat colon: evidence of marked segmental differences in nicotinic receptor activity; Scand J Gastroenterol; 2000; 380-388; 35.
Suskind, AM, et al.; Physician Use of Sacral Neuromodulation Among Medicare Beneficiaries With Overactive Bladder and Urinary Retention; Urology; 2015; 30-34; 86.
Suskind, AM, et al.; Understanding the dissemination of sacral neuromodulation; Surg Innov; 2013; 625-630; 20.
Del Popolo, G, et al.; [Standard pharmacological treatment and new therapies for overactive bladder]; Urologia; 2012; 42534; 79.
Denzinger, S, et al.; Does sacral neuromodulation lead to relevant reduction in the need for intermittent catheterization? A single-center experience on patients with chronic urinary retention; Neuromodulation; 2012; 586-591; discussion 591; 15.
Desrosiers, L, et al.; Urogynecologic conditions: interstitial cystitis/painful bladder syndrome; FP Essent; 2015; 17-22; 430;Abstract.
Devane, LA, et al.; Acute lumbosacral nerve stimulation does not affect anorectal motor function in a rodent model; Neurogastroenterol Motil; 2016; 358-363; 28.
Devroede, G, et al.; Quality of life is markedly improved in patients with fecal incontinence after sacral nerve stimulation; Female Pelvic Med Reconstr Surg; 2012; 103-112; 18;Abstract.
Di Giovangiulio, M, et al.; The Neuromodulation of the Intestinal Immune System and Its Relevance in Inflammatory Bowel Disease; Front Immunol; 2015; 590; 6.
Dijkema, HE, et al.; [Initial experiences with neuromodulation as treatment for incontinence and micturition disorders in The Nethedands]; Ned Tijdschr Geneeskd; 1992; 88-90; 136;Abstract.
Dijkema, HE, et al.; Neuromodulation of sacral nerves for incontinence and voiding dysfunctions Clinical results and complications; Eur Urol; 1993; 72-76; 24;Abstract.

Dmochowski, R; Neuromodulation and the urinary tract—are we over the rainbow or have we simply stepped through the looking glass?; J Urol; 2007; 1844-1845; 178.
Donon, L, et al.; [Sacral neuromodulation: results of a monocentric study of 93 patients]; Prog Urol; 2014; 1120-1131; 24;Abstract.
Dorflinger, A, et al.; Voiding dysfunction; Curr Opin Obstet Gynecol; 2001; 507-512; 13.
Doumouchtsis, SK, et al.; Female voiding dysfunction; Obstet Gynecol Surv; 2008; 519-526; 63.
Drake, Mj; Management and rehabilitation of neurologic patients with lower urinary tract dysfunction; Handb Clin Neurol; 2015; 451-468; 130.
Drossaerts, J, et al.; Screening for depression and anxiety in patients with storage or voiding dysfunction: A retrospective cohort study predicting outcome of sacral neuromodulation; Neurourol Urodyn; 2015;Abstract.
Drossaerts, J, et al.; The value of urodynamic tools to guide patient selection in sacral neuromodulation; World J Urol; 2015; 1889-1895; 33.
Dudding, TC, et al.; Sacral nerve stimulation for faecal incontinence: optimizing outcome and managing complications; Colorectal Dis; 2011; e196-202; 13.
Dudding, TC, et al.; Sacral nerve stimulation for faecal incontinence: patient selection, service provision and operative technique; Colorectal Dis; 2011; e187-195; 13.
Dudding, TC, et al.; Sacral nerve stimulation: an effective treatment for chronic functional anal pain?; Colorectal Dis; 2013; 1140-1144; 15.
Dudding, TC; Future indications for sacral nerve stimulation; Colorectal Dis; 2011; 23-28; 13 Suppl 2.
Duelund-Jakobsen, J, et al.; Baseline factors predictive of patient satisfaction with sacral neuromodulation for idiopathic fecal incontinence; Int J Colorectal Dis; 2014; 793-798; 29.
Duthie, J, et al.; Botulinum toxin injections for adults with overactive bladder syndrome; Cochrane Database Syst Rev; 2007; Cd005493; Abstract.
Duthie, JB, et al.; Botulinum toxin injections for adults with overactive bladder syndrome; Cochrane Database Syst Rev; 2011; Cd005493.
Duve, H, et al.; Distribution and functional significance of Leu-callatostatins in the blowfly Calliphora vomitoria; Cell Tissue Res; 1994; 367-379; 276.
Dwyer, ME, et al.; The dysfunctional elimination syndrome in children—is sacral neuromodulation worth the trouble? J Urol; 2012; 1076-1077; 188.
Elkelini, MS, et al.; Mechanism of action of sacral nerve stimulation using a transdermal amplitude-modulated signal in a spinal cord injury rodent model; Can Urol Assoc J; 2012; 227-230; 6.
Elkelini, MS, et al.; Safety of MRI at 1.51 esla in patients with implanted sacral nerve neurostimulator; Eur Urol 2006; 311-316; 50.
Ellsworth, P, et al.; Neurogenic detrusor overactivity: an update on management options; R I Med J (2013); 2013; 38-40; 96.
Ellsworth, P, et al.; Update on the pharmacologic management of overactive bladder: the present and the future; Urol Nurs; 2010; 29-38, 53; 30.
Elneil, S, et al.; Optimizing the duration of assessment of stage-1 sacral neuromodulation in nonobstructive chronic urinary retention; Neuromodulation; 2014; 66-70; discussion 70-61; 17.
Elneil, S; Urinary retention in women and sacral neuromodulation; Int Urogynecol J; 2010; S475-483; 21 Suppl 2.
Elser, DM; Stress urinary incontinence and overactive bladder syndrome: current options and new targets for management; Postgrad Med; 2012; 42-49; 124;Abstract.
Evans, RJ; Sacral neuromodulation is an effective treatment for interstitial cystitis/bladder pain syndrome: con; J Urol; 2012; 2044-2045; 188.
Everaert, K, et al.; Sacral nerve stimulation for pelvic floor and bladder dysfunction in adults and children; Neuromodulation; 2005; 186-187; 8.
Everaert, K, et al.; The urodynamic evaluation of neuromodulation in patients with voiding dysfunction; Br J Urol; 1997; 702-707; 79.

(56) References Cited

OTHER PUBLICATIONS

Evers, J, et al.; Effects of stimulation frequency and intensity in sacral neuromodulation on anorectal inputs to the somatosensory cortex in an experimental model; Br J Surg; 2014; 1317-1328; 101.
Evers, J, et al.; Reversal of sensory deficit through sacral neuromodulation in an animal model of fecal incontinence; Neurogastroenterol Motil; 2016;Abstract.
Fall, M, et al.; EAU guidelines on chronic pelvic pain; Eur Urol; 2004; 681-689; 46.
Fall, M, et al.; EAU guidelines on chronic pelvic pain; Eur Urol; 2010; 35-48; 57.
Falletto, E, et al.; Is sacral nerve stimulation an effective treatment for chronic idiopathic anal pain?; Dis Colon Rectum; 2009; 456-462; 52.
Falletto, E, et al.; Sacral neuromodulation for bowel dysfunction: a consensus statement from the Italian group; Tech Coloproctol; 2014; 53-64; 18.
Fang, Q, et al.; [Morphological study on the role of ICC-like cells in detrusor neuro-modulation of rat urinary bladder]; Zhonghua Wai Ke Za Zhi; 2008; 1542-1545; 46.
Fariello, JY, et al.; Sacral neuromodulation stimulation for IC/PBS, chronic pelvic pain, and sexual dysfunction; Int Urogynecol J; 2010; 1553-1558; 21.
Faucheron, JL, et al.; Sacral neuromodulation for bowel dysfunction; Tech Coloproctol; 2014; 42433; 18.
Faucheron, JL; [Anal incontinence]; Presse Med; 2008; 1447-1462; 37;Abstract.
Feler, CA, et al.; Sacral neuromodulation for chronic pain conditions; Anesthesiol Clin North America; 2003; 785-795; 21.
Felt-Bersma, RJ, et al.; Temperature-controlled radiofrequency energy (SECCA) to the anal canal for the treatment of faecal incontinence offers moderate improvement; Eur J Gastroenterol Hepatol; 2007; 575-580; 19;Abstract.
Ferhi, K, et al.; [Results of sacral posterior neuromodulation on voiding disorders and impact on sexuality based on a single-center study]; Prog Urol; 2008; 160-166; 18;Abstract.
Ferroni, MC, et al.; Role of the brain stem in tibial inhibition of the micturition reflex in cats; Am J Physiol Renal Physiol; 2015; F242-250; 309.
Ferulano, GP, et al.; [Sacral neuromodulation in fecal continence disorders]; Recenti Prog Med; 2002; 403-409; 93; Abstract.
Finazzi-Agro, E, et al.; Percutaneous tibial nerve stimulation produces effects on brain activity: study on the modifications of the long latency somatosensory evoked potentials; Neurourol Urodyn; 2009; 320-324; 28.
Roth, TM; Sacral neuromodulation and cardiac pacemakers; Int Urogynecol J; 2010; 1035-1037; 21.
Roth, TM; Safe Simultaneous Use of Sacral Neuromodulation and Vagal Nerve Stimulation; Female Pelvic Med Reconstr Surg; 2016; e1-2; 22;Abstract.
Roth, TM; Subcapsular relocation for sacral neuromodulation pulse generator implant revision; Neuromodulation; 2010; 145-146; 13.
Roupret, M, et al.; Sacral neuromodulation for refractory detrusor overactivity in women with an artificial urinary sphincter; J Urol; 2004; 236-239; 172.
Rovner, ES; Treatment of urinary incontinence; Curr Urol Rep; 2000; 235-244; 1.
Rufhion, A, et al.; [Sacral root neuromodulation for the treatment of urinary incontinence reported to detrusor hyperactivity]; Neurochirurgie; 2003; 377-382; 49;Abstract.
Ruffion, A, et al.; [Two indications for bilateral neuromodulation]; Prog Urol; 2003; 1394-1396; 13;Abstract.
Saber-Khalaf, M, et al.; Sacral neuromodulation outcomes in male patients with chronic urinary retention Neuromodulation; 2015; 329-334; discussion 334; 18.
Sadiq, A, et al.; Management of neurogenic lower urinary tract dysfunction in multiple sclerosis patients; Curr Urol Rep; 2015; 44; 16.
Sahai, A, et al.; Neurogenic detrusor overactivity in patients with spinal cord injury: evaluation and management; Curr Urol Rep; 2011; 404-412; 12.
Sajadi, KP, et al.; Bladder augmentation and urinary diversion for neurogenic LUTS: current indications; Curr Urol Rep; 2012; 389-393; 13.
Sajadi, KP, et al.; Overactive bladder after sling surgery; Curr Urol Rep; 2010; 366-371; 11.
Sakas, DE, et al.; An introduction to operative neuromodulation and functional neuroprosthetics, the new frontiers of clinical neuroscience and biotechnology; Acta Neurochir Suppl; 2007; 42439; 97;Abstract.
Sancaktar, M, et al.; The outcome of adding peripheral neuromodulation (Stoller afferent neuro-stimulation) to anti-muscarinic therapy in women with severe overactive bladder; Gynecol Endocrinol; 2010; 729-732; 26.
Sanford, MT, et al.; Neuromodulation in neurogenic bladder; Transl Androl Urol; 2016; 117-126; 5.
Scaglia, M, et al.; Fecal incontinence treated with acupuncture—a pilot study; Auton Neurosci; 2009; 89-92; 145.
Scheepens, WA, et al.; [Neuromodulation and neurostimulation in urology]; Ned Tijdschr Geneeskd; 2001; 1730-1734; 145; Abstract.
Scheepens, WA, et al.; Predictive factors for sacral neuromodulation in chronic lower urinary tract dysfunction; Urology; 2002; 598-602; 60.
Scheepens, WA, et al.; Unilateral versus bilateral sacral neuromodulation in patients with chronic voiding dysfunction; J Urol; 2002; 2046-2050; 168.
Scheepens, WA, et al.; Urodynamic results of sacral neuromodulation correlate with subjective improvement in patients with an overactive bladder; Eur Urol; 2003; 282-287; 43.
Scheiner, DA, et al.; [Interstitial cystitis/bladder pain syndrome (IC/BPS)]; Praxis (Bern 1994); 2015; 909-918; 104.
Schijns, O, et al.; Development and characterization of [123I]iodotiagabine for in-vivo GABA-transporter imaging; Nucl Med Commun; 2013; 175-179; 34;Abstract.
Schmidt, RA, et al.; Neurostimulation and neuromodulation: a guide to selecting the right urologic patient; Eur Urol; 1998; 23-26; 34 Suppl 1;Abstract.
Schneider, MP, et al.; Tibial Nerve Stimulation for Treating Neurogenic Lower Urinary Tract Dysfunction: A Systematic Review; Eur Urol; 2015; 859-867; 68.
Schonberger, B; [Bladder dysfunction and surgery in the small pelvis. Therapeutic possibilities]; Urologe A; 2003; 1569-1575; 42.
Schreiber, KL, et al.; Evidence for neuromodulation of enteropathogen invasion in the intestinal mucosa; J Neuroimmune Pharmacol; 2007; 329-337; 2.
Schultz-Lampel, D, et al.; Experimental results on mechanisms of action of electrical neuromodulation in chronic urinary retention; World J Urol; 1998; 301-304; 16.
Schurch, B, et al.; Dysfunction of lower urinary tract in patients with spinal cord injury; Handb Clin Neurol; 2015; 247-267; 130.
Schurch, B, et al.; Electrophysiological recordings during the peripheral nerve evaluation (PNE) test in complete spinal cord injury patients; World J Urol; 2003; 319-322; 20.
Schwalenberg, T, et al.; [Sacral neuromodulation in urology—development and current status]; Aktuelle Urol; 2012; 39-48; 43;Abstract.
Schwen, Z, et al.; Combination of foot stimulation and tolterodine treatment eliminates bladder overactivity in cats; Neurourol Urodyn; 2014; 1266-1271; 33.
Schwen, Z, et al.; Inhibition of bladder overactivity by duloxetine in combination with foot stimulation or WAY-100635 treatment in cats; Am J Physiol Renal Physiol; 2013; F1663-1668; 305.
Schwen, Z, et al.; Involvement of 5-HT3 receptors in pudendal inhibition of bladder overactivity in cats; Am J Physiol Renal Physiol; 2013; F663-671; 305.
Seif, C, et al.; [Pudendal nerve stimulation therapy of the overactive bladder—an alternative to sacral neuromodulation?]; Aktuelle Urol; 2005; 234-238; 36;Abstract.
Seif, C, et al.; [Use of permanent electrodes in the peripheral nerve evaluation test (PNE-Test) in comparison to conventional wire electrodes]; Aktuelle Urol; 2006; 277-280; 37;Abstract.

(56) References Cited

OTHER PUBLICATIONS

Seif, C, et al.; Findings with Bilateral Sacral Neurostimulation: Sixty-two PNE-Tests in Patients with Neurogenic and Idiopathic Bladder Dysfunctions; Neuromodulation; 2004; 141-145; 7.
Seif, C, et al.; Improved sacral neuromodulation in the treatment of the hyperactive detrusor: signal modification in an animal model; BJU Int; 2003; 711-715; 91.
Seth, A, et al.; What's new in the diagnosis and management of painful bladder syndrome/interstitial cystitis?; Curr Urol Rep; 2008; 349-357; 9.
Sevcencu, C; A review of electrical stimulation to treat motility dysfunctions in the digestive tract: effects and stimulation patterns; Neuromodulation; 2007; 85-99; 10.
Sevcencu, C; Gastrointestinal mechanisms activated by electrical stimulation to treat motility dysfunctions in the digestive tract: a review; Neuromodulation; 2007; 100-112; 10.
Shafik, A, et al.; Percutaneous peripheral neuromodulation in the treatment of fecal incontinence; Eur Surg Res; 2003; 103-107; 35.
Shah, P, et al.; Unique spatiotemporal neuromodulation of the lumbosacral circuitry shapes locomotor success after spinal cord injury; J Neurotrauma; 2016;Abstract.
Shaker, H, et al.; Role of C-afferent fibres in the mechanism of action of sacral nerve root neuromodulation in chronic spinal cord injury; BJU Int; 2000; 905-910; 85.
Shaker, H, et al.; Sacral root neuromodulation in the treatment of various voiding and storage problems; Int Urogynecol J Pelvic Floor Dysfunct; 1999; 336-343; 10;Abstract.
Shaker, HS, et al.; Sacral nerve root neuromodulation: an effective treatment for refractory urge incontinence; J Urol; 1998; 1516-1519; 159.
Shaker, HS, et al.; Sacral root neuromodulation in idiopathic nonobstructive chronic urinary retention; J Urol; 1998; 1476-1478; 159.
Shalom, DF, et al.; Sacral nerve stimulation reduces elevated urinary nerve growth factor levels in women with symptomatic detrusor overactivity; Am J Obstet Gynecol; 2014; 561.e561-565; 211.
Shamliyan, T, et al.; Prevention of urinary and fecal incontinence in adults; Evid Rep Technol Assess (Full Rep); 2007; 1-379; ;Abstract.
Sharma, A, et al.; Review of sacral neuromodulation for management of constipation; Surg Innov; 2013; 614-624; 20.
Sharma, A, et al.; Sacral neuromodulation for the management of severe constipation: development of a constipation treatment protocol; Int J Colorectal Dis; 2011; 1583-1587; 26.
Gupta, P, et al.; Percutaneous tibial nerve stimulation and sacral neuromodulation: an update; Curr Urol Rep; 2015; 4; 16.
Guys, JM, et al.; [Neurogenic bladder in children: basic principles in diagnosis and treatment]; Ann Urol (Paris); 2006; 15-27; 40;Abstract.
Guys, JM, et al.; Sacral neuromodulation for neurogenic bladder dysfunction in children; J Urol; 2004; 1673-1676; 172.
Haddad, M, et al.; Sacral neuromodulation in children with urinary and fecal incontinence: a multicenter, open label, randomized, crossover study; J Urol; 2010; 696-701; 184.
Hamann, MF, et al.; [Urinary incontinence in men and women. Diagnostics and conservative therapy]; Urologe A; 2014; 1073-1084; quiz 1085-1076; 53.
Hartmann, KE, et al.; Treatment of overactive bladder in women; Evid Rep Technol Assess (Full Rep); 2009; 1-120, v.
Hasan, ST, et al.; Neuromodulation in bladder dysfunction; Curr Opin Obstet Gynecol; 1998; 395-399; 10.
Hasan, ST, et al.; Surface localization of sacral foramina for neuromodulation of bladder function. An anatomical study; Eur Urol; 1996; 90-98; 29;Abstract.
Hasan, ST, et al.; Transcutaneous electrical nerve stimulation and temporary S3 neuromodulation in idiopathic detrusor instability; J Urol; 1996; 2005-2011; 155.
Hashim, H, et al.; Drug treatment of overactive bladder: efficacy, cost and quality-of-life considerations; Drugs; 2004; 1643-1656; 64.
Hashim, H, et al.; Novel uses for antidiuresis; Int J Clin Pract Suppl; 2007; 32-36; Abstract.
Hashim, H, et al.; Patient preferences for treating refractory overactive bladder in the UK; Int Urol Nephrol; 2015; 1619-1627; 47.
Hassouna, M, et al.; Dog as an animal model for neurostimulation; Neurourol Urodyn; 1994; 159-167; 13.
Hassouna, M, et al.; Update on sacral neuromodulation: indications and outcomes; Curr Urol Rep; 2003; 391-398; 4.
Hassouna, M; Sacral neuromodulation for overactive bladder: Is it worth it?; Can Urol Assoc J; 2013; E454; 7.
Hassouna, MM, et al.; Economic evaluation of sacral neuromodulation in overactive bladder: A Canadian perspective; Can Urol Assoc J; 2015; 242-247; 9.
Hedlund, H, et al.; Sacral neuromodulation in Norway: clinical experience of the first three years; Scand J Urol Nephrol Suppl; 2002; 87-95; Abstract.
Heinze, K, et al.; [Neuromodulation—new techniques]; Urologe A; 2015; 373-377; 54.
Hellstrom, PA, et al.; Sacral nerve stimulation lead implantation using the O-arm; BMC Urol; 2013; 48; 13.
Herbison, GP, et al.; Sacral neuromodulation with implanted devices for urinary storage and voiding dysfunction in adults; Cochrane Database Syst Rev; 2009; Cd004202.
Hersh, L, et al.; Clinical management of urinary incontinence in women; Am Fam Physician; 2013; 634-640; 87.
Hijaz, A, et al.; Complications and troubleshooting of two-stage sacral neuromodulation therapy: a single-institution experience; Urology; 2006; 533-537; 68.
Hill, AJ, et al.; Resolution of Chronic Vulvar Pruritus With Replacement of a Neuromodulation Device; J Minim nvasive Gynecol; 2015; 889-891; 22.
Hindley, RG, et al.; The 2-year symptomatic and urodynamic results of a prospective randomized trial of interstitial radiofrequency therapy vs transurethral resection of the prostate; BJU Int; 2001; 217-220; 88.
Hoag, N, et al.; Underactive Bladder: Clinical Features, Urodynamic Parameters, and Treatment; Int Neurourol J; 2015; 185-189; 19.
Hoch, M, et al.; [Chemical destruction of sacral nerve roots by alcohol injection for the treatment of overactive bladder]; Prog Urol; 2006; 584-587; 16;Abstract.
Hoda, MR, et al.; [Sacral neuromodulation in urology. The emperor's new clothes or effective high-tech medicine?]; Urologe A; 2010; 1254-1259; 49.
Hoebeke, P, et al.; Transcutaneous neuromodulation for the urge syndrome in children: a pilot study; J Urol; 2001; 2416-2419; 166.
Hohenfellner, M, et al.; [Sacral neuromodulation of the urinary bladder]; Urologe A; 2000; 55-63; 39.
Hohenfellner, M, et al.; Bilateral chronic sacral neuromodulation for treatment of lower urinary tract dysfunction; J Urol; 1998; 821-824; 160.
Hohenfellner, M, et al.; Chronic sacral neuromodulation for treatment of neurogenic bladder dysfunction: long-term results with unilateral implants; Urology; 2001; 887-892; 58.
Hohenfellner, M, et al.; Sacral neuromodulation for treatment of lower urinary tract dysfunction; BJU Int; 2000; 10-19; discussion 22-13; 85 Suppl 3.
Hoque, T, et al.; Validation of internal controls for gene expression analysis in the intestine of rats infected with Hymenolepis diminuta; Parasitol Int; 2007; 325-329; 56.
Horrocks, EJ, et al.; Double-blind randomised controlled trial of percutaneous tibial nerve stimulation versus sham electrical stimulation in the treatment of faecal incontinence: CONtrol of Faecal Incontinence using Distal NeuromodulaTion (the CONFIDeNT trial); Health Technol Assess; 2015; 1-164; 19.
Hotouras, A, et al.; Prospective clinical audit of two neuromodulatory treatments for fecal incontinence: sacral nerve stimulation (SNS) and percutaneous tibial nerve stimulation (PTNS); Surg Today; 2014; 2124-2130; 44.
Hoyle, CH, et al.; Ethylcholine mustard aziridinium ion (AF64A) impairs cholinergic neuromuscular transmission in the guinea-pig ileum and urinary bladder, and cholinergic neuromodulation in the enteric nervous system of the guinea-pig distal colon; Gen Pharmacol; 1986; 543-548; 17.
Hubsher, CP, et al.; Sacral nerve stimulation for neuromodulation of the lower urinary tract; Can J Urol; 2012; 3480-6484; 19.

(56) References Cited

OTHER PUBLICATIONS

Hull, T, et al.; Long-term durability of sacral nerve stimulation therapy for chronic fecal incontinence; Dis Colon Rectum; 2013; 234-245; 56.
Hull, TL; Sacral neuromodulation stimulation in fecal incontinence; Int Urogynecol J; 2010; 1565-1568; 21.
Humphreys, MR, et al.; Preliminary results of sacral neuromodulation in 23 children; J Urol; 2006; 2227-2231; 176.
Hyun, SJ, et al.; Comparative analysis between thoracic spinal cord and sacral neuromodulation in a rat spinal cord injury model: a preliminary report of a rat spinal cord stimulation model; Korean J Spine; 2013; 14-18; 10.
Iarumov, N, et al.; [Anal incontinence—new methods of surgical treatment using artificial bowel sphincter and sacral nerve stimulation]; Khirurgiia (Sofiia); 2007; 40-45; ;Abstract.
Indar, A, et al.; A dual benefit of sacral neuromodulation; Surg Innov; 2008; 219-222; 15.
Indinnimeo, M, et al.; Sacral neuromodulation for the treatment of fecal incontinence: analysis of cost-effectiveness; Dis Colon Rectum; 2010; 1661-1669; 53.
Ingber, MS, et al.; Neuromodulation and female sexual function: does treatment for refractory voiding symptoms have an added benefit?; Int Urogynecol J Pelvic Floor Dysfunct; 2009; 1055-1059; 20.
Iqbal, F, et al.; Bilateral transcutaneous tibial nerve stimulation for chronic constipation; Colorectal Dis; 2016; 173-178; 18.
Ishigooka, M, et al.; Sacral nerve stimulation and diurnal urine volume; Eur Urol; 1999; 421-426; 36;Abstract.
J. Groen and J.L.H.R. Bosch; Neuromodulation techniques in the treatment of the overactive bladder; BJU International (2001), 87, 723-731.
Jacobs, SA, et al.; Randomized prospective crossover study of interstim lead wire placement with curved versus straight stylet; Neurourol Urodyn; 2014; 488-492; 33.
Jadav, AM, et al.; Does sacral nerve stimulation improve global pelvic function in women?; Colorectal Dis; 2013; 848-857; 15.
Van Koeveringe, GA, et al.; Detrusor underactivity: a plea for new approaches to a common bladder dysfunction; Neurourol Urodyn; 2011; 723-728; 30.
Van Ophoven, A, et al.; [The future of invasive neuromodulation: new techniques and expanded indications]; Urologe A; 2012; 212-216; 51.
Van Voskuilen, AC, et al.; Long term results of neuromodulation by sacral nerve stimulation for lower urinary tract symptoms: a retrospective single center study; Eur Urol; 2006; 366-372; 49.
Van Voskuilen, AC, et al.; Medium-term experience of sacral neuromodulation by tined lead implantation; BJU Int; 2007; 107-110; 99.
Van Wunnik, BP, et al.; Cost-effectiveness analysis of sacral neuromodulation for faecal incontinence in The Netherlands; Colorectal Dis; 2012; e807-814; 14.
Van Wunnik, BP, et al.; Neuromodulation for constipation: sacral and transcutaneous stimulation; Best Pract Res Clin Gastroenterol; 2011; 181-191; 25.
Van Wunnik, BP, et al.; Patient experience and satisfaction with sacral neuromodulation: results of a single-center sample survey; Dis Colon Rectum; 2011; 95-100; 54.
Van Wunnik, BP, et al.; Sacral neuromodulation therapy: a promising treatment for adolescents with refractory functional constipation; Dis Colon Rectum; 2012; 278-285; 55.
Vasavada, SP, et al.; Neuromodulation techniques: a comparison of available and new therapies; Curr Urol Rep; 2007; 455-460; 8.
Vasdev, N, et al.; The surgical management of the refractory overactive bladder; Indian J Urol; 2010; 263-269; 26.
Veeratterapillay, R, et al.; Augmentation cystoplasty: Contemporary indications, techniques and complications; Indian J Urol; 2013; 322-327; 29.
Veit-Rubin, N, et al.; [Overactive bladder syndrome—a public health challenge]; Rev Med Suisse; 2015; 2016-2021; 11;Abstract.

Mgil, HR, et al.; Urinary tract infection in the neurogenic bladder; Transl Androl Urol; 2016; 72-87; 5.
Vignes, JR, et al.; Animal models of sacral neuromodulation for detrusor overactivity; Neurourol Urodyn; 2009; 12594; 28.
Vignes, JR, et al.; Sacral neuromodulation as a functional treatment of bladder overactivity; Acta Neurochir Suppl; 2007; 315-322; 97;Abstract.
Vignes, JR, et al.; Sacral neuromodulation in lower urinary tract dysfunction; Adv Tech Stand Neurosurg; 2005; 177-224; 30;Abstract.
Nallace, JL, et al.; Lack of beneficial effect of a tachykinin receptor antagonist in experimental colitis; Regul Pept; 1998; 95-101; 73.
Walsh, IK, et al.; Non-invasive antidromic neurostimulation: a simple effective method for improving bladder storage; Neurourol Urodyn; 2001; 73-84; 20.
Walter, S; [Duloxetine. A new preparation for patients with urinary incontinence]; Ugeskr Laeger; 2005; 4553-4555; 167 Abstract.
Wang, Y, et al.; Neuromodulation reduces c-fos gene expression in spinalized rats: a double-blind randomized study; J Urol; 2000; 1966-1970; 163.
Wang, Y, et al.; Neuromodulation reduces urinary frequency in rats with hydrochloric acid-induced cystitis; BJU Int; 2000; 726-730; 86.
Wark, HA, et al.; Restoration from acute urinary dysfunction using Utah electrode arrays implanted into the feline pudendal nerve; Neuromodulation; 2015; 317-323; 18.
Watanabe, JH, et al.; Cost analysis of interventions for antimuscarinic refractory patients with overactive bladder; Urology; 2010; 835-840; 76.
Wehbe, SA, et al.; Minimally invasive therapies for chronic pelvic pain syndrome; Curr Urol Rep; 2010; 276-285; 11.
Wehbe, SA, et al.; Sacral neuromodulations for female lower urinary tract, pelvic floor, and bowel disorders; Curr Opin Obstet Gynecol; 2010; 414-419; 22.
Weil, EH, et al.; Sacral root neuromodulation in the treatment of refractory urinary urge incontinence: a prospective randomized clinical trial; Eur Urol; 2000; 161-171; 37;Abstract.
Wein, AJ, et al.; Overactive bladder: a better understanding of pathophysiology, diagnosis and management; J Urol; 2006; S5-10; 175.
Wein, AJ; Diagnosis and treatment of the overactive bladder; Urology; 2003; 20-27; 62.
Wein, AJ; Re: inhibition of bladder overactivity by a combination of tibial neuromodulation and tramadol treatment in cats; J Urol; 2014; 868-869; 191.
Wein, AJ; Re: is on-demand sacral neuromodulation in patients with OAB syndrome a feasible therapy regime?; J Urol; 2013; 610-611; 189.
Wein, AJ; Re: Results of a Prospective, Randomized, Multicenter Study Evaluating Sacral Neuromodulation with InterStim Therapy Compared to Standard Medical Therapy at 6-Months in Subjects with Mild Symptoms of Overactive Bladder; J Urol; 2015; 1051-1052; 194.
Wenzler, DL, et al.; Proof of concept trial on changes in current perception threshold after sacral neuromodulation; Neuromodulation; 2015; 228-231; discussion 232; 18.
Wexner, SD, et al.; Current surgical strategies to treat fecal incontinence; Expert Rev Gastroenterol Hepatol; 2015; 1577-1589; 9;Abstract.
White, N, et al.; Overactive Bladder; Obstet Gynecol Clin North Am; 2016; 59-68; 43.
Whitmore, KE; Complementary and alternative therapies as treatment approaches for interstitial cystitis; Rev Urol; 2002; S28-35; 4 Suppl 1.
Wiklund, CU, et al.; Modulation of cholinergic and substance P-like neurotransmission by nitric oxide in the guinea-pig ileum; Br J Pharmacol; 1993; 833-839; 110.
Wiklund, NP, et al.; Cholinergic neuromodulation by endothelin in guinea pig ileum; Neurosci Lett; 1989; 342-346; 101.
Wiklund, NP, et al.; Neuromodulation by adenine nucleotides, as indicated by experiments with inhibitors of nucleotide inactivation; Acta Physiol Scand; 1986; 217-223; 126;Abstract.
Williams, MJ, et al.; Self-Reported Medication Costs In Patients Receiving Sacral Neuromodulation For Overactive Bladder; Value Health; 2015; A352; 18.

(56) References Cited

OTHER PUBLICATIONS

Withington, J, et al.; The changing face of urinary continence surgery in England: a perspective from the Hospital Episode Statistics database; BJU Int; 2014; 268-277; 114.
Wolff, K, et al.; Functional outcome and quality of life after stapled transanal rectal resection for obstructed Iefecation syndrome; Dis Colon Rectum; 2010; 881-888; 53.
Wood, LN, et al.; Urinary incontinence in women; Bmj; 2014; g4531; 349.
Wooldridge, LS; Percutaneous tibial nerve stimulation for the treatment of urinary frequency, urinary urgency, and urge incontinence: results from a community-based clinic; Urol Nurs; 2009; 177-185; 29.
Worsoe, J, et al.; Turning off sacral nerve stimulation does not affect gastric and small intestinal motility in patients treated for faecal incontinence; Colorectal Dis; 2012; e713-720; 14.
Wosnitzer, MS, et al.; The use of sacral neuromodulation for the treatment of non-obstructive urinary retention secondary to Guillain-Barre syndrome; Int Urogynecol J Pelvic Floor Dysfunct; 2009; 1145-1147; 20.
Wu, JM, et al.; Patient preferences for different severities of and treatments for overactive bladder; Female Pelvic Med Reconstr Surg; 2011; 184-189; 17;Abstract.
Wyndaele, JJ, et al.; Conservative treatment of the neuropathic bladder in spinal cord injured patients; Spinal Cord; 2001; 294-300; 39.
Wyndaele, JJ, et al.; Influence of sacral neuromodulation on electrosensation of the lower urinary tract; J Urol; 2000; 221-224; 163.
Wyndaele, JJ; Clinical outcome of sacral neuromodulation in incomplete spinal cord injured patients suffering from neurogenic lower urinary tract symptoms; Spinal Cord; 2009; 427; 47.
Xiao, Z, et al.; Role of spinal GABAA receptors in pudendal inhibition of nociceptive and nonnociceptive bladder reflexes in cats; Am J Physiol Renal Physiol; 2014; F781-789; 306.
Xiao, Z, et al.; Somatic modulation of spinal reflex bladder activity mediated by nociceptive bladder afferent nerve fibers in cats; Am J Physiol Renal Physiol; 2014; F673-679; 307.
Yamanishi, T, et al.; Neuromodulation for the Treatment of Lower Urinary Tract Symptoms; Low Urin Tract Symptoms; 2015; 121-132; 7.
Yamanouchi, M, et al.; Integrative control of rectoanal reflex in guinea pigs through lumbar colonic nerves; Am J Physiol Gastrointest Liver Physiol; 2002; G148-156; 283.
Yang, G, et al.; Pudendal nerve stimulation and block by a wireless-controlled implantable stimulator in cats; Neuromodulation; 2014; 490-496; discussion 496; 17.
Yazdany, T, et al.; Determining outcomes, adverse events, and predictors of success after sacral neuromodulation for lower urinary disorders in women; Int Urogynecol J; 2011; 1549-1554; 22.
Yih, JM, et al.; Changes in sexual functioning in women after neuromodulation for voiding dysfunction; J Sex Med; 2013; 2477-2483; 10.

Yogi A. Patel; Kilohertz Electrical Stimulation Nerve Conduction Block: Effects of Electrode Surface Area; IEEE Transactions on Neural Systems and Rehabilitation Engineering, vol. 25, No. 10, Oct. 2017.
Yoong, W, et al.; Neuromodulative treatment with percutaneous tibial nerve stimulation for intractable detrusor instability: outcomes following a shortened 6-week protocol; BJU Int; 2010; 1673-1676; 106.
Yun, AJ, et al.; Opening the floodgates: benign prostatic hyperplasia may represent another disease in the compendium of ailments caused by the global sympathetic bias that emerges with aging; Med Hypotheses; 2006; 392-394; 67.
Zabihi, N, et al.; Short-term results of bilateral S2-S4 sacral neuromodulation for the treatment of refractory interstitial cystitis, painful bladder syndrome, and chronic pelvic pain; Int Urogynecol J Pelvic Floor Dysfunct; 2008; 553-557; 19.
Zariffa, J, et al.; A Phase-Based Electrical Plethysmography Approach to Bladder Volume Measurement; Ann Biomed Eng; 2015.
Zecca, C, et al.; Motor and sensory responses after percutaneous tibial nerve stimulation in multiple sclerosis patients with lower urinary tract symptoms treated in daily practice; Eur J Neurol; 2014; 506-511; 21.
Zecca, C, et al.; Posterior tibial nerve stimulation in the management of lower urinary tract symptoms in patients with multiple sclerosis; Int Urogynecol J; 2015.
Zempleni, MZ, et al.; Cortical substrate of bladder control in SCI and the effect of peripheral pudendal stimulation; Neuroimage; 2010; 2983-2994; 49.
Zhang, F, et al.; Inhibition of bladder overactivity by a combination of tibial neuromodulation and tramadol treatment in cats; Am J Physiol Renal Physiol; 2012; F1576-1582; 302.
Zhang, F, et al.; Neural pathways involved in sacral neuromodulation of reflex bladder activity in cats; Am J Physiol Renal Physiol; 2013; F710-717; 304.
Zhang, N, et al.; Transcutaneous Neuromodulation at Posterior Tibial Nerve and ST36 for Chronic Constipation; Evid Based Complement Alternat Med; 2014; 560802; 2014.
Zhao, X, et al.; Diffused and sustained inhibitory effects of intestinal electrical stimulation on intestinal motility mediated via sympathetic pathway; Neuromodulation; 2014; 373-379; discussion 380; 17.
Zheng, J, et al.; [Sacral neuromodulation in the treatment of intractable constipation]; Zhonghua Wei Chang Wai Ke Za Zhi; 2014; 1175-1178; 17;Abstract.
Zhou, Y, et al.; Change of vanilloid receptor 1 following neuromodulation in rats with spinal cord injury; J Surg Res; 2002; 140-144; 107.
Zullo, MA, et al.; Sacral neuromodulation after stabilization of L2-S1 vertebrae with metallic fixation devices: is it feasible?; Int Urogynecol J; 2011; 373-375; 22.
Zvara, P, et al.; An animal model for the neuromodulation of neurogenic bladder dysfunction; Br J Urol; 1998; 267-271; 82.
International Preliminary Report on Patentability dated Jun. 30, 2022 for PCT/US2020/65235.

* cited by examiner

| Frequency | Duration | | | | | |
|---|---|---|---|---|---|---|
| | 1 | 5 | 10 | 20 | 30 | 50 |
| 1 | 1 | 5 | 10 | 20 | 30 | 50 |
| 5 | 5 | 25 | 50 | 100 | 150 | 250 |
| 20 | 20 | 100 | 200 | 400 | 600 | 1000 |
| 50 | 50 | 250 | 500 | 1000 | 1500 | 2500 |
| 100 | 100 | 500 | 1000 | 2000 | 3000 | 5000 |
| 150 | 150 | 750 | 1500 | 3000 | 4500 | 7500 |

Fig. 7

Obverse        Reverse

[A]        [B]        [C]

NON-INVASIVE NERVE ACTIVATOR WITH BOOSTED CHARGE DELIVERY

CROSS REFERENCE TO RELATED APPLICATIONS

This application claims priority to U.S. Provisional Patent Application Ser. No. 62/948,780, filed on Dec. 16, 2019, the disclosure of which is hereby incorporated by reference.

FIELD

This invention pertains to the activation of nerves by topical stimulators to control or influence muscles, tissues, organs, or sensation, including pain, in mammals, including humans.

BACKGROUND INFORMATION

Nerve disorders may result in loss of control of muscle and other body functions, loss of sensation, or pain. Surgical procedures and medications sometimes treat these disorders but have limitations. This invention pertains to a system for offering other options for treatment and improvement of function.

BRIEF DESCRIPTION OF THE DRAWINGS

FIG. 7 is a table relating charge duration vs. frequency to provide feedback to the adaptive protocol in accordance with one example.

DETAILED DESCRIPTION

A non-invasive nerve activator in accordance with various examples disclosed herein includes novel circuitry to adequately boost voltage to a required level and to maintain a substantially constant level of charge for nerve activation. Further, a feedback loop provides for an automatic determination and adaptation of the applied charge level. Further, examples conserve battery power by selectively using battery power, and form a compact electronic package to facilitate the mounting on a generally small adhesive external patch.

Figure 1:
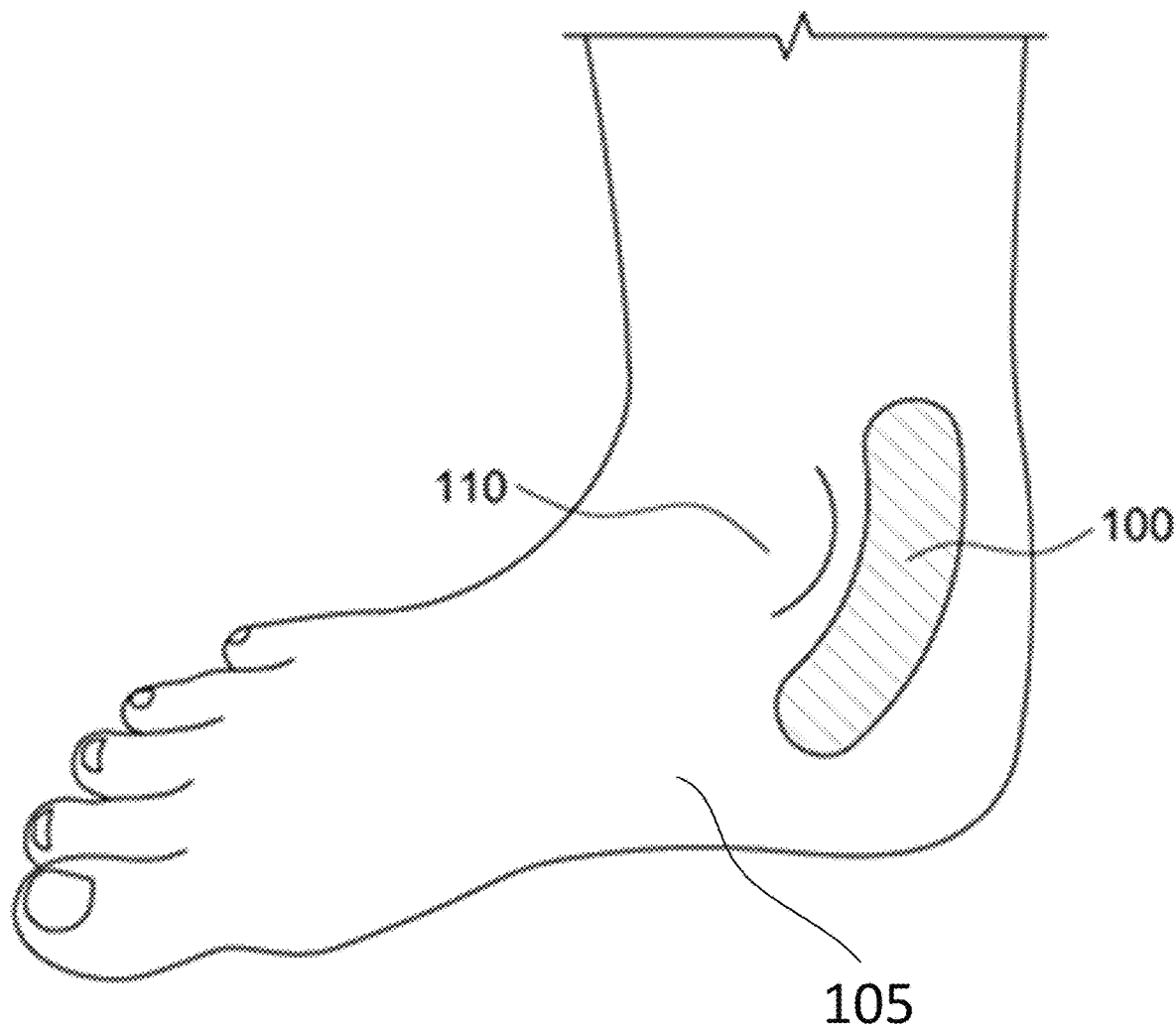
FIG. 1 illustrates an example patch that is affixed to a location behind an ankle bone of a user.

FIG. 1 illustrates an example patch 100, also referred to as a smart band aid or smartpad or Topical Nerve Activator ("TNA") or topical nerve activation patch, that is affixed to a location behind an ankle bone 110 of a user 105. In the example of FIG. 1, patch 100 is adapted to activate/stimulate the tibial nerve of user 105 and can have one shape for the left ankle and a similar but mirrored shape for the right ankle. In other examples, patch 100 is worn at different locations of user 105 to activate the tibial nerve from a different location, or to activate a different nerve of user 105.

Patch 100 is used to stimulate these nerves and is convenient, unobtrusive, self-powered, and may be controlled from a smartphone or other control device. This has the advantage of being non-invasive, controlled by consumers themselves, and potentially distributed over the counter without a prescription. Patch 100 provides a means of stimulating nerves without penetrating the dermis, and can be applied to the surface of the dermis at a location appropriate for the nerves of interest. In examples, patch 100 is applied by the user and is disposable.

Patch 100 in examples can be any type of device that can be fixedly attached to a user, using adhesive in some examples, and includes a processor/controller and instructions that are executed by the processor, or a hardware implementation without software instructions, as well as electrodes that apply an electrical stimulation to the surface of the user's skin, and associated electrical circuitry. Patch 100 in one example provides topical nerve activation/stimulation on the user to provide benefits to the user, such as bladder management for an overactive bladder ("OAB").

Patch 100 in one example can include a flexible substrate, a malleable dermis conforming bottom surface of the substrate including adhesive and adapted to contact the dermis, a flexible top outer surface of the substrate approximately parallel to the bottom surface, a plurality of electrodes positioned on the patch proximal to the bottom surface and located beneath the top outer surface and directly contacting the flexible substrate, electronic circuitry (as disclosed herein) embedded in the patch and located beneath the top outer surface and integrated as a system on a chip that is directly contacting the flexible substrate, the electronic circuitry integrated as a system on a chip and including an electrical signal generator integral to the malleable dermis conforming bottom surface configured to electrically activate the one or more electrodes, a signal activator coupled to the electrical signal generator, a nerve stimulation sensor that provides feedback in response to a stimulation of one or more nerves, an antenna configured to communicate with a remote activation device, a power source in electrical communication with the electrical signal generator, and the signal activator, where the signal activator is configured to activate in response to receipt of a communication with the activation device by the antenna and the electrical signal generator configured to generate one or more electrical stimuli in response to activation by the signal activator, and the electrical stimuli configured to stimulate one or more nerves of a user wearing patch 100 at least at one location proximate to patch 100. Additional details of examples of patch 100 beyond the novel details disclosed herein are disclosed in U.S. Pat. No. 10,016,600, entitled "Topical Neurological Stimulation", the disclosure of which is hereby incorporated by reference.

Figure 2:
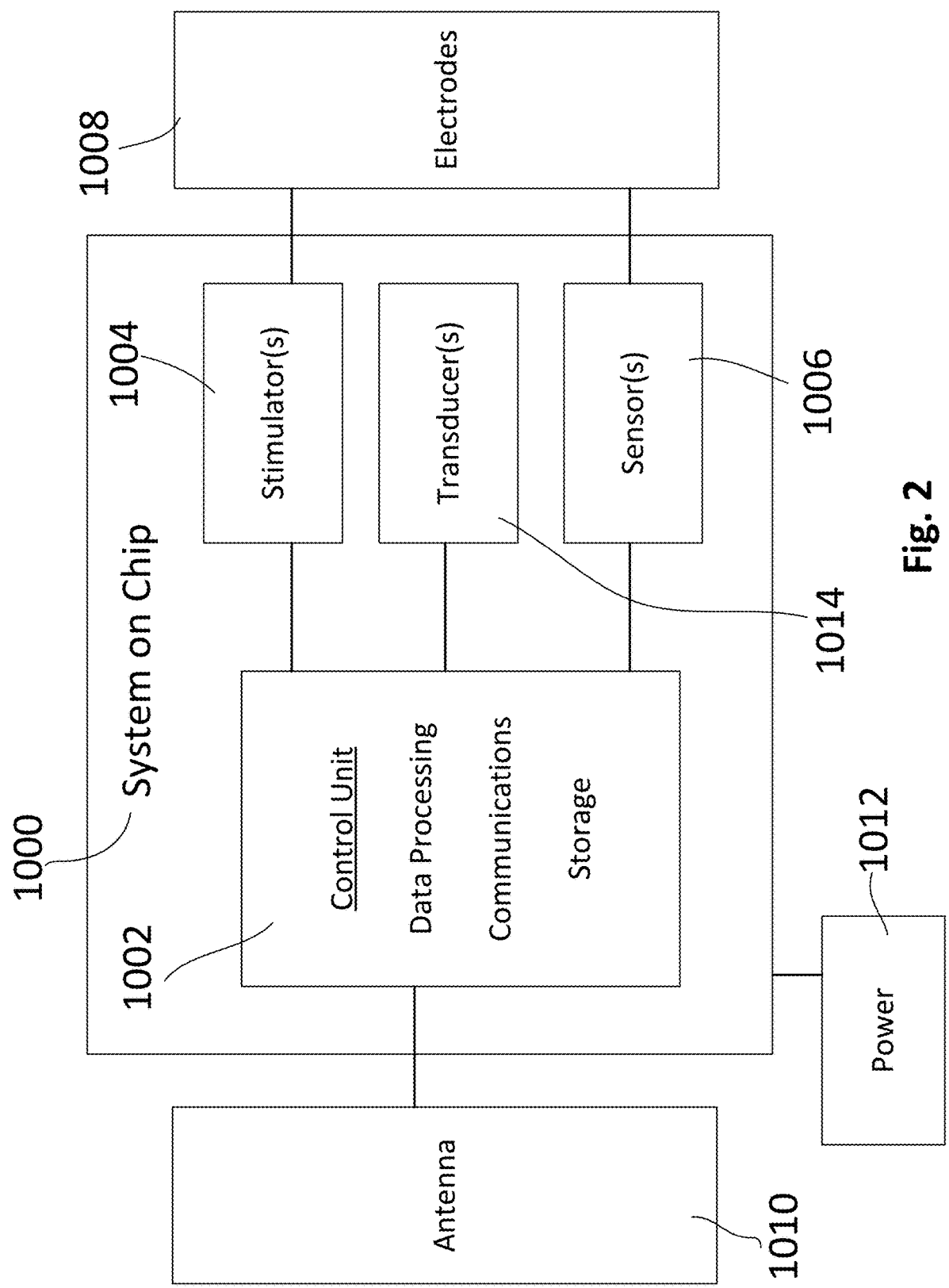
FIG. 2 is a block diagram illustrating hardware/software related elements of an example of the patch of FIG. 1.

FIG. 2 is a block diagram illustrating hardware/software related elements of an example of patch 100 of FIG. 1. Patch 100 includes electronic circuits or chips 1000 that perform the functions of: communications with an external control device, such as a smartphone or fob (which can communicate with patch 100 using wireless communication, such as Bluetooth Low Energy ("BLE")), or external processing such as cloud based processing devices, nerve activation via electrodes 1008 that produce a wide range of electric fields according to a treatment regimen, and a wide range of sensors 1006 such as, but not limited to, mechanical motion and pressure, temperature, humidity, acoustic, chemical and positioning sensors. In another example, patch 100 includes transducers 1014 to transmit signals to the tissue or to receive signals from the tissue.

One arrangement is to integrate a wide variety of these functions into a system on a chip 1000. Within this is shown a control unit 1002 for data processing, communications, transducer interface and storage, and one or more stimulators 1004 and sensors 1006 that are connected to electrodes 1008. Control unit 1002 can be implemented by a general purpose processor/controller, or a specific purpose processor/controller, or a special purpose logical circuit. An antenna 1010 is incorporated for external communications by control unit 1002. Also included is an internal power supply 1012, which may be, for example, a battery. The capacity of the battery may be about 1 mAh to about 100 mAh. Other examples may include an external power supply. It may be necessary to include more than one chip to accommodate a wide range of voltages for data processing and stimulation, or one or more of the functionality may be implemented on its own separate chip/electronic package. Electronic circuits and chips will communicate with each other via conductive tracks within the device capable of transferring data and/or power.

Patch 100 interprets a data stream from control unit 1002 to separate out message headers and delimiters from control instructions. In one example, control instructions include information such as voltage level and pulse pattern. Patch 100 activates stimulator 1004 to generate a stimulation signal to electrodes 1008 placed on the tissue according to the control instructions. In another example, patch 100 activates transducer 1014 to send a signal to the tissue. In another example, control instructions cause information such as voltage level and a pulse pattern to be retrieved from a library stored by patch 100, such as storage within control unit 1002.

Patch 100 receives sensory signals from the tissue and translates them to a data stream that is recognized by control unit 1002. Sensory signals can include electrical, mechanical, acoustic, optical and chemical signals. Sensory signals are received by patch 100 through electrodes 1008 or from other inputs originating from mechanical, acoustic, optical, or chemical transducers. For example, an electrical signal from the tissue is introduced to patch 100 through electrodes 1008, is converted from an analog signal to a digital signal and then inserted into a data stream that is sent through antenna 1010 to the external control device. In another example, an acoustic signal is received by transducer 1014, converted from an analog signal to a digital signal and then inserted into a data stream that is sent through the antenna 1010 to the external control device. In some examples, sensory signals from the tissue are directly interfaced to the external control device for processing.

In examples of patch 100 disclosed above, when being used for therapeutic treatment such as bladder management for OAB, there is a need to control the voltage by boosting the voltage to a selected level and providing the same level of charge upon activation to a mammalian nerve. Further, there is a need to conserve battery life by selectively using battery power. Further, there is a need to create a compact electronics package to facilitate mounting the electronics package on a relatively small mammalian dermal patch in the range of the size of an ordinary adhesive patch or band aid.

Figures 3A, 3B:
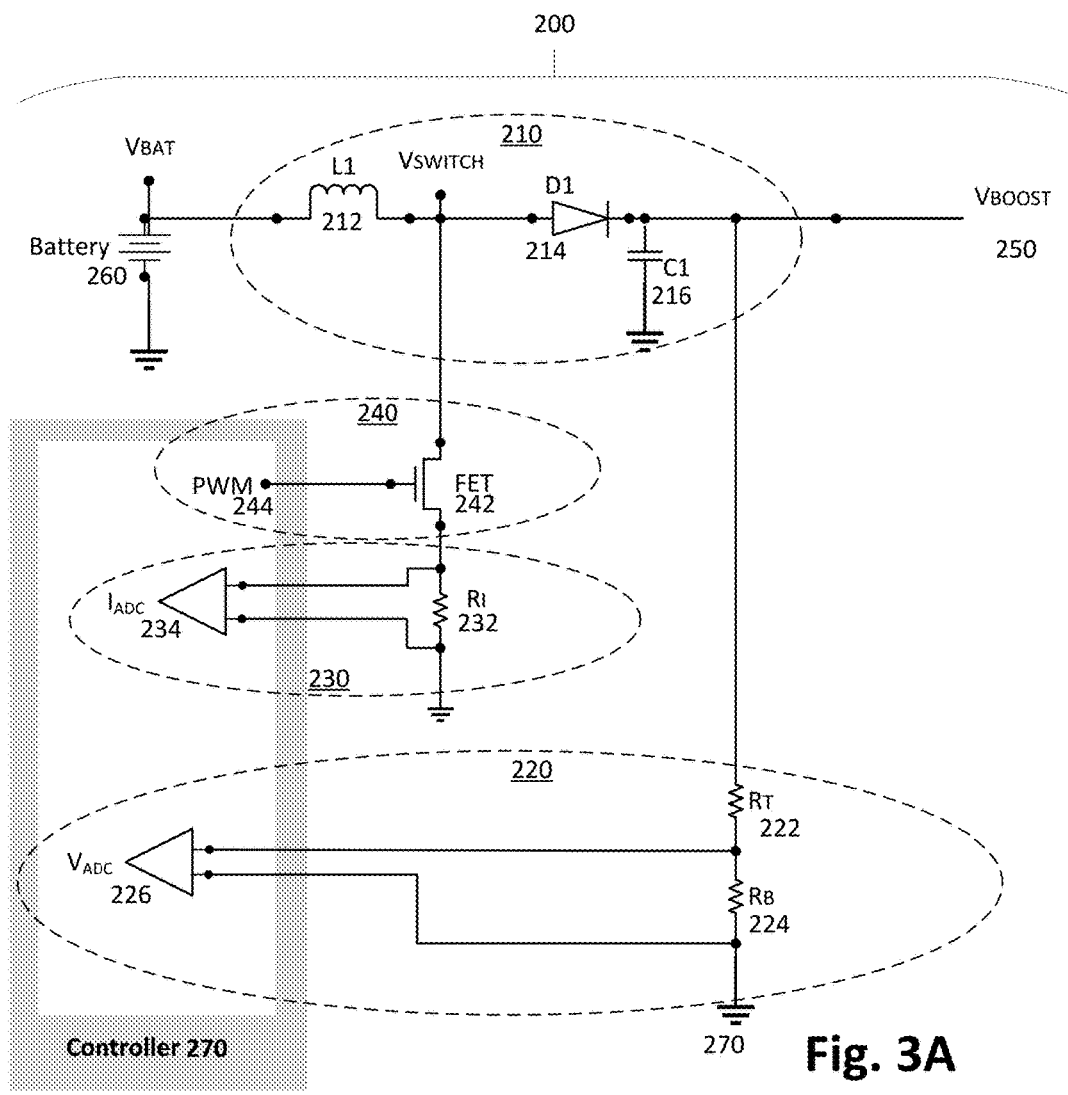
FIG. 3A is a circuit diagram of an example of a boosted voltage circuit that provides feedback.
FIG. 3B is a circuit diagram of an example of a charge application circuit that uses an output of the boosted voltage circuit.

To meet the above needs, examples implement a novel boosted voltage circuit that includes a feedback circuit and a charge application circuit. FIG. 3A is a circuit diagram of an example of the boosted voltage circuit 200 that provides feedback. FIG. 3B is a circuit diagram of an example of a charge application circuit 300 that uses an output of boosted voltage circuit 200. Boosted voltage circuit 200 includes both electrical components and a controller/processor 270 that includes a sequence of instructions that together modify the voltage level of activation/stimulation delivered to the external dermis of user 105 by patch 100 through electrodes. Controller/processor 270 in examples is implemented by control unit 1002 of FIG. 2.

Boosted voltage circuit 200 can replace an independent analog-controlled boost regulator by using a digital control loop to create a regulated voltage, output voltage 250, from the battery source. Output voltage 250 is provided as an input voltage to charge application circuit 300. In examples, this voltage provides nerve stimulation currents through the dermis/skin to deliver therapy for an overactive bladder. Output voltage 250, or "$VB_{oost}$", at voltage output node 250, uses two digital feedback paths 220, 230, through controller 270. In each of these paths, controller 270 uses sequences of instructions to interpret the measured voltages at voltage monitor 226, or "VADC" and current monitor 234, or "IADc", and determines the proper output control for accurate and stable output voltage 250.

Boosted voltage circuit 200 includes an inductor 212, a diode 214, and a capacitor 216 that together implement a boosted converter circuit 210. A voltage monitoring circuit 220 includes a resistor divider formed by a top resistor 222, or "$R_T$", a bottom resistor 224, or "RB" and voltage monitor 226. A current monitoring circuit 230 includes a current measuring resistor 232, or "$R_I$" and current monitor 234. A pulse width modulation ("PWM") circuit 240 includes a field-effect transistor ("FET") switch 242, and a PWM driver 244. Output voltage 250 functions as a sink for the electrical energy. An input voltage 260, or "VBAT", is the source for the electrical energy, and can be implemented by power 1012 of FIG. 2.

PWM circuit 240 alters the "on" time within a digital square wave, fixed frequency signal to change the ratio of time that a power switch is commanded to be "on" versus "off." In boosted voltage circuit 200, PWM driver 244 drives FET switch 242 to "on" and "off" states.

In operation, when FET switch 242 is on, i.e., conducting, the drain of FET switch 242 is brought down to Ground/GND or ground node 270. FET switch 242 remains on until its current reaches a level selected by controller 270 acting as a servo controller. This current is measured as a representative voltage on current measuring resistor 232 detected by current monitor 234. Due to the inductance of inductor 212, energy is stored in the magnetic field within inductor 212. The current flows through current measuring resistor 232 to ground until FET switch 242 is opened by PWM driver 244.

When the intended pulse width duration is achieved, controller 270 turns off FET switch 242. The current in inductor 212 reroutes from FET switch 242 to diode 214, causing diode 214 to forward current. Diode 214 charges capacitor 216. Therefore, the voltage level at capacitor 216 is controlled by controller 270.

Output voltage 250 is controlled using an outer servo loop of voltage monitor 226 and controller 270. Output voltage 250 is measured by the resistor divider using top resistor 222, bottom resistor 224, and voltage monitor 226. The values of top resistor 222 and bottom resistor 224 are selected to keep the voltage across bottom resistor 224 within the monitoring range of voltage monitor 226. Controller 270 monitors the output value from voltage monitor 226.

Charge application circuit 300 includes a pulse application circuit 310 that includes an enable switch 314. Controller 270 does not allow enable switch 314 to turn on unless output voltage 250 is within a desired upper and lower range of the desired value of output voltage 250. Pulse application circuit 310 is operated by controller 270 by asserting an enable signal/voltage 312, or "VSW", which turns on enable switch 314 to pass the electrical energy represented by output voltage 250 through electrodes 320 via a capacitor 316. Capacitor 316 isolates electrodes 320 from DC voltages in the charging circuit, as a safety feature in the device. At the same time, controller 270 continues to monitor output voltage 250 and controls PWM driver 244 to switch FET switch 242 on and off and to maintain capacitor 216 to the desired value of output voltage 250.

The stability of output voltage 250 can be increased by an optional inner feedback loop through FET Switch 242, current measuring resistor 232, and current monitor 234. Controller 270 monitors the output value from current monitor 234 at a faster rate than the monitoring on voltage monitor 226 so that the variations in the voltages achieved at the cathode of diode 214 are minimized, thereby improving control of the voltage swing and load sensitivity of output voltage 250.

As described, in examples, controller 270 uses multiple feedback loops to adjust the duty cycle of PWM driver 244 to create a stable output voltage 250 across a range of values. Controller 270 uses multiple feedback loops and monitoring circuit parameters to control output voltage 250 and to evaluate a proper function of the hardware. Controller 270 acts on the feedback and monitoring values in order to provide improved patient safety and reduced electrical hazard by disabling incorrect electrical functions.

In some examples, controller 270 implements the monitoring instructions in firmware or software code. In some examples, controller 270 implements the monitoring instructions in a hardware state machine.

In some examples, voltage monitor 226 is an internal feature of controller 270. In some examples, voltage monitor 226 is an external component, which delivers its digital output value to a digital input port of controller 270.

In some examples, current monitor 234 is an internal feature of controller 270. In some examples, current monitor 234 is an external component, which delivers its digital output value to a digital input port of controller 270.

An advantage of boosted voltage circuit 200 over known circuits is decreased component count which may result in reduced costs, reduced circuit board size and higher reliability. Further, boosted voltage circuit 200 provides for centralized processing of all feedback data which leads to faster response to malfunctions. Further, boosted voltage circuit 200 controls outflow current from VBAT 260, which increases the battery's lifetime and reliability.

Figure 4:
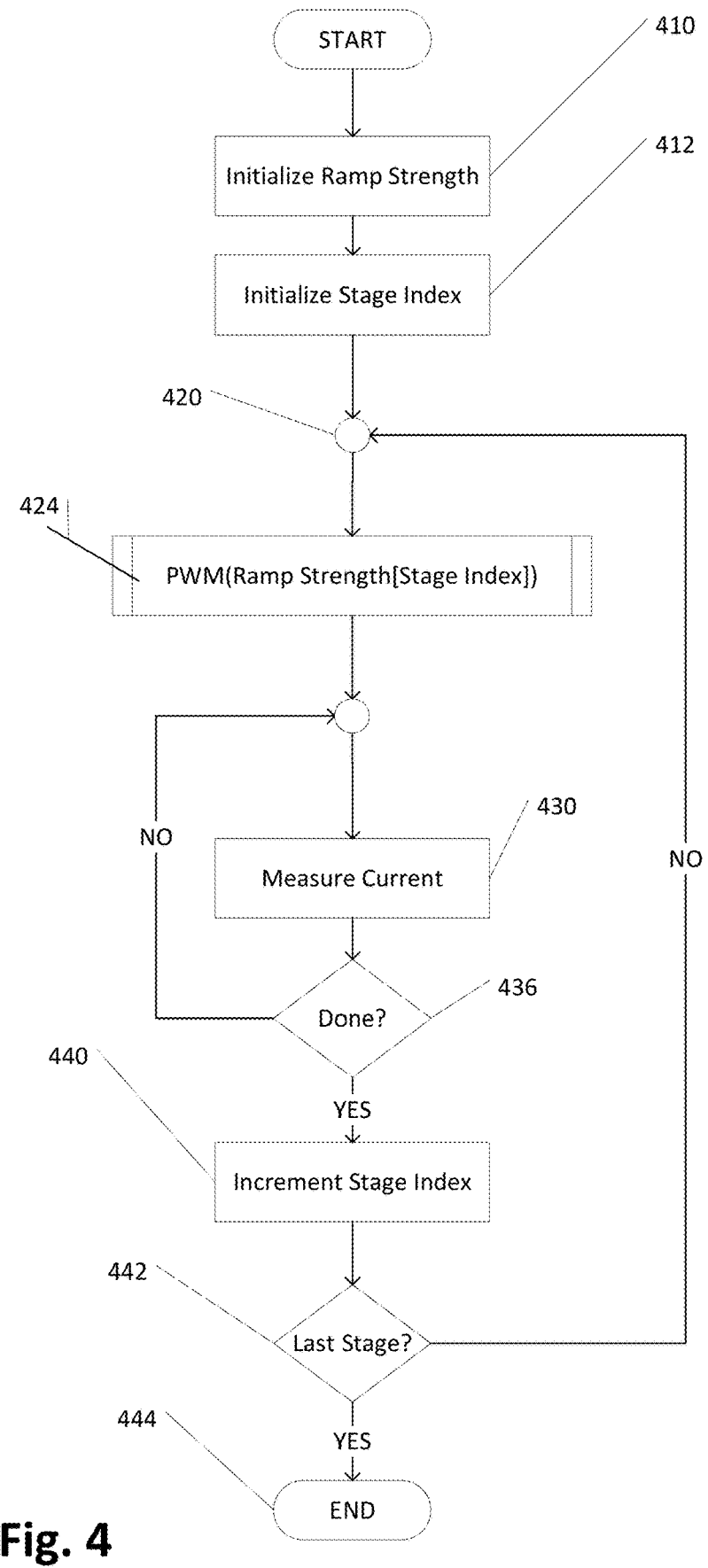
FIG. 4 is a flow diagram of the functionality of the controller of monitoring and controlling the output voltage, including its ramp rate.

FIG. 4 is a flow diagram of the functionality of controller 270 of monitoring and controlling output voltage 250, including its ramp rate. In one example, the functionality of the flow diagram of FIG. 4, and FIGS. 5, 11 and 12 below, is implemented by software stored in memory or other computer readable or tangible medium, and executed by a processor. In other examples, the functionality may be performed by hardware (e.g., through the use of an application-specific integrated circuit ("ASIC"), a programmable gate array ("PGA"), a field programmable gate array ("FPGA"), etc.), or any combination of hardware and software.

The pulse width modulation of FET switch 242 is controlled by one or more pulses for which the setting of each pulse width allows more or less charge to accumulate as a voltage at capacitor 216 through diode 214. This pulse width setting is referred to as the ramp strength and it is initialized at 410. Controller 270 enables each pulse group in sequence with a pre-determined pulse width, one stage at a time, using a stage index that is initialized at 412. The desired ramp strength is converted to a pulse width at 424, which enables and disables FET switch 242 according to the pulse width. During the intervals when FET switch 242 is "on", the current is measured by current monitor 234 at 430 and checked against the expected value at 436. When the current reaches the expected value, the stage is complete and the stage index is incremented at 440. If the desired number of stages have been applied 442, then the functionality is complete. Otherwise, the functionality continues to the next stage at 420.

As a result of the functionality of FIG. 4, VBAT 260 used in patch 100 operates for longer periods as the current drawn from the battery ramps at a low rate of increase to reduce the peak current needed to achieve the final voltage level 250 for each activation/stimulation treatment. The PWM 244 duty cycle is adjusted by controller 270 to change the ramp strength at 410 to improve the useful life of the battery.

An open loop protocol to control current to electrodes in known neural stimulation devices does not have feedback controls. It commands a voltage to be set, but does not determine the amount of actual current delivered to the user. A stimulation pulse is sent based on preset parameters and generally cannot be modified based on feedback from the patient's anatomy. When the device is removed and repositioned, the electrode placement varies. Also the humidity and temperature of the anatomy changes throughout the day. All these factors affect the actual charge delivery if the voltage is preset. Charge control is a patient safety feature and facilitates an improvement in patient comfort, treatment consistency and efficacy of treatment.

In contrast, examples of patch 100 includes features that address these shortcomings using controller 270 to regulate the charge applied by electrodes 320. Controller 270 samples the voltage of the stimulation waveform, providing feedback and impedance calculations for an adaptive protocol to modify the stimulation waveform in real time. The current delivered to the anatomy by the stimulation waveform is integrated using a differential integrator and sampled and then summed to determine the actual charge delivered to the user for a treatment, such as OAB treatment. After every pulse in a stimulation event, this data is analyzed and used to modify, in real time, subsequent pulses.

This hardware adaptation allows a firmware protocol to implement the adaptive protocol. This protocol regulates the charge applied to the body by changing output voltage ("$V_{BOOST}$") 250. A treatment is performed by a sequence of periodic pulses, which deliver charge into the body through electrodes 320. Some of the parameters of the treatment are fixed and some are user adjustable. The strength, duration and frequency may be user adjustable. The user may adjust these parameters as necessary for comfort and efficacy. The strength may be lowered if there is discomfort and raised if nothing is felt. The duration can be increased if the maximum acceptable strength results in an ineffective treatment.

Adaptive Protocol

Figure 5:
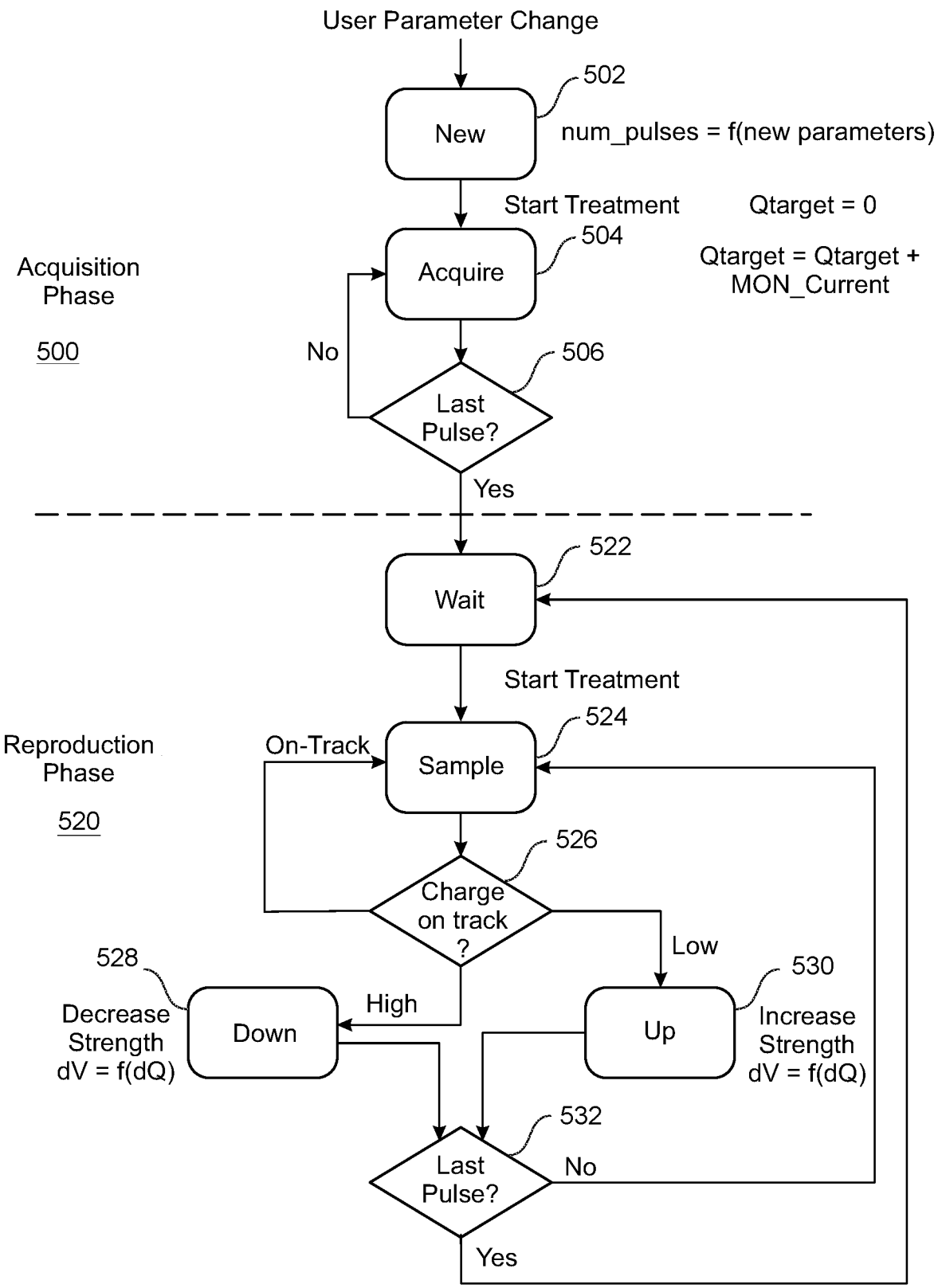
FIG. 5 is a flow diagram in accordance with one example of an adaptive protocol.

A flow diagram in accordance with one example of the adaptive protocol discussed above is shown in FIG. 5. The adaptive protocol strives to repeatedly and reliably deliver a target charge ("$Q_{target}$") in coulombs during a treatment and to account for any environmental changes. Therefore, the functionality of FIG. 5 is to adjust the charge level applied to a user based on feedback, rather than use a constant level.

The mathematical expression of this protocol is as follows:

$Q_{target} = Q_{target}(A*dS+B*dT)$, where $A$ is the Strength Coefficient–determined empirically, $dS$ is the user change in Strength, $B$ is the Duration Coefficient–determined empirically, and $dT$ is the user change in Duration.

Figure 6:
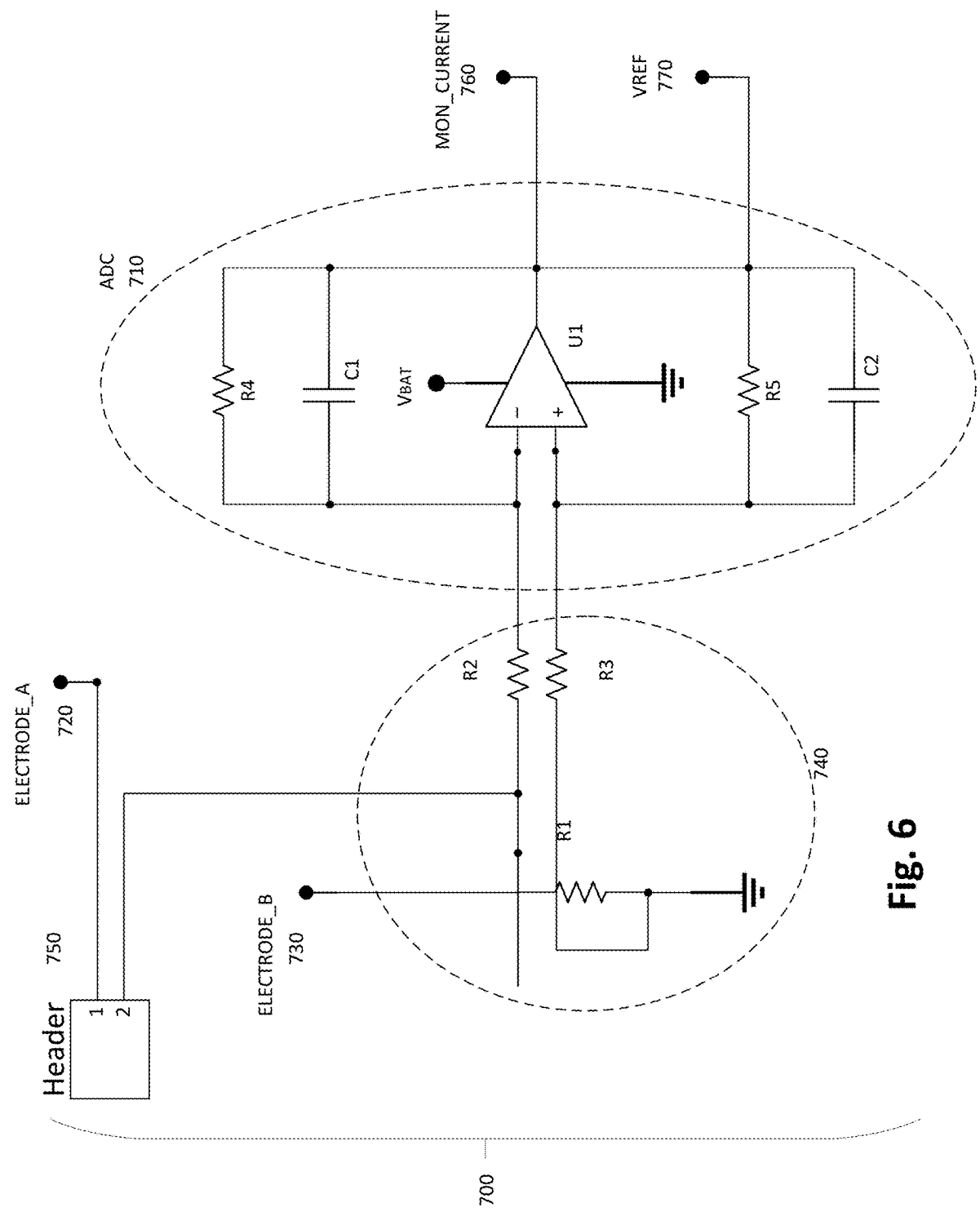
FIG. 6 is a Differential Integrator Circuit used in the adaptive protocol in accordance with one example.

The adaptive protocol includes two phases in one example: Acquisition phase 500 and Reproduction phase 520. Any change in user parameters places the adaptive protocol in the Acquisition phase. When the first treatment is started, a new baseline charge is computed based on the new parameters. At a new acquisition phase at 502, all data from the previous charge application is discarded. In one example, 502 indicates the first time for the current usage where the user places patch 100 on a portion of the body and manually adjusts the charge level, which is a series of charge pulses, until it feels suitable, or any time the charge level is changed, either manually or automatically. The treatment then starts. The mathematical expression of this function of the application of a charge is as follows:

The charge delivered in a treatment is $$Q_{target} = \sum_{i=1}^{T*f} Q_{pulse}(i)$$

Where T is the duration; f is the count of pulses for one treatment (e.g., Hertz or cycles/second) of "Rep Rate"; $Q_{pulse}$ (i) is the measured charge delivered by Pulse (i) in the treatment pulse train provided as a voltage MON_CURRENT that is the result of a Differential Integrator circuit shown in FIG. 6 (i.e., the average amount of charge per pulse). Differential Integrator circuit 700 of FIG. 6 is an example of a circuit used to integrate current measured over time and quantify the delivered charge and therefore determine the charge output over a treatment pulse. The number of pulses in the treatment is T*f.

As shown in of FIG. 6, MON_CURRENT 760 is the result of the Differential Integrator Circuit 700. The Analog to Digital Conversion ("ADC") 710 feature is used to quantify voltage into a number representing the delivered charge. The voltage is measured between Electrode A 720 and Electrode B 730, using a Kelvin Connection 740. Electrode A 720 and Electrode B 730 are connected to a header 750. A reference voltage, VREF 770, is included to keep the measurement in range.

In some examples, Analog to Digital Conversion 710 is an internal feature of controller 270. In some examples, Analog to Digital Conversion 710 is an external component, which delivers its digital output value to a digital input port on Controller 270.

At 504 and 506, every pulse is sampled. In one example, the functionality of 504 and 506 lasts for 10 seconds with a pulse rate of 20 Hz, which can be considered a full treatment cycle. The result of Acquisition phase 500 is the target pulse charge of $Q_{target}$.

FIG. 7 is a table in accordance with one example showing the number of pulses per treatment measured against two parameters, frequency and duration. Frequency is shown on the Y-axis and duration on the X-axis. The adaptive protocol in general performs better when using more pulses. One example uses a minimum of 100 pulses to provide for solid convergence of charge data feedback, although a less number of pulses can be used in other examples. Referring to the FIG. 7, a frequency setting of 20 Hz and duration of 10 seconds produces 200 pulses.

The reproduction phase 520 begins in one example when the user initiates another subsequent treatment after acquisition phase 500 and the resulting acquisition of the baseline charge, $Q_{target}$. For example, a full treatment cycle, as discussed above, may take 10 seconds. After, for example, a two-hour pause as shown at wait period 522, the user may then initiate another treatment. During this phase, the adaptive protocol attempts to deliver $Q_{target}$ for each subsequent treatment. The functionality of reproduction phase 520 is needed because, during the wait period 522, conditions such as the impedance of the user's body due to sweat or air humidity may have changed. The differential integrator is sampled at the end of each Pulse in the Treatment. At that point, the next treatment is started and the differential integrator is sampled for each pulse at 524 for purposes of comparison to the acquisition phase $Q_{target}$. Sampling the pulse includes measuring the output of the pulse in terms of total electric charge. The output of the integrator of FIG. 6 in voltage, referred to as Mon_Current 760, is a direct linear relationship to the delivered charge and provides a reading of how much charge is leaving the device and entering the user. At 526, each single pulse is compared to the charge value determined in Acquisition phase 500 (i.e., the target charge) and the next pulse will be adjusted in the direction of the difference.

NUM_PULSES=(T*f)

After each pulse, the observed charge, $Q_{pulse}(i)$, is compared to the expected charge per pulse.

$Q_{pulse}(i) > Q_{target}$/NUM_PULSES?

The output charge or "$V_{BOOST}$" is then modified at either 528 (decreasing) or 530 (increasing) for the subsequent pulse by:

$dV(i) = G[Q_{target}/\text{NUM\_PULSES} - Q_{pulse}(i)]$ where G is the Voltage adjustment Coefficient–determined empirically. The process continues until the last pulse at 532.

A safety feature assures that the $V_{BOOST}$ will never be adjusted higher by more than 10%. If more charge is necessary, then the repetition rate or duration can be increased.

In one example a boosted voltage circuit uses dedicated circuits to servo the boosted voltage. These circuits process voltage and/or current measurements to control the PWM duty cycle of the boosted voltage circuit's switch. The system controller can set the voltage by adjusting the gain of the feedback loop in the boosted voltage circuit. This is done with a digital potentiometer or other digital to analog circuit.

In one example, in general, the current is sampled for every pulse during acquisition phase 500 to establish target charge for reproduction. The voltage is then adjusted via a digital potentiometer, herein referred to as "Pot", during reproduction phase 520 to achieve the established target_charge.

The digital Pot is calibrated with the actual voltage at startup. A table is generated with sampled voltage for each wiper value. Tables are also precomputed storing the Pot wiper increment needed for 1 v and 5 v output delta at each pot level. This enables quick reference for voltage adjustments during the reproduction phase. The tables may need periodic recalibration due to battery level.

In one example, during acquisition phase 500, the data set=100 pulses and every pulse is sampled and the average is used as the target_charge for reproduction phase 520. In general, fewer pulses provide a weaker data sample to use as a basis for reproduction phase 520.

In one example, during acquisition phase 500, the maximum data set=1000 pulses. The maximum is used to avoid overflow of 32 bit integers in accumulating the sum of samples. Further, 1000 pulses in one example is a sufficiently large data set and collecting more is likely unnecessary.

After 1000 pulses for the above example, the target_charge is computed. Additional pulses beyond 1000 in the acquisition phase do not contribute to the computation of the target charge. In other examples, the maximum data set is greater than 1000 pulses when longer treatment cycle times are desired.

In one example, the first 3-4 pulses are generally higher than the rest so these are not used in acquisition phase 500. This is also accounted for in reproduction phase 520. Using these too high values can result in target charge being set too high and over stimulating on the subsequent treatments in reproduction phase 520. In other examples, more advanced averaging algorithms could be applied to eliminate high and low values.

In an example, there may be a safety concern about automatically increasing the voltage. For example, if there is poor connection between the device and the user's skin, the voltage may auto-adjust at 530 up to the max. The impedance may then be reduced, for example by the user pressing the device firmly, which may result in a sudden high current. Therefore, in one example, if the sample is 500 mv or more higher than the target, it immediately adjusts to the minimum voltage. This example then remains in reproduction phase 520 and should adjust back to the target current/charge level. In another example, the maximum voltage increase is set for a single treatment (e.g., 10V). More than that is not needed to achieve the established target_charge. In another example, a max is set for $V_{BOOST}$ (e.g., 80V).

In various examples, it is desired to have stability during reproduction phase 520. In one example, this is accomplished by adjusting the voltage by steps. However, a relatively large step adjustment can result in oscillation or over stimulation. Therefore, voltage adjustments may be made in smaller steps. The step size may be based on both the delta between the target and sample current as well as on the actual $V_{BOOST}$ voltage level. This facilitates a quick and stable/smooth convergence to the target charge and uses a more gradual adjustments at lower voltages for more sensitive users.

The following are the conditions that may be evaluated to determine the adjustment step.

delta-mon_current=abs(sample_mon_current−target_charge)

If delta_mon_current>500 mv and $V_{BOOST}$>20V then step=5V for increase adjustments (For decrease adjustments a 500 mv delta triggers emergency decrease to minimum Voltage)

If delta_mon_current>200 mv then step=1V

If delta_mon_current>100 mv and delta_mon_current>5%*sample_mon_current then step=1V In other examples, new treatments are started with voltage lower than target voltage with a voltage buffer of approximately 10%. The impedance is unknown at the treatment start. These examples save the target_voltage in use at the end of a treatment. If the user has not adjusted the strength parameter manually, it starts a new treatment with saved target_voltage with the 10% buffer. This achieves target current quickly with the 10% buffer to avoid possible over stimulation in case impedance has been reduced. This also compensates for the first 3-4 pulses that are generally higher.

As disclosed, examples apply an initial charge level, and then automatically adjust based on feedback of the amount of current being applied. The charge amount can be varied up or down while being applied. Therefore, rather than setting and then applying a fixed voltage level throughout a treatment cycle, implementations of the invention measure the amount of charge that is being input to the user, and adjust accordingly throughout the treatment to maintain a target charge level that is suitable for the current environment.

The Adaptive Circuit described above provides the means to monitor the charge sent through the electrodes to the user's tissue and to adjust the strength and duration of sending charge so as to adapt to changes in the impedance through the electrode-to-skin interface and through the user's tissue such that the field strength at the target nerve is within the bounds needed to overcome the action potential of that nerve at that location and activate a nerve impulse. These changes in impedance may be caused by environmental changes, such as wetness or dryness of the skin or underlying tissue, or by applied lotion or the like; or by tissue changes, such as skin dryness; or by changes in the device's placement on the user's skin, such as by removing the patch and re-applying it in a different location or orientation relative to the target nerve; or by combinations of the above and other factors.

The combined circuits and circuit controls disclosed herein generate a charge that is repeated on subsequent uses. The voltage boost conserves battery power by generating voltage on demand. The result is an effective and compact electronics package suitable for mounting on or in a fabric or similar material for adherence to a dermis that allows electrodes to be placed near selected nerves to be activated.

In one example, a voltage doubler circuit, using two diode stages, is added to boosted voltage circuit 200 of FIG. 2 to double the high voltage output or to reduce voltage stress on FET 242. The voltage doubler circuit builds charge in a transfer capacitor when FET 242 is turned on and adds voltage to the output of boosted voltage circuit 200 when FET 242 is turned off. The diodes only conduct in the positive phase so that the voltage is doubled.

Figure 8:
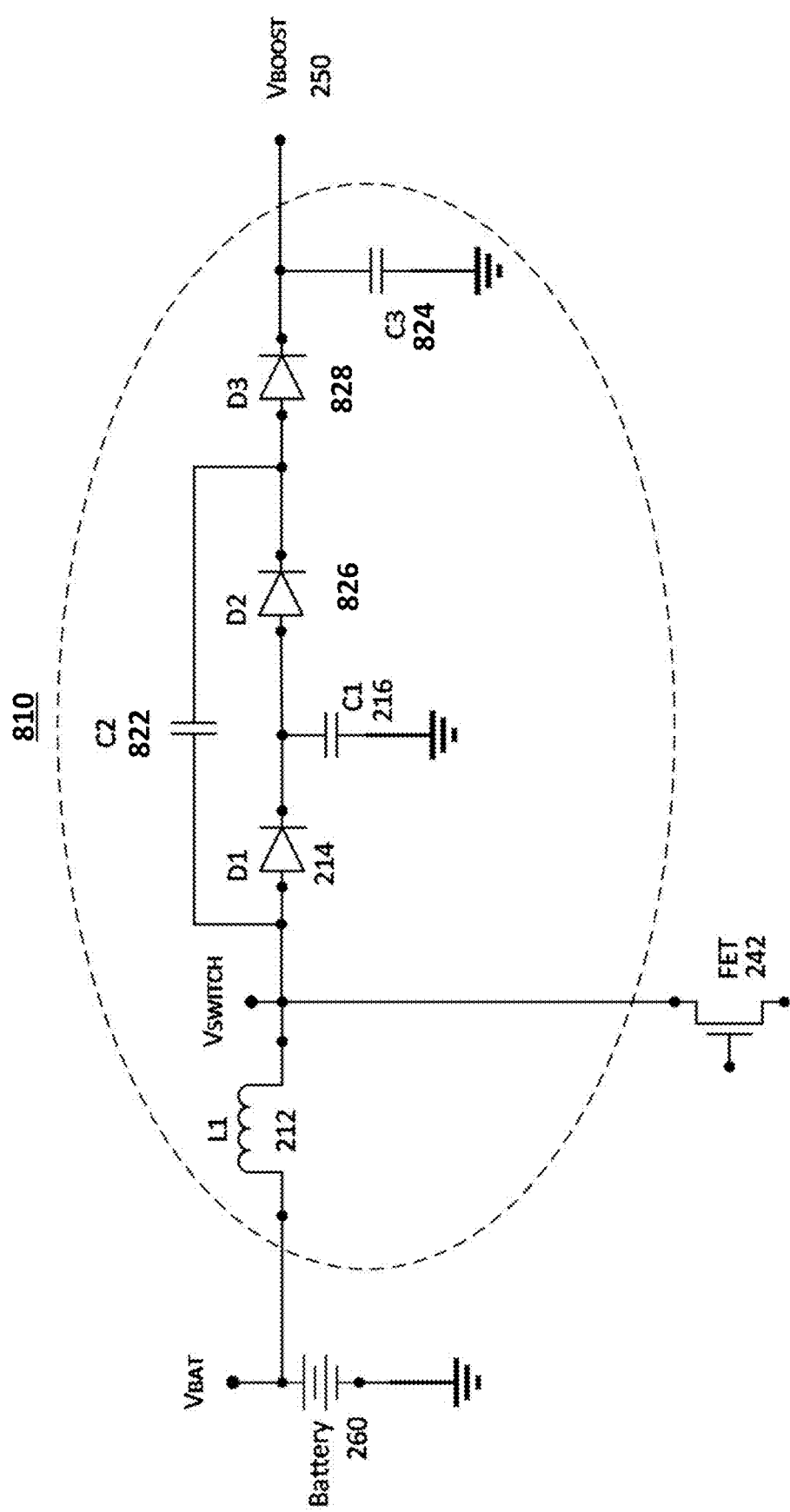
FIG. 8 illustrates a boosted converter circuit that can be used instead of the boosted converter circuit in boosted voltage circuit of FIG. 2 in example inventions.

FIG. 8 illustrates a boosted converter circuit 810 that can be used instead of boosted converter circuit 210 in boosted voltage circuit 200 of FIG. 2 in example inventions. Boosted converter circuit 810 includes three diode stages with the addition of diodes 826, 828 and capacitors 822, 824.

Oscillator Timing

In example inventions, controller 270 includes a real time clock ("RTC") circuit which is used to measure time intervals, including time between activation pulses, and the width of the activation pulses. The RTC circuit runs continuously on controller 270 to continuously track in real time. However, this continuous operation continuously draws power from the battery.

In other example inventions, the RTC circuit is not used and is set to inoperative mode by firmware in controller 270. The firmware sets timers using the on-chip oscillator, which has a known frequency and can therefore measure a time interval. The firmware clears a counter when patch 100 is connected to the fob or smart controller. The zeroed out time becomes the initial time for subsequent activation events. The firmware adjusts the value of the counter each time the time on the timer elapses, as measured by the on-chip oscillator. The firmware may report counter values to the fob or the smart controller, or both. The fob and the smart controller use the real time clock in their own controllers to calculate a real time value for the activation time by adding a value proportional to the counter value and to the activation period to the real time clock value. This allows the firmware to avoid the use of the on-chip real time clock, which saves power consumption and extends the battery life in patch 100 and further allows the fob or the smart controller to calculate real time markers for activations of patch 100. The markers are useful for analysis of the operation of patch 100. The on-chip oscillator runs continuously, but consumes significantly less power than the on-chip real time clock. In example inventions, controller 270 includes a 32.768 kHz+/−250 ppm RC oscillator. A one second interval is generated when dividing by $2^{15}$.

Current Measure for Charge Delivery

As disclosed above, in example inventions, the charge delivered to the user by patch 100 is determined using differential integrator circuit 700 of FIG. 6.

Figure 9:
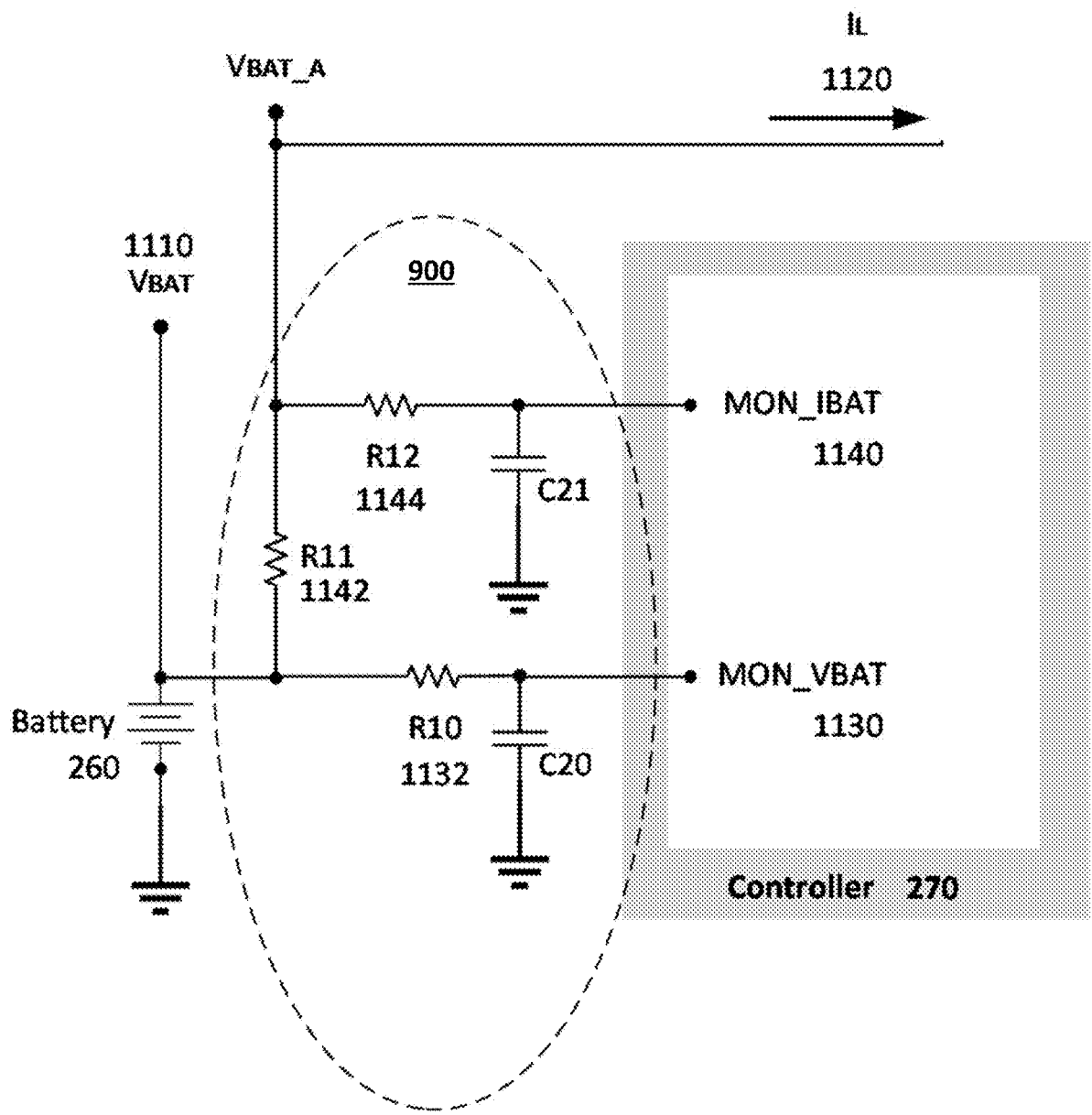
FIG. 9 illustrates a charge monitoring circuit that is used to determine the charge delivered to the user by the patch in other example inventions.

FIG. 9 illustrates a charge monitoring circuit 900 that is used to determine the charge delivered to the user by patch 100 in other example inventions. Circuit 900 measures battery current to the high voltage boost circuit. Charge monitoring circuit 900 includes a current measure resistor 1142 used to provide a measure to controller 270 of the current over time going into the load as load current 1120. The amount of charge required to recharge the boost regulator (shown in FIG. 8 for producing high voltage for the electrodes), is used as a measurement of how much charge is passed to the user at electrodes 320. Controller 270 acquires as input a measured voltage, MON_IBAT 1140, that is proportional to the current input to the boost regulator, and repeats this acquisition for each application pulse. Controller 270 sums the charge calculated from each MON_IBAT 1140 measurement to determine the total charge passing through current measure resistor 1142. In a similar manner, controller 270 measures the voltage at the battery 260 as VBAT 1110. Controller 270 uses a MON_VBAT 1130 value to check that battery 260 continues to output a sufficient voltage. Resistors 1132, 1144 reduce noise in the measurements.

In comparison to differential integrator circuit 700 of FIG. 6, current monitoring circuit 900 uses fewer components, requires no precision components, and uses less space on the respective printed circuit board ("PCB") (e.g., a rigid substrate, such as FR-4, or a flexible substrate, such as polyimide).

Monitoring $V_{BOOST}$

The impedance of the connection from patch 100 to the user from one electrode, and then through the tissues of the user and back to the opposite electrode on patch 100 may vary, such as from environmental humidity or dryness of the skin. As the impedance varies, the voltage needed at $V_{BOOST}$ will vary to deliver the charge value, selected by the user or set by default, to stimulate the target nerve. In an open loop design, applying the same $V_{BOOST}$ for each stimulation may result in lower or higher amount of charge delivered to the user, which can affect the efficacy of the stimulation. It may also affect the comfort of the user as the skin will sense the stimulation pulse differently according to changes in impedance.

Figure 10:
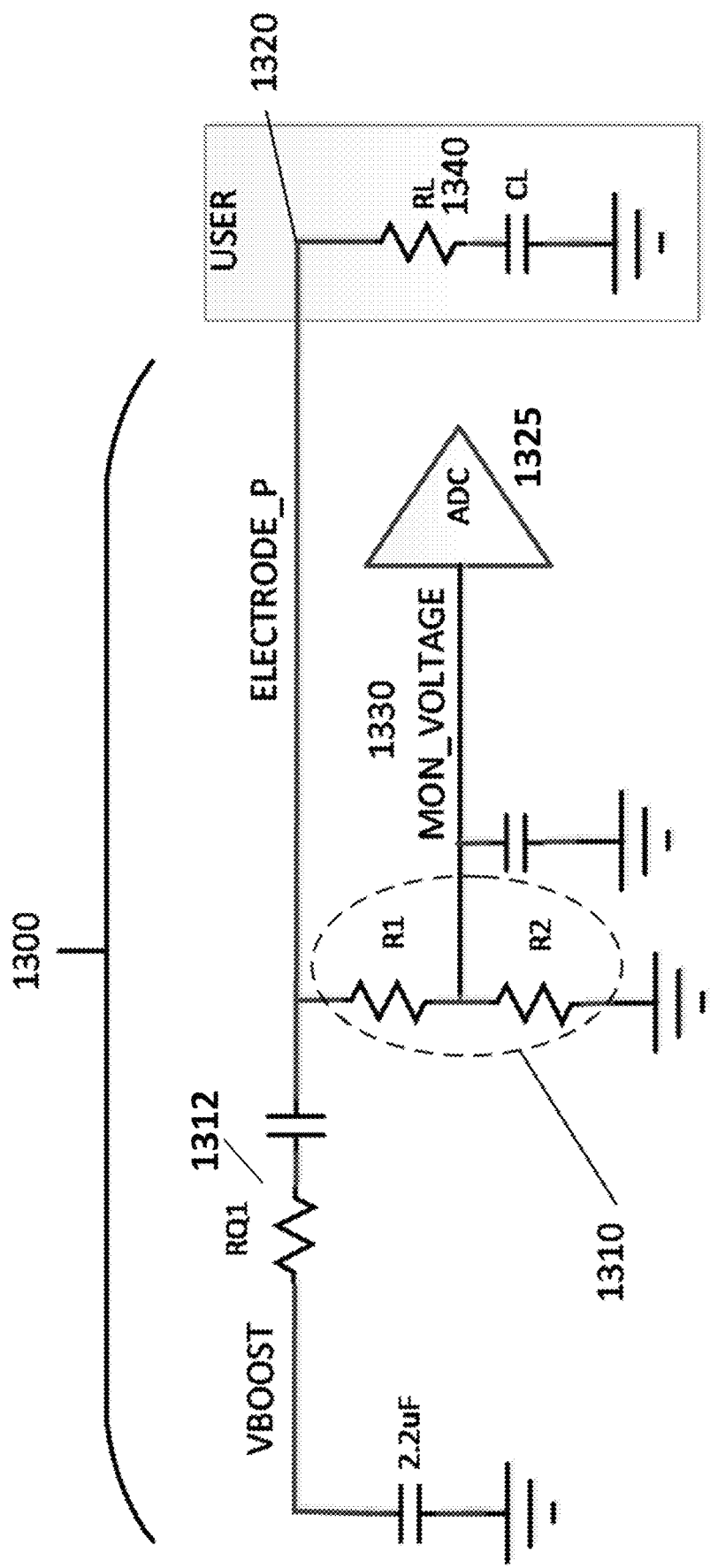
FIG. 10 illustrates a closed loop circuit used in example inventions to measure the charge applied to the user.

In contrast, FIG. 10 illustrates a closed loop circuit 1300 used in example inventions to measure the charge applied to the user via a measurement of the electrode voltage. In closed loop circuit 1300, $V_{BOOST}$ is sampled and the delivered charge is calculated for each stimulation pulse delivered to the user.

Circuit 1300 includes a voltage divider 1310 that includes two resistors R1 and R2, to scale a treatment pulse voltage 1320 to a lower range MON_VOLTAGE 1330, for sampling by an ADC 1325. By repeating the sampling of the voltage at MON_VOLTAGE 1330 many times during the duration of one applied stimulation pulse, the voltage waveform of the pulse can be acquired (i.e., an amount of voltage applied to the user for a single pulse, which exponentially decays during the pulse).

Voltage divider 1310 is in parallel with the user anatomy, represented in this simple resistive model as RL 1340. The Human Body Model for capacitance, as defined by the Electrostatic Discharge Association ("ESDA") is a 100 picofarad capacitor in series with a 1500 Ohm resistor. Measuring the pulse voltage at MON_VOLTAGE 1330, and integrating over the duration of the pulse, then dividing by the resistance of RL 1340 results in a calculation of the integral of the current, which is the total charge. RQ1 is the "on resistance" of a switch transistor 1312 and should be 14 Ohms or less. Switch transistor 1312 will switch the High Voltage $V_{BOOST}$ to the electrode for a short interval, and is shown in FIG. 10 as RQ1 and modelling its "on resistance". When a pulse is not being applied, it is an open.

The firmware of patch 100 firmware tests the values of MON_VOLTAGE 1330 as they are read through ADC 1325 as a firmware loop at the sampling frequency of MON_VOLTAGE 1330. The applied voltage is calculated in each iteration from the MON_VOLTAGE value. When the applied voltage reaches the level selected by the user or the default value, the switch transistor (i.e., switch transistor 242 of FIG. 8) opens to stop application of more charge to the user because the PWM stops when $V_{BOOST}$ reaches its target. As disclosed, FIG. 10 is an alternative to FIG. 6, and each measure electrode current and then determines an amount of charge delivered to a user. FIG. 9 measures the battery current.

Adaptive Waveform for Fine Intensity Control

The oscillator clock frequency in example inventions is chosen to optimize power consumption of the clocked circuits while also providing enough speed for microcontroller operation and other timing circuits that are disclosed above.

PWM circuit 244 modifies the pulse width by varying the count of oscillator clock periods. Due to the limited clock frequency, it can be difficult to have enough resolution in the PWM duty cycle to create enough different strength levels in the stimulation. This may lead to users being unable to select between one level that is too weak and the next higher level that is too strong.

Therefore, in example inventions, control of the boosted voltage ($V_{BOOST}$) is enhanced to provide higher discernment between levels by foregoing level selection within the PWM duty cycle and instead initiating the stimulation at the moment the boosted voltage ramps to the desired voltage, as read by the microcontroller ADC. This achieves many more strength levels with smaller gaps between the levels than those, which are limited by the resolution of the PWM due to the much higher ADC measurement frequency. The ADC feedback to the microcontroller is used to curtail the PWM active time as soon as the desired voltage threshold is reached.

In addition to providing more levels of intensity adjustment, battery power is saved by stopping the boosted voltage output until the next pulse is needed. Some battery types have poor performance when the rate of change of the current demanded from the battery exceeds a certain maximum specification. A circuit, which begins to demand current from the battery and increases that demanded current level at a slower rate, allows the battery to perform better over multiple such cycles of demanded power.

In one example, the PWM duty cycle is varied from the first pulse to the last in the series of pulses for a stimulation, to use lower duty cycle pulses at the beginning of stimulation and higher duty cycle pulses later in the stimulation. The narrower pulses formed from the lower duty cycle reduce the demand for charge on the battery circuit, such that the current demand starts out more slowly than in a circuit without duty cycle adaptation, and continues through the stimulation pulse sequence to provide wider pulses with higher current demand, in order to stay within the current specification of the battery while also rising to meet the stimulation energy required by the user when they adjusted the intensity.

Qualifying Applied Stimulation Pulses

The energy provided by the battery for each stimulation pulse is dependent on the type of battery in patch 100. The performance of the battery changes during the course of applying the sequence of pulses. The battery performance may be affected by temperature, humidity, age of the battery, and other factors. Due to this variation in battery performance, in example inventions the treatment is adjusted most or every time the treatment is applied to a user.

Figure 11:
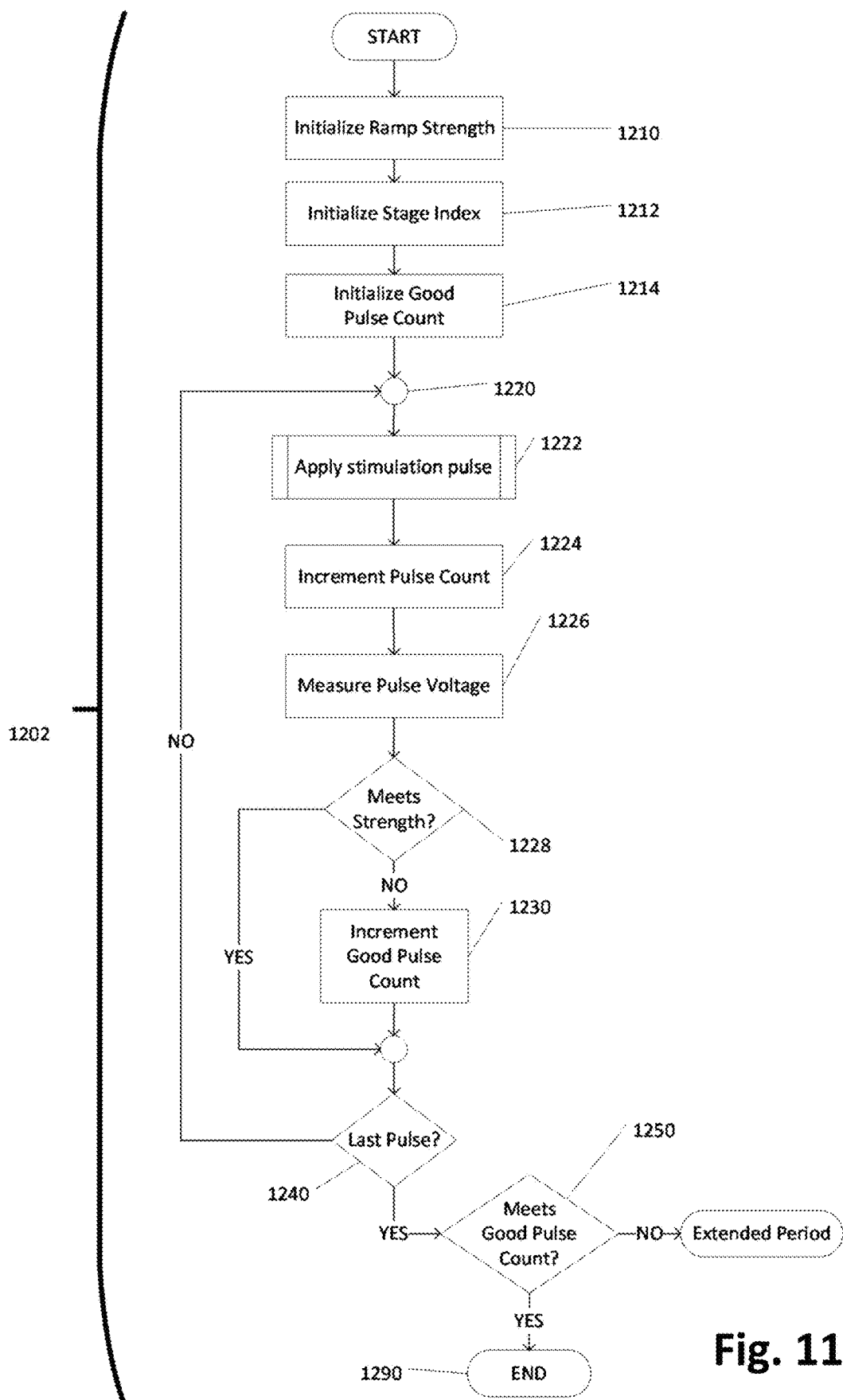
FIGS. 11 and 12 are flow diagrams of treatment monitoring functionality in accordance to example inventions.
Figure 12:
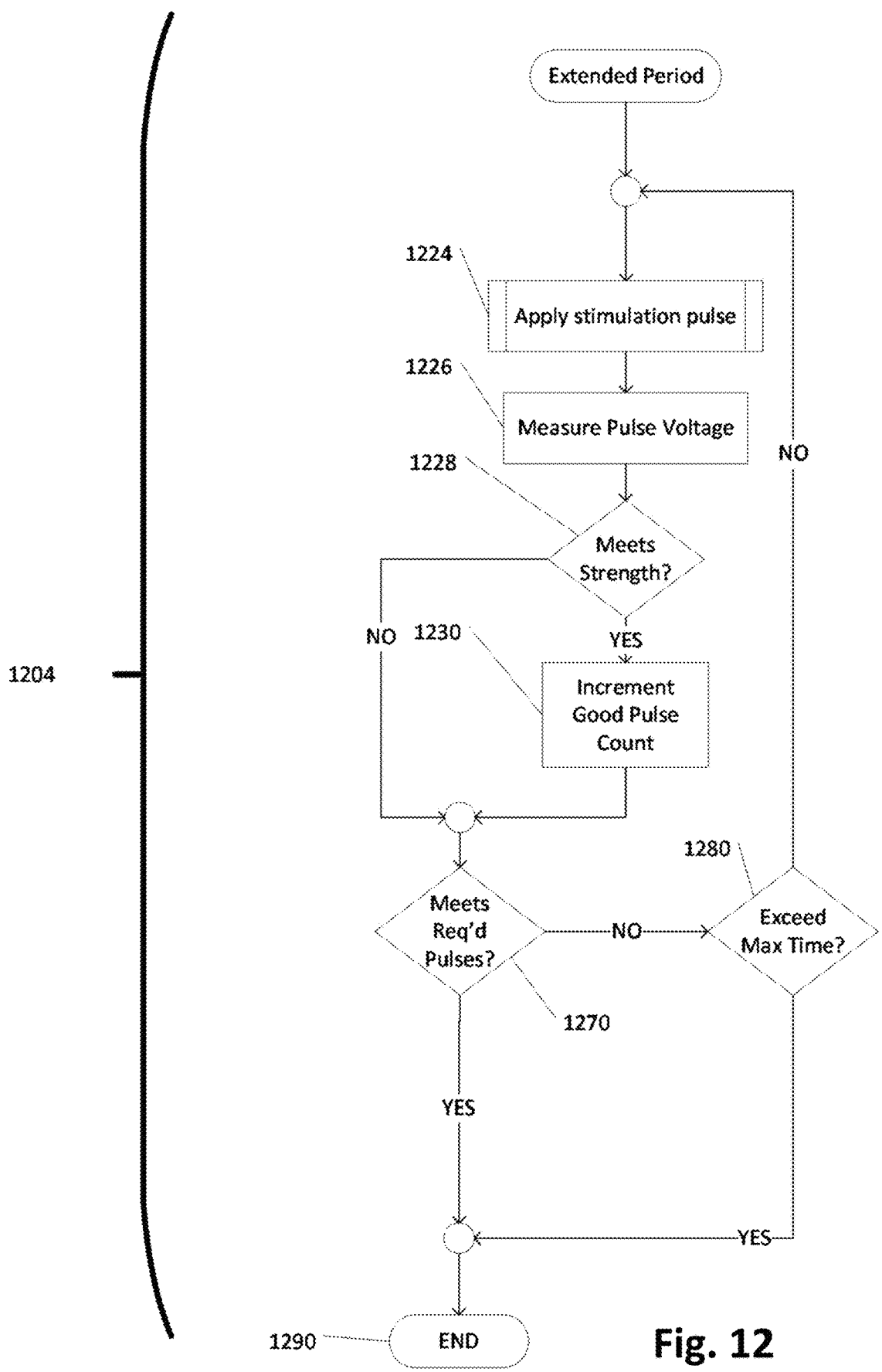

FIGS. 11 and 12 are flow diagrams of treatment monitoring functionality in accordance to example inventions. FIG. 11 is directed to a "normal" treatment monitoring process 1202, and begins with an initialization of ramp strength at 1210, and an initialization of a stage index at 1212 before treatment begins, followed by a normal application loop at 1220. Each iteration of the loop at 1220 applies a stimulation pulse at 1222, increments the pulse count at 1224 and then measures the pulse voltage at 1226. Each pulse amplitude is tested against a strength setting at 1228. In example inventions, the strength level is 1-20, producing voltages from 4V to 85V. Pulses, which do not achieve the target amplitude, are counted at 1230. A "good" pulse count is the number of pulses that meet the strength level, and a missed pulse count is the number of pulses minus the good pulse count. When the last treatment pulse has been applied at 1240, the count of missed pulses is compared to the missed pulse limit at 1250.

FIG. 12 is directed to an "extended" treatment monitoring functionality 1204 if at 1250 of FIG. 11 the amount of good pulse counts is not met. If more pulses have missed the target amplitude than are allowed by the missed pulse limit, then one or more extended treatment pulses at 1260 are applied. These pulses are added to the pulse count in the original treatment of FIG. 11, thereby lengthening the treatment time. When sufficient extended treatment pulses are applied to fulfill the number of necessary strength pulses at 1270, then the treatment completion at 1290 is achieved.

In example inventions, the target nerve stimulation pulse amplitude is set by one or more of the user, the firmware in patch 100, or the smart controller. To deliver at least the minimum number of pulses required for a treatment, patch 100 measures the amplitude of each applied stimulation pulse (i.e., the voltage level). A "normal" treatment is delivered in a fixed length of time. Each pulse, which does not achieve the target amplitude, is not counted as one of the pulses for the treatment minimum pulse count. When the normal treatment time has elapsed, patch 100 checks if the number of sufficiently strong pulses has met the minimum pulse count limit. If it has, the treatment is finished. If it has not, then additional pulses are applied to complete the treatment using the functionality of FIG. 12, thereby extending the duration of the treatment. If this extension exceeds a maximum treatment time at 1280, then the treatment is stopped at treatment completion 1290, even if the minimum number of applied strong pulses has not been met.

Patch 100 logs the counts of applied pulses, strong pulses, treatment time, and other parameters. This collected data may be transmitted to the smart controller or to another data storage device for later analysis.

Firmware Construction

As shown in FIG. 2, patch 100 includes control unit 1002. The set of features in control unit 1002 is used to provide control of the functions of patch 100 is the set of features most common across the set of specific control chips used for control unit 1002.

Differences in features offered on each of several chips available to build control unit 1002 results in an increase in firmware complexity when the firmware is designed to use a different set of features on each offered chip. This increase in complexity results in an increase in firmware problems across the set of patch 100s built on multiple chips, and increases the frequency of firmware updates needed to be delivered to that set of patch 100s. This increase in problems and updates limits the functionality of patch 100s in a subset of those users activating patch 100s on themselves.

By implementing function in the firmware using features compatible across the larger set of available chips, the complexity of the code, the frequency of firmware problems, and the frequency of firmware updates are reduced in example inventions.

In one example, between two different chips available as alternatives for control unit 1002, one chip provides interrupt service while in parallel performing analog to digital conversions in one or more peripherals such as ADCs. A second chip provides both interrupt service and ADC conversions, but not simultaneously or in parallel. Therefore, the patch 100 firmware is implemented using timer-based code rather than interrupt-based code, so that the same firmware may be executed on either of the two chips, thereby reducing the code to one compatible implementation.

In one example, between two different chips available as alternatives for control unit 1002, one chip provides support for many command types in the BLE wireless communication and a second chip provides support for only the lowest level BLE commands. Therefore, the firmware of patch 100 is implemented using only the lowest level BLE commands, such as single-write and single-read commands, thereby reducing the code to one compatible implementation.

BLE command coding bit errors when decoding commands received as byte values across the link between the smart controller or fob, and patch 100, can cause problems or latency delays in handling functions as requested by the smart controller or fob, such as writing data or reading data back, or initiating or terminating a function in patch 100. These bit errors are sometimes the result of weak signal quality between patch 100 and the smart controller or fob. The distances between these devices vary according to the habit of the user.

Patch 100 measures the receiving signal strength across BLE and quantifies it as a Received Signal Strength Indicator ("RSSI") binary value. The smart controller and/or fob requests these measured values using one or more of the BLE commands implemented in patch 100 and the smart controller and/or fob firmware. The smart controller and/or fob send these measured values to a computer or server or to the cloud to be analyzed. The analysis may correlate RSSI levels with retransmission rates of commands or data, and may calculate statistics for BLE function across a large population of patch 100s. These statistics and correlations are used to change the firmware and/or hardware designs of the smart controller, the fob or patch 100, to improve reliability and responsiveness.

BLE command opcodes are designed to minimize undetected bit errors when a command is received by patch 100. For each opcode with a binary pattern, there is a related opcode with the opposite binary pattern. Command opcodes, which differ by only one bit, are avoided.

Stack-Up of the Patch

Figure 13:
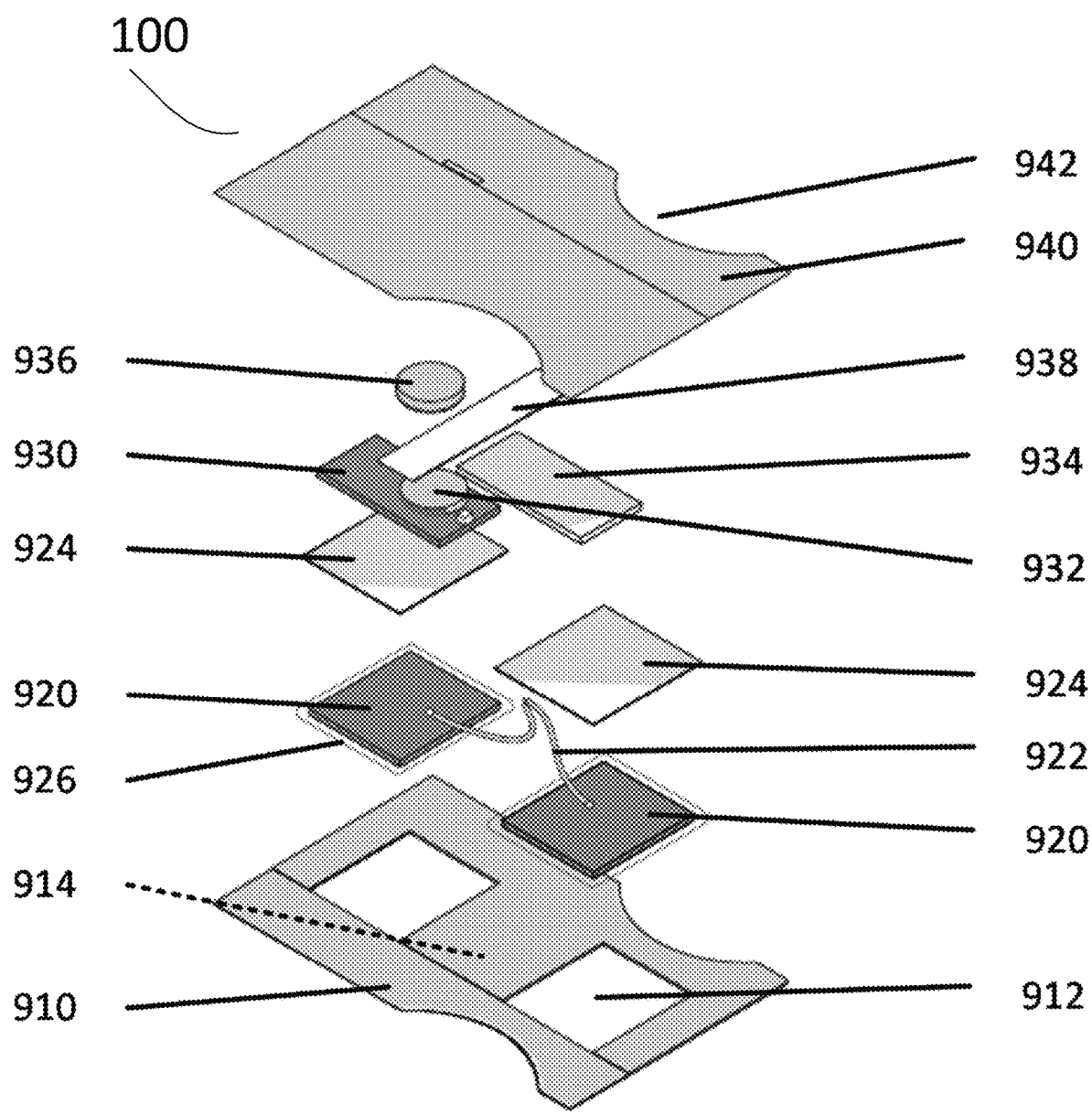
FIG. 13 illustrates a stack-up view of the patch in accordance with example inventions.

FIG. 13 illustrates a stack-up view of patch 100 in accordance with example inventions. A bottom layer 910 is a fabric tape with adhesive on the skin-facing side. A hole 912 is cut into the bottom layer for each of the electrodes 920. A removable paper 914 adheres to the adhesive on the skin-facing side of bottom layer 910. Two or more electrodes 920 are coupled by a wire 922 to a printed circuit board assembly ("PCBA") 930.

Electrodes 920 are covered with a polyimide tape A 924 to prevent short circuits from electrodes 920 to PCBA 930 and to prevent movement of electrodes 930 within the layers of the assembly. Each electrode 930 is coated on the skin-facing surface with hydrogel 926. Each electrode 920 has a release layer covering hydrogel 926. A battery clip 932 is attached to PCBA 930. A battery 936 is inserted into battery clip 932. A battery pull-tab 938 is inserted into battery clip 932. PCBA 930 is wrapped in polyimide tape B 934 to restrict access by the user to the electronics. A top layer 940 of fabric tape with adhesive on the PCBA-facing side is stacked on top to complete the assembly. Anklebone cutouts 942 are designed into the shapes of bottom layer 910 and top layer 940 to accommodate the ankle bone and to assist the user to correctly place patch 100.

Hydrogel Adaptation

Variations in the viscosity and composition of hydrogel 926 leads to variation in the migration of the substance from its original area on each electrode to a wider area, possibly touching the skin outside the dimensions of patch 100. As the hydrogel migrates, its electrical performance changes. The circuitry on PCBA 930 measures the voltage applied to the skin in real-time during the course of each treatment. The adaptive circuit calculates the charge delivered to the skin, which is a function of many parameters, including the conductivity of hydrogel 926. Therefore, the performance of patch 100 is maintained while the hydrogel portion of the device changes its performance. The adaptive circuit adjusts the delivery of charge to also account for all changes in body and skin conductivity, perspiration and patch contact.

As the performance of the hydrogel 926 decreases with time, the adaptive circuit and the firmware in PCBA 930 records the expected life of the specific patch while it is powered on and on the skin of the user. When patch 100 determines that the device's lifetime is near an end, the firmware signals to the fob or smart controller, such that the user receives an indication that this patch has reached its limit.

Crimped Connection from Electrode to PCBA

Each electrode 920 is coated with hydrogel 926 when the electrode is manufactured. In some examples, a wire 922 is connected to both the electrode and the PCBA 930 in a permanent fashion, such as by soldering, when electrodes 920 are manufactured. The electrode-plus-wire-plus-PCBA assemblies are each enclosed in an airtight bag until they are subsequently assembled with the tapes and adhesive layers to form a complete patch 100. Due to the complex nature of these assembly steps, the hydrogel on the electrodes may be exposed to air and humidity for a period of time, which affects the life expectancy of the hydrogel.

In an example, electrodes 920 are coated with hydrogel 926 but no wire is attached at that stage. Instead, a small clip is soldered to each electrode, which does not affect the hydrogel nor attach the electrode to any larger assembly, which would require longer time in the assembly line. These coated electrodes are each encased in an airtight bag with a heat seal or other means. The hydrogel does not degrade during the time that the coated electrode is inside the sealed bag.

In an example, wire 922 is inserted into the small clip which had previously been soldered to electrode 920, this connection being stronger and less prone to defect than the soldering or attachment of the wire strands directly to electrode 920. The clip and the wire do not affect hydrogel 926. Each coated electrode 920, with its clip and attached wire, is encased in an airtight bag with a heat seal or other means. Hydrogel 926 does not degrade during the time that the coated electrode is inside the sealed bag. The coated electrodes 920 are removed from their airtight bags only immediately before they are connected to PCBA 930.

An additional benefit of separating the coated electrodes 920 from PCBA 930 as two different subassemblies until put into a completed patch 100 is that coated electrodes found to be defective or expired from too lengthy time on the shelf may be discarded without the expense of discarding an already-attached PCBA. The more expensive PCBAs have a shelf life independent of the shelf life of the coated electrodes. These two subassemblies' inventories may be stocked, inspected and managed independently. This reduces the overall cost of manufacture of patches 100 devices without affecting their performance.

Die Cut Fabric Tape

In some examples, bottom layer 910 is placed as a layer over electrodes 920 using a solid layer of fabric tape. The overall thickness of patch 100 is therefore partly determined by the thickness of the fabric tape over electrodes 920. Further, in order to place electrodes 920 on the layer of fabric tape securely, the paper cover on the fabric tape must be pulled back to expose the adhesive coating. This results in a degradation of the adhesive properties of the tape.

In examples of patch 100, bottom layer 910 fabric tape is cut to create holes 912 for each of electrodes 920, according to the defined sizes of those components. Each electrode 920 is placed in the corresponding hole, without the added thickness of a fabric tape layer on top. Since no paper cover needs to be pulled back to mount electrodes 920 to the fabric tape, the adhesive of the fabric tape is not affected. The holes may be cut with a die in order to create accurate edges, without tears or fibers, which may interfere with electrodes 920.

Contoured to Ankle Bone

In some examples, patch 100 has a rectangular shape. This allows PCBA 930, battery 936 and electrodes 920 to fit in between fabric and adhesive bottom layer 910 and top layer 940, and to be affixed to the skin by the user, then to be peeled away and discarded after use. In some examples, patch 100 has a shape contoured to the position in which it is to be affixed to the skin. The reference point in properly positioning patch 100 is the malleolus, or ankle bone in some example uses. Therefore, patch 100 has an anklebone cutout 942 along the vertical side, this cutout accommodating the anklebone when patch 100 is placed close alongside the anklebone.

In some examples, cutout 942 is designed into patch 100 on only one side, such that battery 936, PCBA 930 and electrodes 920 are properly aligned on one of the left or the right ankle. Patch 100 can then be offered in two varieties—one for the left ankle with cutout 942 on the first vertical side, and one for the right ankle with cutout 942 on the second vertical side.

In some examples, cutout 942 is designed into patch 100 on both vertical sides, such that battery 936, PCBA 930 and electrodes 920 are properly aligned on either of the left or right ankle. Patch 100 can then be offered in only one variety.

Battery and Battery Tab

Patch 100 includes battery 936, which is enclosed by battery clip 932, assembled onto PCBA 930. During manufacturing, battery 936 is inserted into battery clip 932 to secure it from dropping out. In addition to the battery itself, battery pull-tab 938 is placed between one contact of battery 936 and the corresponding contact in battery clip 932. Battery pull-tab 938 prevents electrical connection between battery 936 and battery clip 932 at that contact until battery pull-tab 938 is removed. When in place, there is an open circuit such that patch 100 is not activated and does not consume power until battery pull-tab 938 is removed.

In some examples, battery pull-tab 938 is designed to be removed by pulling it out in the direction opposite that in which battery 936 was inserted into battery clip 932. This pulling action may lead to movement of the battery itself since it experiences a pulling force toward the open side of battery clip 932. This battery movement may cause patch 100 to cease operating or to never activate.

In one example, battery pull-tab 938 and battery clip 932 are designed so that battery pull tab 938 is pulled out in the same direction as battery 936 was pushed into battery clip 932. Therefore, the force pulling battery pull-tab 938 out of patch 100 serves only to make battery 936 more secure in its battery clip 932. This reduces the chance of inadvertent movement of battery 936 and the effect on activation or operation of patch 100.

Electrode Release Film

Each of electrodes 920 in the assembled patch 100 is covered with a Polyethylene Terephthalate ("PET") silicon covered release film 926. The release film is pulled away by the user when patch 100 is affixed to the skin. In some examples, the PET silicon covered release film 926 is transparent. This may lead to instances of confusion on the part of the user when the user may not be able to determine if the tape has been removed or not. Affixing patch 100 to the skin with any of electrodes 920 still covered with tape will cause patch 100 to be ineffective. This ineffectiveness may not be noticed until the first treatment with patch 100. If the affixed patch 100 is found to be ineffective when the user is feeling an urge to urinate, the user may struggle to either properly void their bladder or to remove patch 100, peel off the tapes from the electrodes or affix a new patch 100 and suppress the urge with the re-affixed or new device.

In examples, PET silicon covered release film 926 covering electrodes 920 is selected in a color conspicuous to the user, such that the user will readily determine if the tape has been removed or not.

Examples use circuitry and firmware to stimulate the electrode circuit with a brief, low energy pulse or pulse sequence when patch 100 is initially activated. If patch 100 is activated before it is affixed to the skin, the electrode readiness test will fail. In such a case, the electrode readiness test is repeated, again and again according to timers in the firmware or hardware, until either the timers have all expired or the test passes. The test passes when patch 100 is found to exhibit a circuit performance appropriate to its design. The test fails when patch 100 is not properly prepared, such as not removing the electrode films, or is not yet applied to the skin when the timers have all expired. When the electrode readiness test fails, patch 100 signals to the fob or the smart controller, which in turn informs the user. The electrode readiness test is implemented in a manner which may be undetectable by the user, and to minimize the test's use of battery power.

Removable Paper

In some examples, a removable paper 914 covers the adhesive side of bottom layer 910. Removable paper 914 may be in multiple sections, each to be pulled away by the user when affixing patch 100 to the skin. These removable papers may be in addition to the piece of PET film 926 covering each electrode 920. Therefore, the user must remove all of these pieces to expose a complete, adhesive surface to affix to the skin in examples.

In examples, bottom layer 910 is one complete piece, with one removable paper 914. The user removes all of the removable paper in one motion. In examples, bottom layer 910 is two or more pieces, with two or more removable papers 914. The user removes all of the removable papers. In examples, the single removable paper 914 is designed with a pull-tab, so that the user pulls the removable paper off of the bottom layer in a direction at right angle to the long axis of patch 100. This motion reduces the forces experienced by the assembled internal components of patch 100.

In examples, removable paper 914 covers bottom layer 910 and covers all of the PET film sections 926. An adhesive attaches the removable paper top surface to the polyimide tape A skin-facing surface, such that the user pulls the removable paper away from the bottom layer and in one motion removes the PET film pieces from electrodes 920.

Patch 100 can also be made more comfortable by the addition of material between the top layer and the bottom layer, such as cushioning material that can cushion the electrodes and electronic components. The cushioning material may be disposed subjacent to the bottom layer and superjacent to the top layer, in at least a portion of patch 100. A cushioning material may include cellulosic fibers (e.g., wood pulp fibers), other natural fibers, synthetic fibers, woven or nonwoven sheets, scrim netting or other stabilizing structures, superabsorbent material, foams, binder materials, or the like, as well as combinations thereof.

Hydrogel Overlaps Electrode Edges

In some examples, each electrode 920 is covered with hydrogel 926, which conforms to the size of the electrode 920, such that the edge of electrode 920 is exposed to the user's skin when patch 100 is applied to the skin. This edge may abrade or cut the user's skin during the time when patch 100 is affixed to the skin.

In some examples, hydrogel 926 is dimensioned so as to overlap the edges of electrode 920. Hydrogel 926 is placed over electrode 920 with the accuracies of placement used in manufacturing, such that the edges of electrode 920 is always covered with hydrogel 926. This keeps the edge electrode 920 from touching the user's skin. The risk of electrodes 920 from abrading or cutting the user's skin is therefore eliminated.

Figure 14:
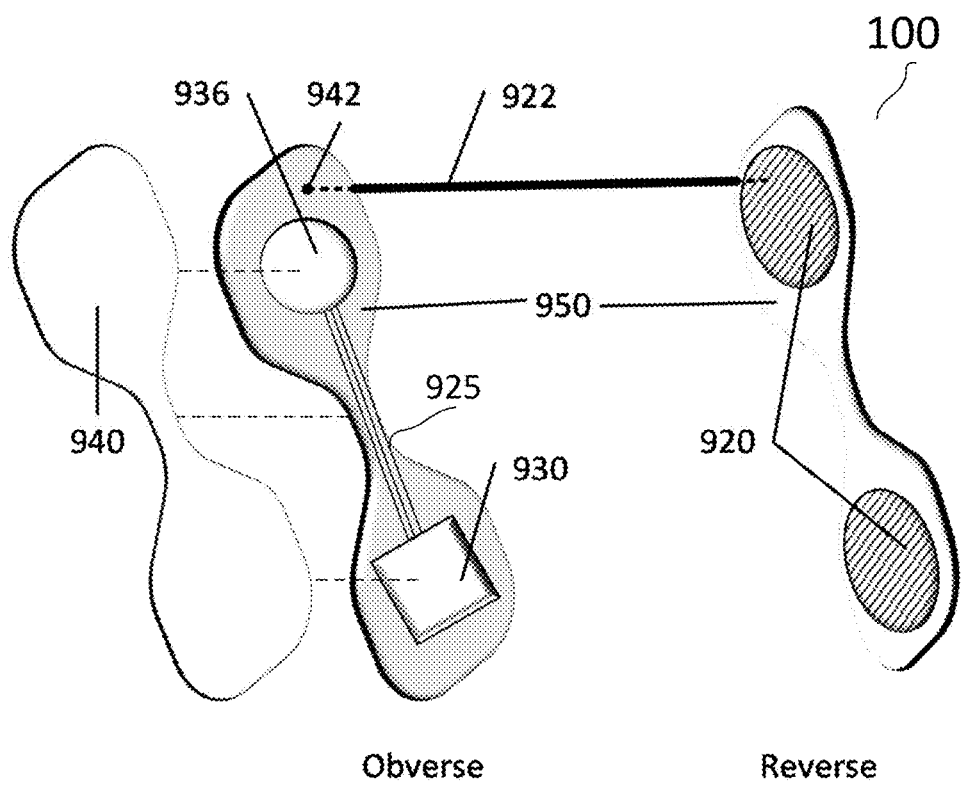
FIG. 14 illustrates a stack-up view of the patch in accordance with example inventions as assembled onto a substrate.

FIG. 14 illustrates a stack-up view of patch 100 in accordance with example inventions as assembled onto a substrate 950. Battery 936 is affixed to substrate 950 directly or via a battery clip, and connected to the electronics using two or more conducting paths plated onto substrate 950. Electrodes 920 are connected to the voltage and ground using vias 942, creating electrical paths from the top surface to the bottom surface of substrate 950. A top layer 940 is affixed over battery 936 to restrict access by the user to the electronics.

The distance between electrodes 920 may be selected to maximize the effectiveness of the electrical signal at the target nerve and/or minimize the footprint of patch 100. Each electrode 920 may have a body-facing surface area of from about 500 $mm^2$ to about 1100 $mm^2$. Electrodes 920 may have different or identical body-facing surface areas. The sum of the body-facing surface areas of the electrodes 920 may be less than 3,000 $mm^2$, preferably from about 1050 $mm^2$ to about 2200 $mm^2$, more preferably from about 500 $mm^2$ to 2200 $mm^2$.

Electrodes 920 may be spaced about 1 mm apart to about 100 mm apart (edge to edge), preferably about 5 mm apart to about 80 mm apart, more preferably about 10 mm apart to about 60 mm apart. The distance between the electrodes 920 may be selected to maximize the effectiveness of the electrical signal at the target nerve and/or minimize the footprint of the nerve stimulation device. Alternatively, patch 100 may include an array of electrodes. Further, as shown in FIG. 14, electrodes 920 are spaced apart by a relatively narrow isthmus 925. Isthmus 925 provides separation of electrodes 920 to enhance performance, and provides enhance wearing comfort and reduces wear during prolonged use for patch 100, particularly when patch 100 is placed on the ankle. Further, isthmus 925 relieves strain and the breaking of leads between the circuit and the battery, or other components.

Matrix Pattern in Electrodes

Figure 15:
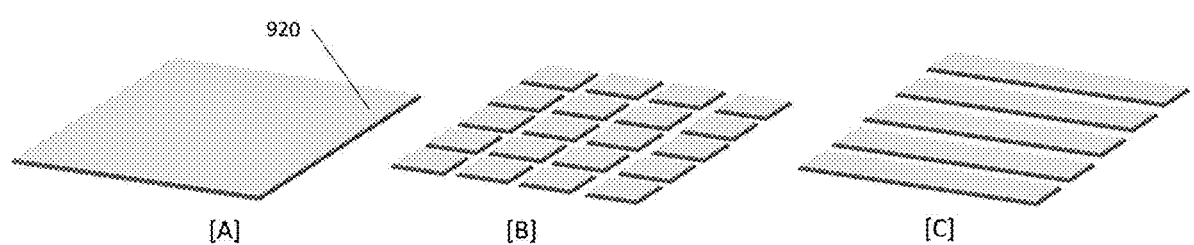
FIG. 15 illustrates solid and patterned electrodes that are used in different examples of the patch.

FIG. 15 illustrates solid and patterned electrodes that are used in different examples of patch 100. In an example, each of the two electrodes 920 is plated onto a substrate layer as a continuous area, as shown in FIGS. 14 and 15A.

In one example, each of the two electrodes 920 is plated in a matrix pattern, as shown in FIG. 15B, such that the surface of each electrode is planar. The ripples seen when using a continuous, plated area are absent, and the electrode lies flat against the user's skin. Each of the elements of the matrix is connected to a common electrical junction, which is driven by the activation voltage, such that the activation voltage is driven to all elements of the matrix simultaneously.

In one example, each of the two electrodes 920 is plated in a striped pattern, as shown in FIG. 15C, such that the surface of each electrode is planar. Each of the elements of the striped pattern is connected to a common electrical junction which is driven by the activation voltage, such that the activation voltage is driven to all elements of the matrix simultaneously. The common electrical junction may be in a layer of the PCB separate from the outer plated layer, or the junction may be formed by connecting the stripes around their perimeter or from stripe to stripe at midpoints.

In one example, a printed circuit board assembly ("PCBA") 930 (e.g., the use of one or both sides of the PCB, whether rigid or flexible, for the plating of conductive paths and the mounting of electronic components) is assembled onto a flexible substrate rather than a rigid substrate, as shown in FIG. 14, such that the ripples seen when using a rigid substrate are absent, and the PCBA lies flat against the User's skin.

The overall area of the electrode in matrix or striped form is calculated to provide sufficient coverage on the User's skin to allow for variations in placement of the electrode over the target location for nerve activation, such that, even if patch 100 is placed off-center from the optimum location, the electrodes extend across the target area sufficiently to deliver effective stimulation.

A layer of Hydrogel 926 coats each of electrodes 920 in example inventions. Although electrodes 920 are plated in a matrix or striped or similar pattern, the Hydrogel is a continuous area across each of the two Electrodes. This continuous conductive surface distributes the applied pulse voltage across an area of skin to avoid disturbing the surface of the skin.

Protection of Circuit Components

The layer of Hydrogel 926 coats the electrode side of PCBA 930. Vias are used to connect from the top surface of the PCB to the bottom surface, providing electrical connections for one or more of the components such as the SOC 1000. During use of patch 100, the Hydrogel may migrate through one or more of the vias to the top surface of the PCB. This migrated material, being conductive, may interfere with the performance of the one or more electrical components on the top surface of the PCB, such as causing a short circuit to ground or other voltage on one or more pins of such components, an example being the SOC 1000.

The PCB is manufactured with a layer covering the one or more through vias, this layer being affixed to the bottom side of the PCB. Hydrogel 926 is coated to the bottom side of the PCB after the application of the covering layer on the vias. The covering layer prevents the ingress and migration of Hydrogel or other contaminants such as water into and/or through the vias, thereby forming a permanent barrier so that the functionality of patch 100 is maintained through repeated use by the user. This covering layer also prevents ingress and migration during the time from manufacture to initial use by the User, thereby assuring shelf life of patch 100.

Hydrogel Impedance

The power required to perform a stimulation is related to the applied voltage and the impedance seen by electrodes 920 through Hydrogel 926 and the user's skin. When the Hydrogel has a higher impedance, more power is required to perform a stimulation. With the fixed power available from battery 936 in patch 100, this energy per stimulation sets a limit to the number of stimulations, which may be applied.

In an example, a Hydrogel 926 with a lower impedance has been selected to allow for less energy dissipated in the circuit, and more stimulations per patch 100 using battery 936. The Hydrogel's impedance may be minimized by one or more of reducing the Hydrogel coating thickness, changing the material composition, and increasing the size of the Hydrogel coating onto electrodes 920 even extending beyond the borders of the Electrodes onto the bottom surface of the PCBA 930.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A topical nerve activation patch comprising:
   a substrate;
   a dermis conforming bottom surface of the substrate comprising adhesive and adapted to contact a dermis of a user;
   a top outer surface of the substrate approximately parallel to the bottom surface;
   a plurality of electrodes positioned on the patch proximal to the bottom surface and located beneath the top outer surface and coupled to the substrate;
   a power source; and
   electronic circuitry embedded in the patch and located beneath the top outer surface and coupled to the substrate, the electronic circuitry configured to generate an output voltage applied to the electrodes, the electronic circuitry comprising:
      a controller configured to generate a treatment comprising a plurality of activation pulses that form the output voltage, the controller comprising a first real time clock and an oscillator having a known frequency, the treatment comprising electrical stimuli applied to the user via the electrodes;
      a charge measurement circuit configured to measure an amount of charge applied to the user from the electrical stimuli; and
      a communication link configured to communicate with a remote activation device, the remote activation device comprising a second real time clock;
      the controller configured to generate the activation pulses comprising:
         setting a timer using the oscillator;
         adjusting a value of a counter each time the timer elapses;
         sending the value of the counter to the remote activation device, the second real time clock adapted to determine activation times for the activation pulses by adding a value proportional to the value of the counter to a second real time clock value and sending the activation times to the controller.

2. The topical nerve activation patch of claim 1, the controller configured to generate the activation pulses without using the first real time clock.

3. The topical nerve activation patch of claim 1, the electronic circuitry further comprising a pulse width modulation (PWM) circuit configured to modify a width of one or more of the plurality of activation pulses during a PWM duty cycle.

4. The topical nerve activation patch of claim 3, the electronic circuitry further comprising a boosted voltage circuit configured to ramp a voltage level of each of the activation pulses to a desired level.

5. The topical nerve activation patch of claim 4, the controller configured to stop the boosted voltage circuit output between activation pulses until a next pulse is needed.

6. The topical nerve activation patch of claim 5, the controller configured to vary the PWM duty cycle during the plurality of activation pulses so that a lower PWM duty cycle is used at a beginning of the electrical stimuli to form relatively narrow pulses and a higher PWM duty cycle is used at an end of the electrical stimuli to form relatively wider pulses.

7. The topical nerve activation patch of claim 1, the treatment comprising a pulse count, the controller configured to determine during the generation of the plurality of activation pulses a count of a number of the activation pulses that achieve a predefined strength setting, and when the count does not exceed a predefined number, generating extra pulses to add to the pulse count.

8. The topical nerve activation patch of claim 1, the remote activation device comprising either a fob or a smart phone.

9. The topical nerve activation patch of claim 1, the charge measurement circuit comprising circuitry for determining an amount of charge required to recharge a boost regulator coupled to the electrodes.

10. The topical nerve activation patch of claim 1, the charge measurement circuit comprising circuitry for repeatedly sampling a voltage of the electrodes during a duration of one applied stimulation pulse.

11. The topical nerve activation patch of claim 1, at least one pair of the plurality of electrodes separated by an isthmus.

12. A method of activating a nerve of a user, the method comprising:
    attaching to the user a topical nerve activation patch, the patch comprising:
       a substrate;
       a dermis conforming bottom surface of the substrate comprising adhesive and adapted to contact a dermis of a user;
       a top outer surface of the substrate approximately parallel to the bottom surface;
       a plurality of electrodes positioned on the patch proximal to the bottom surface and located beneath the top outer surface and coupled to the substrate;
       a power source; and
       electronic circuitry embedded in the patch and located beneath the top outer surface and coupled to the substrate, the electronic circuitry comprising a controller, a charge measurement circuit, and a communication link;
    generating an output voltage applied to the electrodes, the electronic circuitry comprising:
    generating a treatment comprising a plurality of activation pulses that form the output voltage, the controller comprising a first real time clock and an oscillator, the treatment comprising electrical stimuli applied to the user via the electrodes having a known frequency;
    measuring an amount of charge applied to the user from the electrical stimuli;
    communicating with a remote activation device, the remote activation device comprising a second real time clock; and
    generating the activation pulses comprising:
       setting a timer using the oscillator;
       adjusting a value of a counter each time the timer elapses; and
       sending the value of the counter to the remote activation device, the second real time clock adapted to determine activation times for the activation pulses by adding a value proportional to the value of the counter to a second real time clock value and sending the activation times to the controller.

13. The method of claim 12, the controller generating the activation pulses without using the first real time clock.

14. The method of claim 12, the electronic circuitry further comprising a pulse width modulation (PWM) circuit, further comprising modifying a width of one or more of the plurality of activation pulses during a PWM duty cycle.

15. The method of claim 14, the electronic circuitry further comprising a boosted voltage circuit, further comprising ramping a voltage level of each of the activation pulses to a desired level.

16. The method of claim 15, further comprising stopping the boosted voltage circuit output between activation pulses until a next pulse is needed.

17. The method of claim 16, further comprising varying the PWM duty cycle during the plurality of activation pulses so that a lower PWM duty cycle is used at a beginning of the electrical stimuli to form relatively narrow pulses and a higher PWM duty cycle is used at an end of the electrical stimuli to form relatively wider pulses.

18. The method of claim 12, the treatment comprising a pulse count, further comprising determining during the generation of the plurality of activation pulses a count of a number of the activation pulses that achieve a predefined strength setting, and when the count does not exceed a predefined number, generating extra pulses to add to the pulse count.

19. The method of claim 12, the remote activation device comprising either a fob or a smart phone.

20. The method of claim 12, at least one pair of the plurality of electrodes separated by an isthmus.

\* \* \* \* \*